(12) United States Patent
Wilson et al.

(10) Patent No.: US 10,240,157 B2
(45) Date of Patent: Mar. 26, 2019

(54) DIAGNOSTIC AND SCREENING METHODS FOR ATOPIC DERMATITIS

(71) Applicant: The Regents of the University of California, Oakland, CA (US)

(72) Inventors: Sarah R. Wilson, Berkeley, CA (US); Lydia Thé, Berkeley, CA (US); Diana M. Bautista, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/704,917

(22) Filed: Sep. 14, 2017

(65) Prior Publication Data

US 2018/0100155 A1    Apr. 12, 2018

Related U.S. Application Data

(62) Division of application No. 14/500,000, filed on Sep. 29, 2014, now Pat. No. 9,790,506.

(60) Provisional application No. 61/885,972, filed on Oct. 2, 2013.

(51) Int. Cl.
| | |
|---|---|
| *C12N 15/113* | (2010.01) |
| *G01N 33/68* | (2006.01) |
| *G01N 33/50* | (2006.01) |
| *A61K 31/713* | (2006.01) |
| *C12Q 1/6883* | (2018.01) |

(52) U.S. Cl.
CPC ........ *C12N 15/1138* (2013.01); *A61K 31/713* (2013.01); *C12Q 1/6883* (2013.01); *G01N 33/5035* (2013.01); *G01N 33/6863* (2013.01); *G01N 33/6872* (2013.01); *C12N 2310/14* (2013.01); *C12Q 2600/136* (2013.01); *C12Q 2600/158* (2013.01); *G01N 2500/02* (2013.01); *G01N 2500/10* (2013.01); *G01N 2800/202* (2013.01)

(58) Field of Classification Search
CPC ............ C12N 15/1138; C12N 2310/14; C12Q 1/6883; C12Q 2600/158; C12Q 2600/136; G01N 33/5035; G01N 33/6872; G01N 2500/10; G01N 2800/202; G01N 2500/02; G01N 33/6863; A61K 31/713
See application file for complete search history.

(56) References Cited

U.S. PATENT DOCUMENTS

| | | |
|---|---|---|
| 2011/0020369 A1 | 1/2011 | Malefyt et al. |
| 2013/0004508 A1 | 1/2013 | Presta et al. |
| 2013/0084290 A1 | 4/2013 | Saris et al. |

OTHER PUBLICATIONS

Blagoev, et al.; "Cloning of rat thymic stromal lymphopoietin receptor (TSLPR) and characterization of genomic structure of murine Tslpr gene"; Gene; vol. 284, No. 1-2, pp. 161-168 (Feb. 6, 2002).

Reardon, et al.; "Thymic stromal lymphopoetin-induced expression of the endogenous inhibitory enzyme SLPI mediates recovery from colonic inflammation"; Immunity; vol. 35, No. 2, pp. 223-235 (Aug. 26, 2011).

Ziegler, et al.; "The Role of Thymic Stromal Lymphopoietin (TSLP) in Allergic Disorders"; Curr Opin Immunol; vol. 22, No. 6, pp. 795-799 (Dec. 1, 2010).

*Primary Examiner* — Ruixiang Li
(74) *Attorney, Agent, or Firm* — Bozicevic Field & Francis, LLP; Paula A. Borden; Payal B. Sud

(57) ABSTRACT

The present disclosure provides methods for identifying agents that are candidate agents for treating atopic dermatitis. The present disclosure provides methods for diagnosing atopic dermatitis. The present disclosure provides compositions and methods for treating atopic dermatitis.

19 Claims, 23 Drawing Sheets

Specification includes a Sequence Listing.

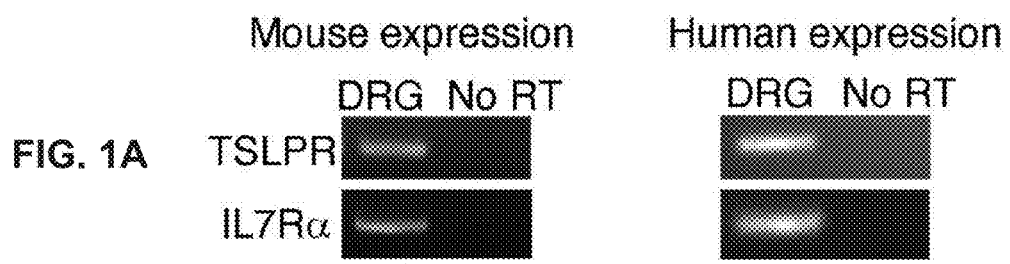
FIG. 1A
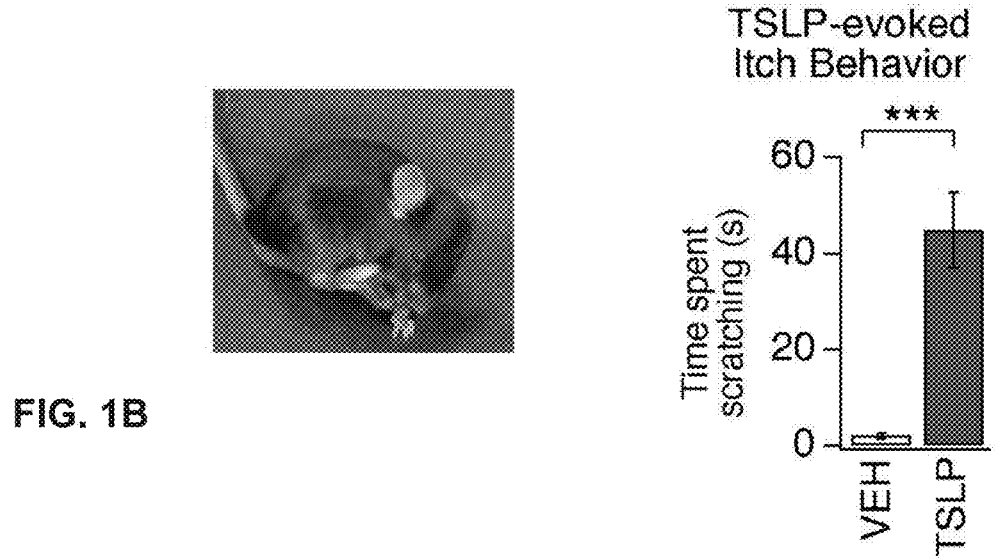
FIG. 1B
FIG. 1C

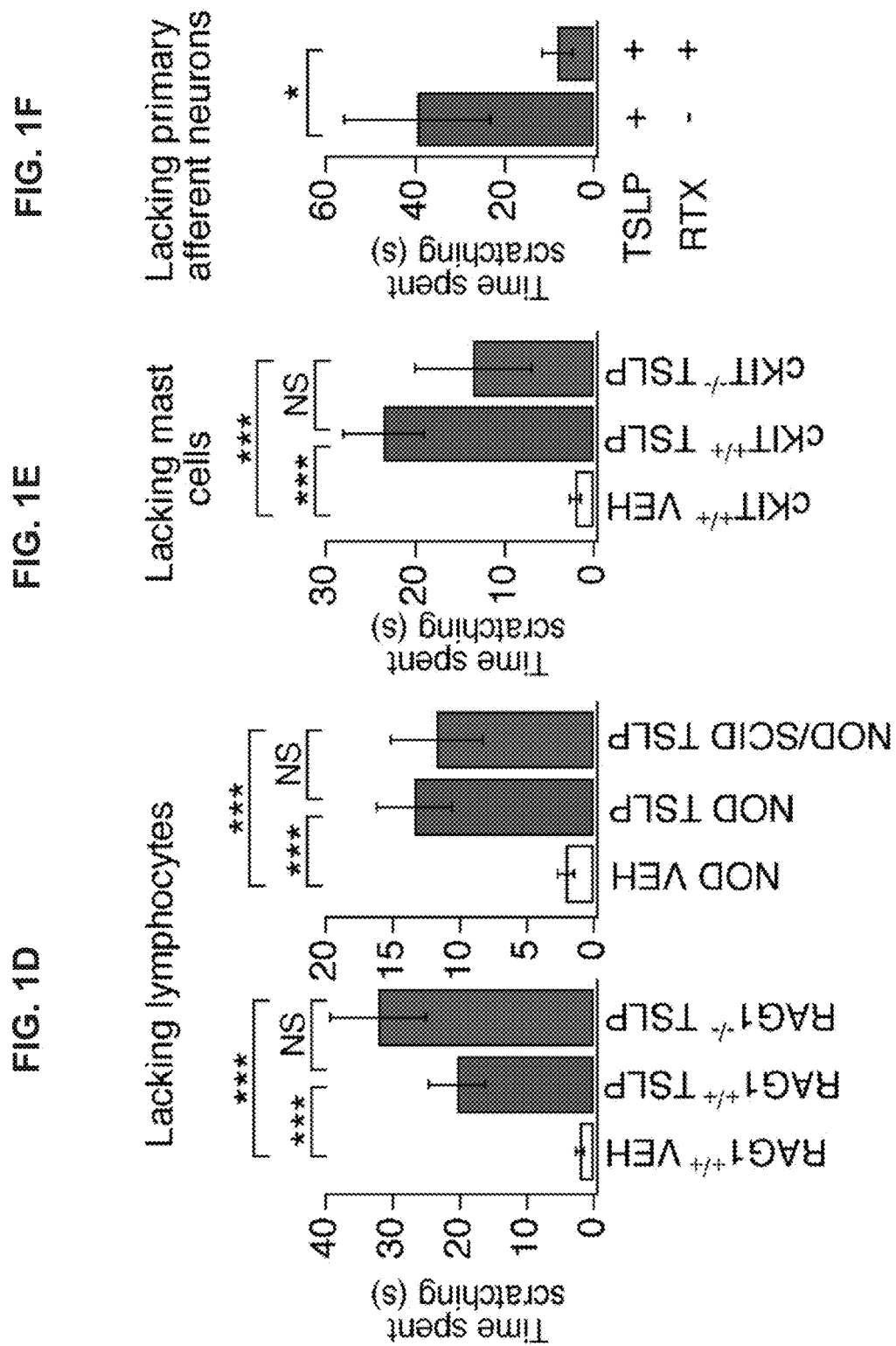

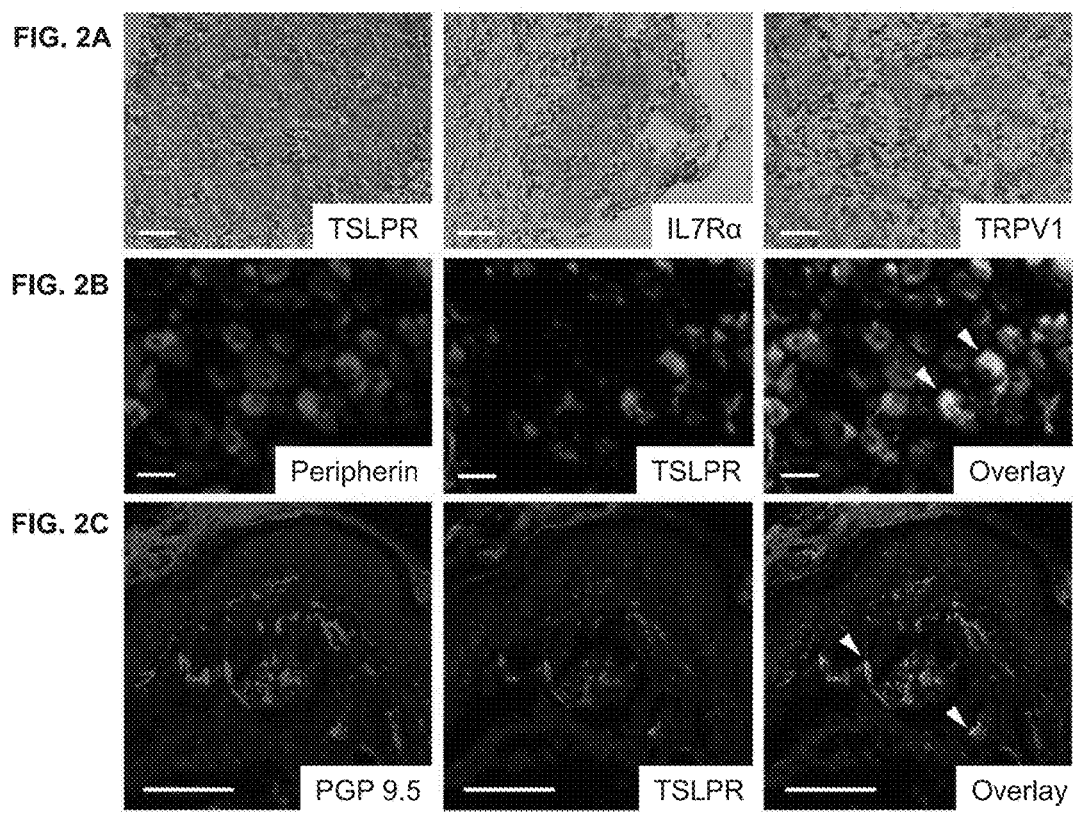

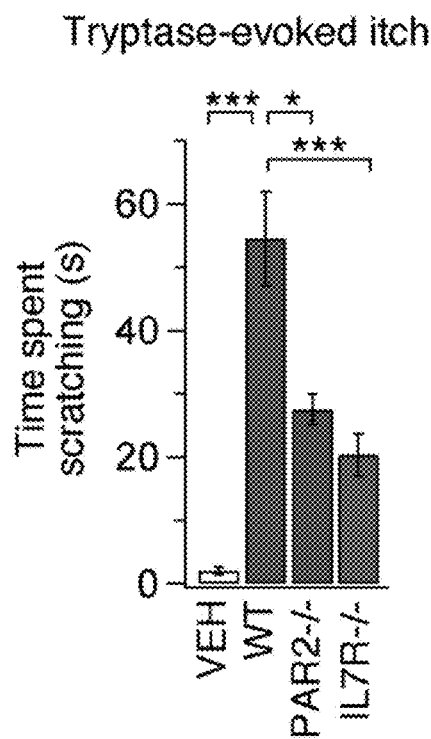
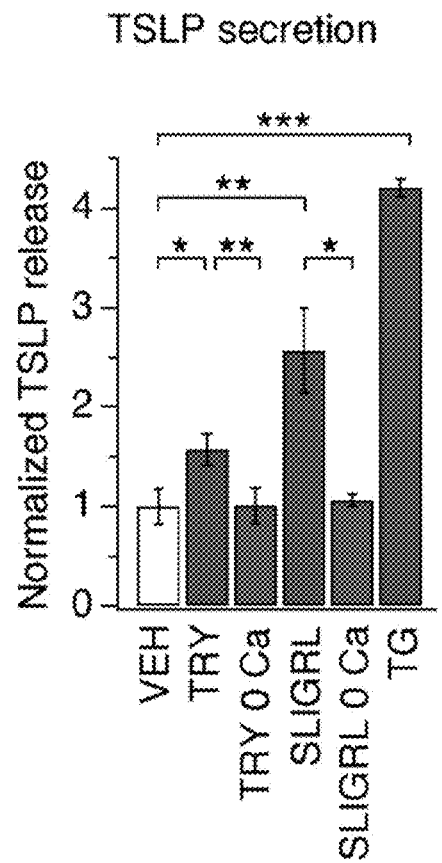
FIG. 5A
FIG. 5B

FIG. 6A
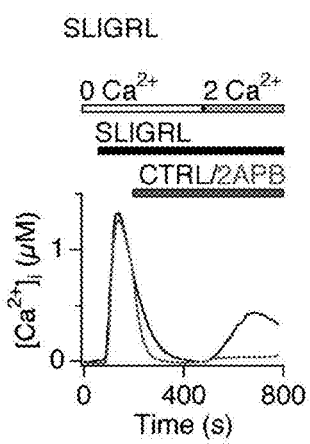
FIG. 6B
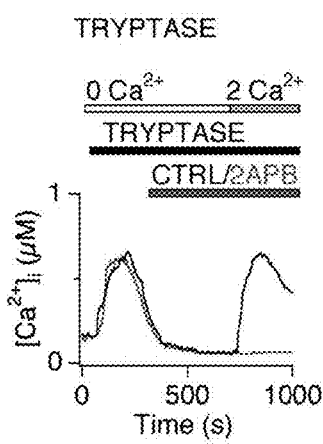
FIG. 6C
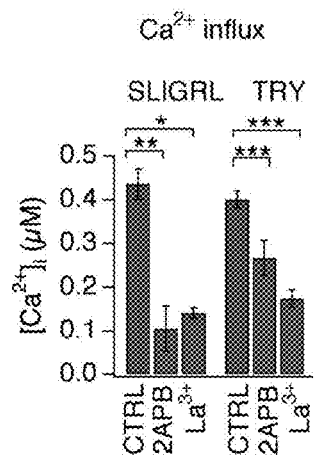
FIG. 6D
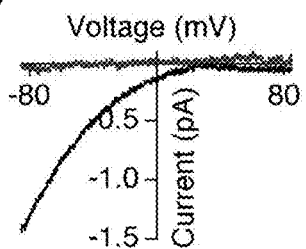
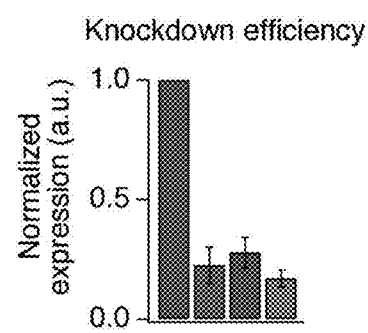
FIG. 6E
FIG. 6F
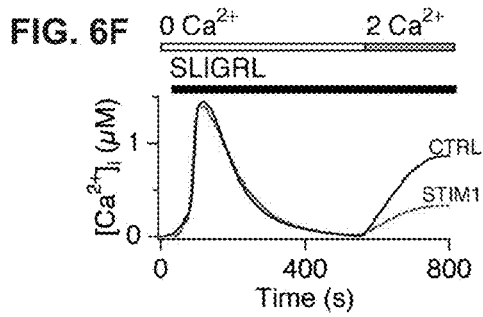
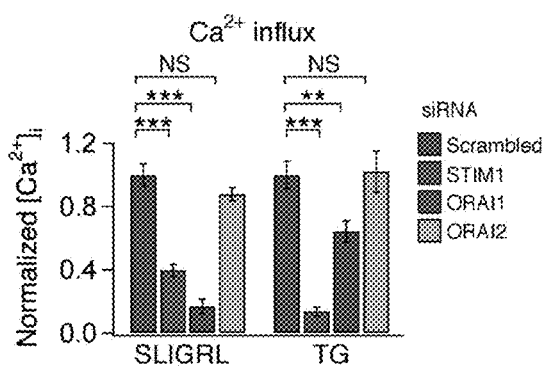
FIG. 6G

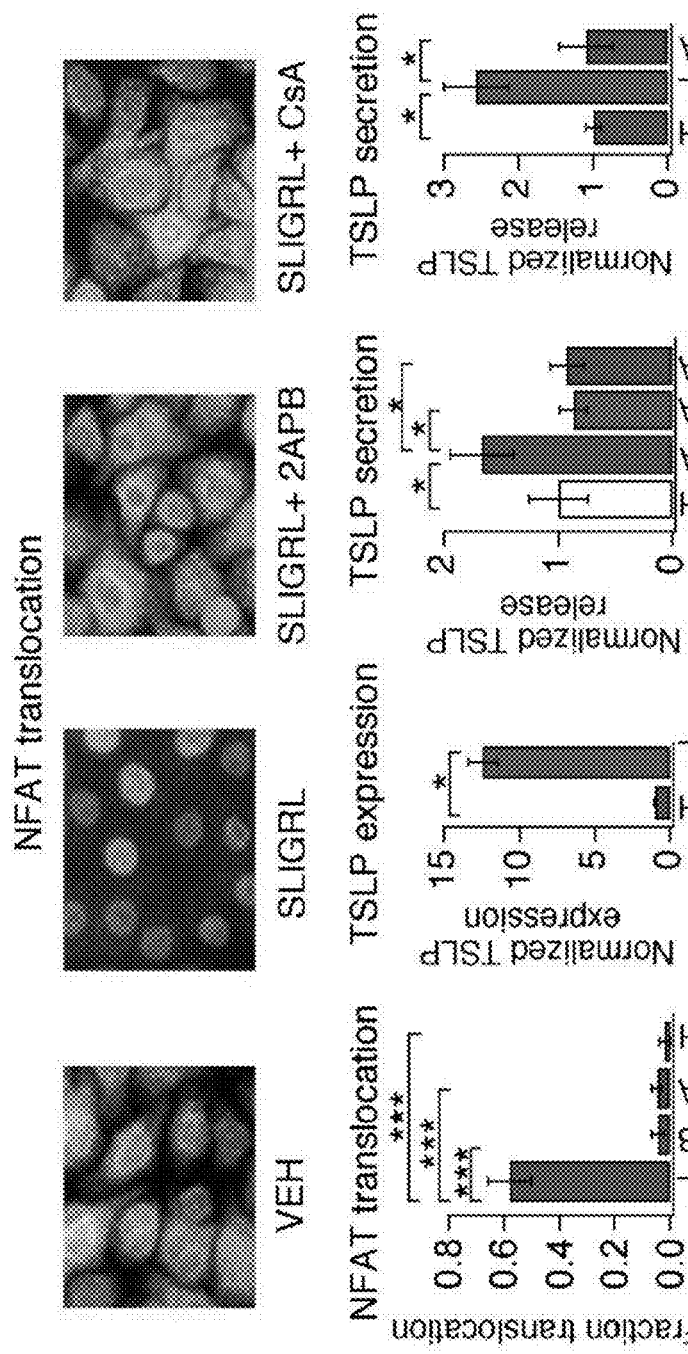
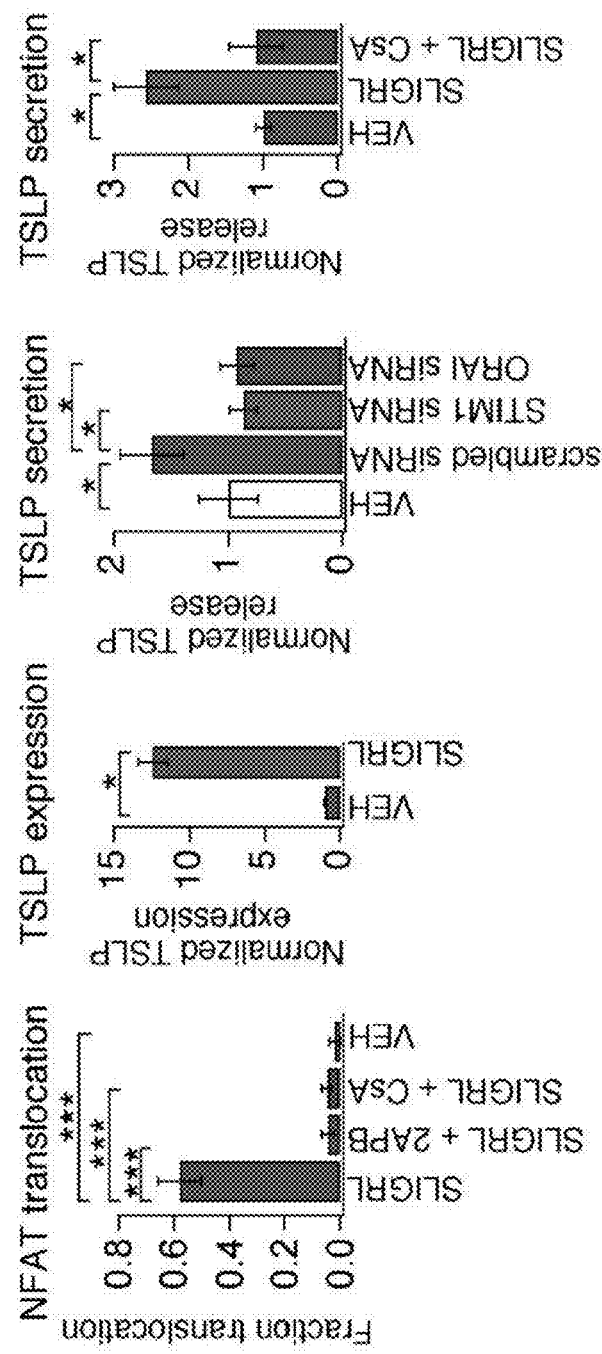
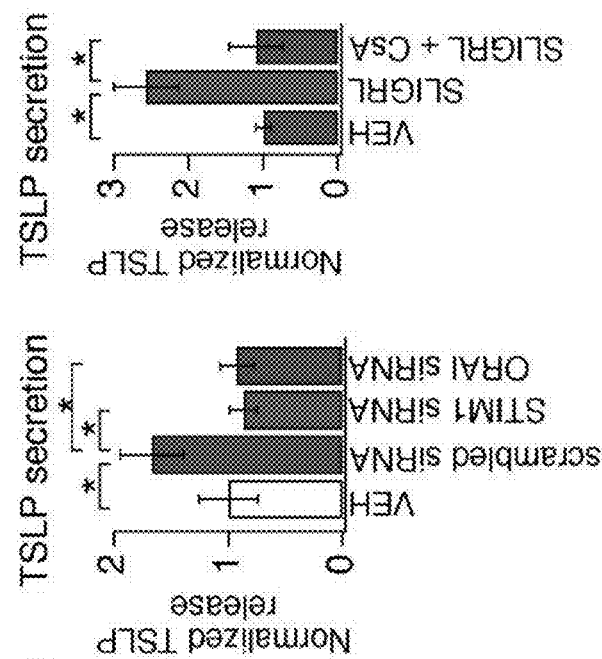
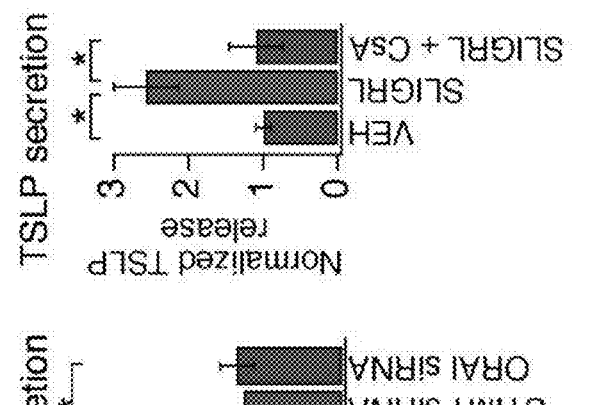
FIG. 7A, FIG. 7B, FIG. 7C, FIG. 7D, FIG. 7E

Figure 8

TSLPR (thymic stromal lymphopoietin protein receptor)
*Also called:* CRLF2 (cytokine receptor-like factor 2); CRL2 (cytokine receptor-like 2); and CRLF2Y

Human TSLPR Protein:
MGRLVLLWGAAVFLLGGWMALGQGGAAEGVQIQIIYFNLETVQVTWNASKYSRTNLTFHYRF
NGDEAYDQCTNYLLQEGHTSGCLLDAEQRDDILYFSIRNGTHPVFTASRWMVYYLKPSSPKH
VRFSWHQDAVTVTCSDLSYGDLLYEVQYRSPFDTEWQSKQENTCNVTIEGLDAEKCYSFWV
RVKAMEDVYGPDTYPSDWSEVTCWQRGEIRDACAETPTPPKPKLSKFILISSLAILLMVSLLLL
SLWKLWRVKKFLIPSVPDPKSIFPGLFEIHQGNFQEWITDTQNVAHLHKMAGAEQESGPEEPL
VVQLAKTEAESPRMLDPQTEEKEASGGSLQLPHQPLQGGDVVTIGGFTFVMNDRSYVAL

Human TSLPR cDNA:
ATGGGGCGGCTGGTTCTGCTGTGGGGAGCTGCCGTCTTTCTGCTGGGAGGCTGGATGG
CTTTGGGGCAAGGAGGAGCAGCAGAAGGAGTACAGATTCAGATCATCTACTTCAATTTAG
AAACCGTGCAGGTGACATGGAATGCCAGCAAATACTCCAGGACCAACCTGACTTTCCACT
ACAGATTCAACGGTGATGAGGCCTATGACCAGTGCACCAACTACCTTCTCCAGGAAGGTC
ACACTTCGGGGTGCCTCCTAGACGCAGAGCAGCGAGACGACATTCTCTATTTCTCCATCA
GGAATGGGACGCACCCCGTTTTCACCGCAAGTCGCTGGATGGTTTATTACCTGAAACCCA
GTTCCCCGAAGCACGTGAGATTTTCGTGGCATCAGGATGCAGTGACGGTGACGTGTTCT
GACCTGTCCTACGGGGATCTCCTCTATGAGGTTCAGTACCGGAGCCCCTTCGACACCGA
GTGGCAGTCCAAACAGGAAAATACCTGCAACGTCACCATAGAAGGCTTGGATGCCGAGA
AGTGTTACTCTTTCTGGGTCAGGGTGAAGGCTATGGAGGATGTATATGGGCCAGACACAT
ACCCAAGCGACTGGTCAGAGGTGACATGCTGGCAGAGAGGCGAGATTCGGGATGCCTGT
GCAGAGACACCAACGCCTCCCAAACCAAAGCTGTCCAAATTTATTTTAATTTCCAGCCTGG
CCATCCTTCTGATGGTGTCTCTCCTCCTTCTGTCTTTATGGAAATTATGGAGAGTGAAGAA
GTTTCTCATTCCCAGCGTGCCAGACCCGAAATCCATCTTCCCCGGGCTCTTTGAGATACA
CCAAGGGAACTTCCAGGAGTGGATCACAGACACCCAGAACGTGGCCCACCTCCACAAGA
TGGCAGGTGCAGAGCAAGAAAGTGGCCCGAGGAGCCCTGGTAGTCCAGTTGGCCAA
GACTGAAGCCGAGTCTCCAGGATGCTGGACCCACAGACCGAGGAGAAAGAGGCCTCT
GGGGGATCCCTCCAGCTTCCCCACCAGCCCTCCAAGGCGGTGATGTGGTCACAATCGG
GGGCTTCACCTTTGTGATGAATGACCGCTCCTACGTGGCGTTGTGA

Figure 9

TRPA1 (transient receptor potential cation channel, subfamily A, member 1)
*Also called:* ANKTM1 (ankyrin-like with transmembrane domains protein 1); and FEPS

Human TRPA1 Protein:
MKRSLRKMWRPGEKKEPQGVVYEDVPDDTEDFKESLKVVFEGSAYGLQNFNKQKKLKRCD
DMDTFFLHYAAAEGQIELMEKITRDSSLEVLHEMDDYGNTPLHCAVEKNQIESVKFLLSRGAN
PNLRNFNMMAPLHIAVQGMNNEVMKVLLEHRTIDVNLEGENGNTAVIIACTTNNSEALQILLKK
GAKPCKSNKWGCFPIHQAAFSGSKECMEIILRFGEEHGYSRQLHINFMNNGKATPLHLAVQN
GDLEMIKMCLDNGAQIDPVEKGRCTAIHFAATQGATEIVKLMISSYSGSVDIVNTTDGCHETML
HRASLFDHHELADYLISVGADINKIDSEGRSPLILATASASWNIVNLLLSKGAQVDIKDNFGRNF
LHLTVQQPYGLKNLRPEFMQMQQIKELVMDEDNDGCTPLHYACRQGGPGSVNNLLGFNVSI
HSKSKDKKSPLHFAASYGRINTCQRLLQDISDTRLLNEGDLHGMTPLHLAAKNGHDKVVQLLL
KKGALFLSDHNGWTALHHASMGGYTQTMKVILDTNLKCTDRLDEDGNTALHFAAREGHAKA
VALLLSHNADIVLNKQQASFLHLALHNKRKEVVLTIIRSKRWDECLKIFSHNSPGNKCPITEMIE
YLPECMKVLLDFCMLHSTEDKSCRDYYIEYNFKYLQCPLEFTKKTPTQDVIYEPLTALNAMVQ
NNRIELLNHPVCKEYLLMKWLAYGFRAHMMNLGSYCLGLIPMTILVVNIKPGMAFNSTGIINET
SDHSEILDTTNSYLIKTCMILVFLSSIFGYCKEAGQIFQQKRNYFMDISNVLEWIIYTTGIIFVLPLF
VEIPAHLQWQCGAIAVYFYWMNFLLYLQRFENCGIFIVMLEVILKTLLRSTVVFIFLLLAFGLSFY
ILLNLQDPFSSPLLSIIQTFSMMLGDINYRESFLEPYLRNELAHPVLSFAQLVSFTIFVPIVLMNLL
IGLAVGDIAEVQKHASLKRIAMQVELHTSLEKKLPLWFLRKVDQKSTIVYPNKPRSGGMLFHIF
CFLFCTGEIRQEIPNADKSLEMEILKQKYRLKDLTFLLEKQHELIKLIIQKMEIISETEDDDSHCSF
QDRFKKEQMEQRNSRWNTVLRAVKAKTHHLEP

Human TRPA1 cDNA:
ATGAAGCGCAGCCTGAGGAAGATGTGGCGCCCTGGAGAAAAGAAGGAGCCCCAGGGCG
TTGTCTATGAGGATGTGCCGGACGACACGGAGGATTTCAAGGAATCGCTTAAGGTGGTTT
TTGAAGGAAGTGCATATGGATTACAAAACTTTAATAAGCAAAAGAAATTAAAAAGATGTGA
CGATATGGACACCTTCTTCTTGCATTATGCTGCAGCAGAAGGCCAAATTGAGCTAATGGA
GAAGATCACCAGAGATTCCTCTTTGGAAGTGCTGCATGAAATGGATGATTATGGAAATAC
CCCTCTGCATTGTGCTGTAGAAAAAAACCAAATTGAAAGCGTTAAGTTTCTTCTCAGCAGA
GGAGCAAACCCAAATCTCCGAAACTTCAACATGATGGCTCCTCTCCACATAGCTGTGCAG
GGCATGAATAATGAGGTGATGAAGGTCTTGCTTGAGCATAGAACTATTGATGTTAATTTGG
AAGGAGAAAATGGAAACACAGCTGTGATCATTGCGTGCACCACAAATAATAGCGAAGCAT
TGCAGATTTTGCTTAAAAAGGAGCTAAGCCATGTAAATCAAATAAATGGGGATGTTTCCC
TATTCACCAAGCTGCATTTTCAGGTTCCAAAGAATGCATGGAAATAATACTAAGGTTTGGT
GAAGAGCATGGGTACAGTAGACAGTTGCACATTAACTTTATGAATAATGGGAAAGCCACC
CCTCTCCACCTGGCTGTGCAAAATGGTGACTTGGAAATGATCAAAATGTGCCTGGACAAT
GGTGCACAAATAGACCCAGTGGAGAAGGGAAGGTGCACAGCCATTCATTTTGCTGCCAC
CCAGGGAGCCACTGAGATTGTTAAACTGATGATATCGTCCTATTCTGGTAGCGTGGATATT
GTTAACACAACCGATGGATGTCATGAGACCATGCTTCACAGAGCTTCATTGTTTGATCACC
ATGAGCTAGCAGACTATTTAATTTCAGTGGGAGCAGATATTAATAAGATCGATTCTGAAGG
ACGCTCTCCACTTATATTAGCAACTGCTTCTGCATCTTGGAATATTGTAAATTTGCTACTCT
CTAAAGGTGCCCAAGTAGACATAAAAGATAATTTTGGACGTAATTTTCTGCATTTAACTGTA
CAGCAACCTTATGGATTAAAAAATCTGCGACCTGAATTTATGCAGATGCAACAGATCAAAG

Figure 9 (Cont.)

AGCTGGTAATGGATGAAGACAACGATGGGTGTACTCCTCTACATTATGCATGTAGACAGG
GGGGCCCTGGTTCTGTAAATAACCTACTTGGCTTTAATGTGTCCATTCATTCCAAAAGCAA
AGATAAGAAATCACCTCTGCATTTTGCAGCCAGTTATGGGCGTATCAATACCTGTCAGAG
GCTCCTACAAGACATAAGTGATACGAGGCTTCTGAATGAAGGTGACCTTCATGGAATGAC
TCCTCTCCATCTGGCAGCAAAGAATGGACATGATAAAGTAGTTCAGCTTCTTCTGAAAAAA
GGTGCATTGTTTCTCAGTGACCACAATGGCTGGACAGCTTTGCATCATGCGTCCATGGGC
GGGTACACTCAGACCATGAAGGTCATTCTTGATACTAATTTGAAGTGCACAGATCGCCTG
GATGAAGACGGGAACACTGCACTTCACTTTGCTGCAAGGGAAGGCCACGCCAAAGCCGT
TGCGCTTCTTCTGAGCCACAATGCTGACATAGTCCTGAACAAGCAGCAGGCCTCCTTTTT
GCACCTTGCACTTCACAATAAGAGGAAGGAGGTTGTTCTTACGATCATCAGGAGCAAAAG
ATGGGATGAATGTCTTAAGATTTTCAGTCATAATTCTCCAGGCAATAAATGTCCAATTACA
GAAATGATAGAATACCTCCCTGAATGCATGAAGGTACTTTAGATTTCTGCATGTTGCATT
CCACAGAAGACAAGTCCTGCCGAGACTATTATATCGAGTATAATTTCAAATATCTTCAATG
TCCATTAGAATTCACCAAAAAACACCTACACAGGATGTTATATATGAACCGCTTACAGCC
CTCAACGCAATGGTACAAAATAACCGCATAGAGCTTCTCAATCATCCTGTGTGTAAAGAAT
ATTTACTCATGAAATGGTTGGCTTATGGATTTAGAGCTCATATGATGAATTTAGGATCTTAC
TGTCTTGGTCTCATACCTATGACCATTCTCGTTGTCAATATAAAACCAGGAATGGCTTTCA
ACTCAACTGGCATCATCAATGAAACTAGTGATCATTCAGAAATACTAGATACCACGAATTC
ATATCTAATAAAAACTTGTATGATTTTAGTGTTTTTATCAAGTATATTTGGGTATTGCAAAGA
AGCGGGGCAAATTTTCCAACAGAAAAGGAATTATTTTATGGATATAAGCAATGTTCTTGAA
TGGATTATCTACACGACGGGCATCATTTTTGTGCTGCCCTTGTTTGTTGAAATACCAGCTC
ATCTGCAGTGGCAATGTGGAGCAATTGCTGTTTACTTCTATTGGATGAATTTCTTATTGTAT
CTTCAAAGATTTGAAAATTGTGGAATTTTTATTGTTATGTTGGAGGTAATTTTGAAAACTTT
GTTGAGGTCTACAGTTGTATTTATCTTCCTTCTTCTGGCTTTTGGACTCAGCTTTTACATCC
TCCTGAATTTACAGGATCCCTTCAGCTCTCCATTGCTTTCTATAATCCAGACCTTCAGCAT
GATGCTAGGAGATATCAATTATCGAGAGTCCTTCCTAGAACCATATCTGAGAAATGAATTG
GCACATCCAGTTCTGTCCTTTGCACAACTTGTTTCCTTCACAATATTTGTCCCAATTGTCCT
CATGAATTTACTTATTGGTTTGGCAGTTGGCGACATTGCTGAGGTCCAGAAACATGCATCA
TTGAAGAGGATAGCTATGCAGGTGGAACTTCATACCAGCTTAGAGAAGAAGCTGCCACTT
TGGTTTCTACGCAAAGTGGATCAGAAATCCACCATCGTGTATCCCAACAAACCCAGATCT
GGTGGGATGTTATTCCATATATTCTGTTTTTTATTTTGCACTGGGGAAATAAGACAAGAAAT
ACCAAATGCTGATAAATCTTTAGAAATGGAAATATTAAAGCAGAAATACCGGCTGAAGGAT
CTTACTTTTCTCCTGGAAAAACAGCATGAGCTCATTAAACTGATCATTCAGAAGATGGAGA
TCATCTCTGAGACAGAGGATGATGATAGCCATTGTTCTTTTCAAGACAGGTTTAAGAAAGA
GCAGATGGAACAAAGGAATAGCAGATGGAATACTGTGTTGAGAGCAGTCAAGGCAAAAAC
ACACCATCTTGAGCCTTAG

Figure 10

ORAI1 (ORAI calcium release-activated calcium modulator 1)
*Also called:* CRACM1; ORAT1; and TMEM142A

Human ORAI1 Protein:
MHPEPAPPPSRSSPELPPSGGSTTSGSRRSRRRSGDGEPPGAPPPPPSAVTYPDWIGQSYS
EVMSLNEHSMQALSWRKLYLSRAKLKASSRTSALLSGFAMVAMVEVQLDADHDYPPGLLIAF
SACTTVLVAVHLFALMISTCILPNIEAVSNVHNLNSVKESPHERMHRHIELAWAFSTVIGTLLFL
AEVVLLCWVKFLPLKKQPGQPRPTSKPPASGAAANVSTSGITPGQAAAIASTTIMVPFGLIFIVF
AVHFYRSLVSHKTDRQFQELNELAEFARLQDQLDHRGDHPLTPGSHYA

Human ORAI1 cDNA:
ATGCATCCGGAGCCCGCCCCGCCCCCGAGCCGCAGCAGTCCCGAGCTTCCCCCAAGCG
GCGGCAGCACCACCAGCGGCAGCCGCCGGAGCCGCCGCCGCAGCGGGGACGGGGAG
CCCCCGGGGGCCCCGCCACCGCCGCCGTCCGCCGTCACCTACCCGGACTGGATCGGCC
AGAGTTACTCCGAGGTGATGAGCCTCAACGAGCACTCCATGCAGGCGCTGTCCTGGCGC
AAGCTCTACTTGAGCCGCGCCAAGCTTAAAGCCTCCAGCCGGACCTCGGCTCTGCTCTC
CGGCTTCGCCATGGTGGCAATGGTGGAGGTGCAGCTGGACGCTGACCACGACTACCCA
CCGGGGCTGCTCATCGCCTTCAGTGCCTGCACCACAGTGCTGGTGGCTGTGCACCTGTT
TGCGCTCATGATCAGCACCTGCATCCTGCCCAACATCGAGGCGGTGAGCAACGTGCACA
ATCTCAACTCGGTCAAGGAGTCCCCCCATGAGCGCATGCACCGCCACATCGAGCTGGCC
TGGGCCTTCTCCACCGTCATCGGCACGCTGCTCTTCCTAGCTGAGGTGGTGCTGCTCTG
CTGGGTCAAGTTCTTGCCCCTCAAGAAGCAGCCAGGCCAGCCAAGGCCCACCAGCAAGC
CCCCCGCCAGTGGCGCAGCAGCCAACGTCAGCACCAGCGGCATCACCCCGGGCCAGGC
AGCTGCCATCGCCTCGACCACCATCATGGTGCCCTTCGGCCTGATCTTTATCGTCTTCGC
CGTCCACTTCTACCGCTCACTGGTTAGCCATAAGACTGACCGACAGTTCCAGGAGCTCAA
CGAGCTGGCGGAGTTTGCCCGCTTACAGGACCAGCTGGACCACAGAGGGGACCACCCC
CTGACGCCCGGCAGCCACTATGCCTAG

Figure 11

ORAI2 (ORAI calcium release-activated calcium modulator 2)
*Also called:* CBCIP2 (CAP-binding protein complex interacting protein 2); MEM142B; and TMEM142B

Human ORAI2 Protein (isoform a):
MSAELNVPIDPSAPACPEPGHKGMDYRDWVRRSYLELVTSNHHSVQALSWRKLYLSRAKLK
ASSRTSALLSGFAMVAMVEVQLETQYQYPRPLLIAFSACTTVLVAVHLFALLISTCILPNVEAVS
NIHNLNSISESPHERMHPYIELAWGFSTVLGILLFLAEVVLLCWIKFLPVDARRQPGPPPGPGS
HTGWQAALVSTIIMVPVGLIFVVFTIHFYRSLVRHKTERHNREIEELHKLKVQLDGHERSLQVL

Human ORAI2 Protein (isoform b):
MVEVQLETQYQYPRPLLIAFSACTTVLVAVHLFALLISTCILPNVEAVSNIHNLNSISESPHERM
HPYIELAWGFSTVLGILLFLAEVVLLCWIKFLPVDARRQPGPPPGPGSHTGWQAALVSTIIMVP
VGLIFVVFTIHFYRSLVRHKTERHNREIEELHKLKVQLDGHERSLQVL

Human ORAI2 cDNA (isoform a):
ATGAGTGCTGAGCTTAACGTGCCTATCGACCCCTCTGCTCCTGCCTGCCCTGAGCCCGG
CCATAAGGGCATGGATTACCGGGACTGGGTCCGCCGCAGCTACCTGGAACTGGTCACCT
CTAACCACCACTCGGTACAGGCCCTGTCGTGGCGGAAGCTCTACCTGAGCAGGGCCAAG
CTGAAGGCCTCCAGCAGGACCTCCGCCCTCCTCCGGCTTTGCCATGGTGGCCATGGT
GGAGGTGCAGCTGGAGACGCAGTACCAGTACCCGCGGCCGCTGCTGATTGCCTTCAGC
GCCTGCACCACGGTGCTGGTGGCCGTGCACCTGTTCGCCCTCCTCATCAGCACCTGCAT
CCTGCCCAATGTGGAGGCCGTGAGCAACATCCACAACCTGAACTCCATCAGCGAGTCCC
CGCATGAGCGCATGCACCCCTACATCGAGCTGGCCTGGGGCTTCTCCACCGTGCTTGGC
ATCCTACTCTTCCTGGCCGAGGTGGTGCTGCTCTGCTGGATCAAGTTCCTCCCCGTGGAT
GCCCGGCGCCAGCCTGGCCCCCACCTGGCCCTGGGAGTCACACGGGCTGGCAGGCC
GCCCTGGTGTCCACCATCATCATGGTGCCCGTGGGCCTCATCTTCGTGGTCTTCACCATC
CACTTCTACCGCTCCCTGGTGCGCCACAAAACGGAGCGCCACAACCGCGAGATCGAGGA
GCTCCACAAGCTCAAGGTCCAGCTGGACGGGCATGAGCGCAGCCTGCAGGTCTTGTGA

Human ORAI2 cDNA (isoform b):
ATGGTGGAGGTGCAGCTGGAGACGCAGTACCAGTACCCGCGGCCGCTGCTGATTGCCTT
CAGCGCCTGCACCACGGTGCTGGTGGCCGTGCACCTGTTCGCCCTCCTCATCAGCACCT
GCATCCTGCCCAATGTGGAGGCCGTGAGCAACATCCACAACCTGAACTCCATCAGCGAG
TCCCCGCATGAGCGCATGCACCCCTACATCGAGCTGGCCTGGGGCTTCTCCACCGTGCT
TGGCATCCTACTCTTCCTGGCCGAGGTGGTGCTGCTCTGCTGGATCAAGTTCCTCCCCGT
GGATGCCCGGCGCCAGCCTGGCCCCCACCTGGCCCTGGGAGTCACACGGGCTGGCA
GGCCGCCCTGGTGTCCACCATCATCATGGTGCCCGTGGGCCTCATCTTCGTGGTCTTCA
CCATCCACTTCTACCGCTCCCTGGTGCGCCACAAAACGGAGCGCCACAACCGCGAGATC
GAGGAGCTCCACAAGCTCAAGGTCCAGCTGGACGGGCATGAGCGCAGCCTGCAGGTCT
TGTGA

Figure 12 A

STIM1 (Stromal Interaction Molecule 1)
*Also called:* GOK; and TAM

Human STIM1 Protein (isoform 1):
MDVCVRLALWLLWGLLLHQGQSLSHSHSEKATGTSSGANSEESTAAEFCRIDKPLCHSEDEK
LSFEAVRNIHKLMDDDANGDVDVEESDEFLREDLNYHDPTVKHSTFHGEDKLISVEDLWKAW
KSSEVYNWTVDEVVQWLITYVELPQYEETFRKLQLSGHAMPRLAVTNTTMTGTVLKMTDRSH
RQKLQLKALDTVLFGPPLLTRHNHLKDFMLVVSIVIGVGGCWFAYIQNRYSKEHMKKMMKDLE
GLHRAEQSLHDLQERLHKAQEEHRTVEVEKVHLEKKLRDEINLAKQEAQRLKELREGTENER
SRQKYAEEELEQVREALRKAEKELESHSSWYAPEALQKWLQLTHEVEVQYYNIKKQNAEKQL
LVAKEGAEKIKKKRNTLFGTFHVAHSSSLDDVDHKILTAKQALSEVTAALRERLHRWQQIEILC
GFQIVNNPGIHSLVAALNIDPSWMGSTRPNPAHFIMTDDVDDMEEIVSPLSMQSPSLQSSVR
QRLTEPQHGLGSQRLVEGEAGHFLTSRVSLRRMRSLSSGQSFSSEGYGTSSPSASAAASCS
SSITTITTTTTTTTFTTVHVHPVYYHHSTSYFLQMEPYPDTPPSDSTAVMPGHSESLGDLTHS
DSESSLHMSDRQRVAPKPPQMSRAADEALNAMTSNGSHRLIEGVHPGSLVEKLPDSPALAK
KALLALNHGLDKAHSLMELSPSAPPGGSPHLDSSRSHSPSSPDPDTPSPVGDSRALQASRNT
RIPHLAGKKAVAEEDNGSIGEETDSSPGRKKFPLKIFKKPLKK

Human STIM1 Protein (isoform 2):
MDVCVRLALWLLWGLLLHQGQSLSHSHSEKATGTSSGANSEESTAAEFCRIDKPLCHSEDEK
LSFEAVRNIHKLMDDDANGDVDVEESDEFLREDLNYHDPTVKHSTFHGEDKLISVEDLWKAW
KSSEVYNWTVDEVVQWLITYVELPQYEETFRKLQLSGHAMPRLAVTNTTMTGTVLKMTDRSH
RQKLQLKALDTVLFGPPLLTRHNHLKDFMLVVSIVIGVGGCWFAYIQNRYSKEHMKKMMKDLE
GLHRAEQSLHDLQERLHKAQEEHRTVEVEKVHLEKKLRDEINLAKQEAQRLKELREGTENER
SRQKYAEEELEQVREALRKAEKELESHSSWYAPEALQKWLQLTHEVEVQYYNIKKQNAEKQL
LVAKEGAEKIKKKRNTLFGTFHVAHSSSLDDVDHKILTAKQALSEVTAALRERLHRWQQIEILC
GFQIVNNPGIHSLVAALNIDPSWMGSTRPNPAHFIMTDDVDDMEEIVSPLSMQSPSLQSSVR
QRLTEPQHGLGSQRDLTHSDSESSLHMSDRQRVAPKPPQMSRAADEALNAMTSNGSHRLIE
GVHPGSLVEKLPDSPALAKKALLALNHGLDKAHSLMELSPSAPPGGSPHLDSSRSHSPSSPD
PDTPSPVGDSRALQASRNTRIPHLAGKKAVAEEDNGSIGEETDSSPGRKKFPLKIFKKPLKK

Human STIM1 Protein (isoform 3):
MDVCVRLALWLLWGLLLHQGQSLSHSHSEKATGTSSGANSEESTAAEFCRIDKPLCHSEDEK
LSFEAVRNIHKLMDDDANGDVDVEESDEFLREDLNYHDPTVKHSTFHGEDKLISVEDLWKAW
KSSEVYNWTVDEVVQWLITYVELPQYEETFRKLQLSGHAMPRLAVTNTTMTGTVLKMTDRSH
RQKLQLKALDTVLFGPPLLTRHNHLKDFMLVVSIVIGVGGCWFAYIQNRYSKEHMKKMMKDLE
GLHRAEQSLHDLQERLHKAQEEHRTVEVEKVHLEKKLRDEINLAKQEAQRLKELREGTENER
SRQKYAEEELEQVREALRKAEKELESHSSWYAPEALQKWLQLTHEVEVQYYNIKKQNAEKQL
LVAKEGAEKIKKKRNTLFGTFHVAHSSSLDDVDHKILTAKQALSEVTAALRERLHRWQQIEILC
GFQIVNNPGIHSLVAALNIDPSWMGSTRPNPAHFIMTDDVDDMEEIVSPLSMQSPSLQSSVR
QRLTEPQHGLGSQRGSSLKANRLSSKGFDPFRFGVLPPHE

Figure 12 B

Human STIM1 cDNA (isoform 1):
ATGGATGTATGCGTCCGTCTTGCCCTGTGGCTCCTCTGGGGACTCCTCCTGCACCAGGG
CCAGAGCCTCAGCCATAGTCACAGTGAGAAGGCGACAGGAACCAGCTCGGGGGCCAAC
TCTGAGGAGTCCACTGCAGCAGAGTTTTGCCGAATTGACAAGCCCTGTGTCACAGTGAG
GATGAGAAACTCAGCTTCGAGGCAGTCCGTAACATCCACAAACTGATGGACGATGATGCC
AATGGTGATGTGGATGTGGAAGAAAGTGATGAGTTCCTGAGGGAAGACCTCAATTACCAT
GACCCAACAGTGAAACACAGCACCTTCCATGGTGAGGATAAGCTCATCAGCGTGGAGGA
CCTGTGGAAGGCATGGAAGTCATCAGAAGTATACAATTGGACCGTGGATGAGGTGGTAC
AGTGGCTGATCACATATGTGGAGCTGCCTCAGTATGAGGAGACCTTCCGGAAGCTGCAG
CTCAGTGGCCATGCCATGCCAAGGCTGGCTGTCACCAACACCACCATGACAGGGACTGT
GCTGAAGATGACAGACCGGAGTCATCGGCAGAAGCTGCAGCTGAAGGCTCTGGATACAG
TGCTCTTTGGGCCTCCTCTCTTGACTCGCCATAATCACCTCAAGGACTTCATGCTGGTGG
TGTCTATCGTTATTGGTGTGGGCGGCTGCTGGTTTGCCTATATCCAGAACCGTTACTCCA
AGGAGCACATGAAGAAGATGATGAAGGACTTGGAGGGGTTACACCGAGCTGAGCAGAGT
CTGCATGACCTTCAGGAAAGGCTGCACAAGGCCCAGGAGGAGCACCGCACAGTGGAGG
TGGAGAAGGTCCATCTGGAAAAGAAGCTGCGCGATGAGATCAACCTTGCTAAGCAGGAA
GCCCAGCGGCTGAAGGAGCTGCGGGAGGGTACTGAGAATGAGCGGAGCCGCCAAAAAT
ATGCTGAGGAGGAGTTGGAGCAGGTCGGGAGGCCTTGAGGAAAGCAGAGAAGGAGCT
AGAATCTCACAGCTCATGGTATGCTCCAGAGGCCCTTCAGAAGTGGCTGCAGCTGACACA
TGAGGTGGAGGTGCAATATTACAACATCAAGAAGCAAAATGCTGAGAAGCAGCTGCTGGT
GGCCAAGGAGGGGGCTGAGAAGATAAAAAAGAAGAGAAACACACTCTTTGGCACCTTCC
ACGTGGCCCACAGCTCTTCCCTGGATGATGTAGATCATAAAATTCTAACAGCTAAGCAAG
CACTGAGCGAGGTGACAGCAGCATTGCGGGAGCGCCTGCACCGCTGGCAACAGATCGA
GATCCTCTGTGGCTTCCAGATTGTCAACAACCCTGGCATCCACTCACTGGTGGCTGCCCT
CAACATAGACCCCAGCTGGATGGGCAGTACACGCCCCAACCCTGCTCACTTCATCATGAC
TGACGACGTGGATGACATGGATGAGGAGATTGTGTCTCCCTTGTCCATGCAGTCCCCTAG
CCTGCAGAGCAGTGTTCGGCAGCGCCTGACGGAGCCACAGCATGGCCTGGGATCTCAG
AGGTTGGTAGAGGGCGAGGCTGGCCACTTCTTGACAAGCCGGGTATCTCTGCGGCGAAT
GCGCAGCCTTTCATCTGGACAGTCTTTCAGTTCTGAAGGCTACGGGACCAGCTCTCCATC
TGCCTCTGCTGCTGCTTCTTGCTCCTCTTCCATCACCACCATCACCACTACCACCACCACC
ACCACCACCTTCACCACCGTCCATGTCCACCCTGTTTATTACCACCACAGCACTTCCTATT
TCCTCCAGATGGAGCCCTACCCTGACACACCCCTTCTGACAGCACCGCTGTGATGCCT
GGGCATTCAGAGAGCTTGGGGGATTTGACCCATTCCGATTCGGAGTCCTCCCTCCACATG
AGTGACCGCCAGCGTGTGGCCCCCAAACCTCCTCAGATGAGCCGTGCTGCAGACGAGG
CTCTCAATGCCATGACTTCCAATGGCAGCCACCGGCTGATCGAGGGGGTCCACCCAGGG
TCTCTGGTGGAGAAACTGCCTGACAGCCCTGCCCTGGCCAAGAAGGCATTACTGGCGCT
GAACCATGGGCTGGACAAGGCCCACAGCCTGATGGAGCTGAGCCCCTCAGCCCCACCT
GGTGGCTCTCCACATTTGGATTCTTCCCGTTCTCACAGCCCCAGCTCCCAGACCCAGAC
ACACCATCTCCAGTTGGGGACAGCCGAGCCCTGCAAGCCAGCCGAAACACACGCATTCC
CCACCTGGCTGGCAAGAAGGCTGTGGCTGAGGAGGATAATGGCTCTATTGGCGAGGAAA
CAGACTCCAGCCCAGGCCGGAAGAAGTTTCCCCTCAAAATCTTTAAGAAGCCTCTTAAGA
AGTAG

Figure 12 C

Human STIM1 cDNA (isoform 2):
ATGGATGTATGCGTCCGTCTTGCCCTGTGGCTCCTCTGGGGACTCCTCCTGCACCAGGG
CCAGAGCCTCAGCCATAGTCACAGTGAGAAGGCGACAGGAACCAGCTCGGGGGCCAAC
TCTGAGGAGTCCACTGCAGCAGAGTTTTGCCGAATTGACAAGCCCCTGTGTCACAGTGAG
GATGAGAAACTCAGCTTCGAGGCAGTCCGTAACATCCACAAACTGATGGACGATGATGCC
AATGGTGATGTGGATGTGGAAGAAAGTGATGAGTTCCTGAGGGAAGACCTCAATTACCAT
GACCCAACAGTGAAACACAGCACCTTCCATGGTGAGGATAAGCTCATCAGCGTGGAGGA
CCTGTGGAAGGCATGGAAGTCATCAGAAGTATACAATTGGACCGTGGATGAGGTGGTAC
AGTGGCTGATCACATATGTGGAGCTGCCTCAGTATGAGGAGACCTTCCGGAAGCTGCAG
CTCAGTGGCCATGCCATGCCAAGGCTGGCTGTCACCAACACCACCATGACAGGGACTGT
GCTGAAGATGACAGACCGGAGTCATCGGCAGAAGCTGCAGCTGAAGGCTCTGGATACAG
TGCTCTTTGGGCCTCCTCTCTTGACTCGCCATAATCACCTCAAGGACTTCATGCTGGTGG
TGTCTATCGTTATTGGTGTGGGCGGCTGCTGGTTTGCCTATATCCAGAACCGTTACTCCA
AGGAGCACATGAAGAAGATGATGAAGGACTTGGAGGGGTTACACCGAGCTGAGCAGAGT
CTGCATGACCTTCAGGAAGGCTGCACAAGGCCCAGGAGGAGCACCGCACAGTGGAGG
TGGAGAAGGTCCATCTGGAAAAGAAGCTGCGCGATGAGATCAACCTTGCTAAGCAGGAA
GCCAGCGGCTGAAGGAGCTGCGGGAGGGTACTGAGAATGAGCGGAGCCGCCAAAAAT
ATGCTGAGGAGGAGTTGGAGCAGGTTCGGGAGGCCTTGAGGAAAGCAGAGAAGGAGCT
AGAATCTCACAGCTCATGGTATGCTCCAGAGGCCCTTCAGAAGTGGCTGCAGCTGACACA
TGAGGTGGAGGTGCAATATTACAACATCAAGAAGCAAAATGCTGAGAAGCAGCTGCTGGT
GGCCAAGGAGGGGGCTGAGAAGATAAAAAAGAAGAGAAACACACTCTTTGGCACCTTCC
ACGTGGCCCACAGCTCTTCCCTGGATGATGTAGATCATAAAATTCTAACAGCTAAGCAAG
CACTGAGCGAGGTGACAGCAGCATTGCGGGAGCGCCTGCACCGCTGGCAACAGATCGA
GATCCTCTGTGGCTTCCAGATTGTCAACAACCCTGGCATCCACTCACTGGTGGCTGCCCT
CAACATAGACCCCAGCTGGATGGGCAGTACACGCCCCAACCCTGCTCACTTCATCATGAC
TGACGACGTGGATGACATGGATGAGGAGATTGTGTCTCCTTGTCCATGCAGTCCCCTAG
CCTGCAGAGCAGTGTTCGGCAGCGCCTGACGGAGCCACAGCATGGCCTGGGATCTCAG
AGGGATTTGACCCATTCCGATTCGGAGTCCTCCCTCCACATGAGTGACCGCCAGCGTGT
GGCCCCCAAACCTCCTCAGATGAGCCGTGCTGCAGACGAGGCTCTCAATGCCATGACTT
CCAATGGCAGCCACCGGCTGATCGAGGGGGTCCACCCAGGGTCTCTGGTGGAGAAACT
GCCTGACAGCCCTGCCCTGGCCAAGAAGGCATTACTGGCGCTGAACCATGGGCTGGACA
AGGCCCACAGCCTGATGGAGCTGAGCCCCTCAGCCCCACCTGGTGGCTCTCCACATTTG
GATTCTTCCCGTTCTCACAGCCCCAGCTCCCAGACCCAGACACACCATCTCCAGTTGGG
GACAGCCGAGCCCTGCAAGCCAGCCGAAACACACGCATTCCCCACCTGGCTGGCAAGAA
GGCTGTGGCTGAGGAGGATAATGGCTCTATTGGCGAGGAAACAGACTCCAGCCCAGGCC
GGAAGAAGTTTCCCCTCAAAATCTTTAAGAAGCCTCTTAAGAAGTAG

Figure 12 D

Human STIM1 cDNA (isoform 3):
ATGGATGTATGCGTCCGTCTTGCCCTGTGGCTCCTCTGGGGACTCCTCCTGCACCAGGG
CCAGAGCCTCAGCCATAGTCACAGTGAGAAGGCGACAGGAACCAGCTCGGGGGCCAAC
TCTGAGGAGTCCACTGCAGCAGAGTTTTGCCGAATTGACAAGCCCCTGTGTCACAGTGAG
GATGAGAAACTCAGCTTCGAGGCAGTCCGTAACATCCACAAACTGATGGACGATGATGCC
AATGGTGATGTGGATGTGGAAGAAAGTGATGAGTTCCTGAGGGAAGACCTCAATTACCAT
GACCCAACAGTGAAACACAGCACCTTCCATGGTGAGGATAAGCTCATCAGCGTGGAGGA
CCTGTGGAAGGCATGGAAGTCATCAGAAGTATACAATTGGACCGTGGATGAGGTGGTAC
AGTGGCTGATCACATATGTGGAGCTGCCTCAGTATGAGGAGACCTTCCGGAAGCTGCAG
CTCAGTGGCCATGCCATGCCAAGGCTGGCTGTCACCAACACCACCATGACAGGGACTGT
GCTGAAGATGACAGACCGGAGTCATCGGCAGAAGCTGCAGCTGAAGGCTCTGGATACAG
TGCTCTTTGGGCCTCCTCTCTTGACTCGCCATAATCACCTCAAGGACTTCATGCTGGTGG
TGTCTATCGTTATTGGTGTGGGCGGCTGCTGGTTTGCCTATATCCAGAACCGTTACTCCA
AGGAGCACATGAAGAAGATGATGAAGGACTTGGAGGGGTTACACCGAGCTGAGCAGAGT
CTGCATGACCTTCAGGAAAGGCTGCACAAGGCCCAGGAGGAGCACCGCACAGTGGAGG
TGGAGAAGGTCCATCTGGAAAAGAAGCTGCGCGATGAGATCAACCTTGCTAAGCAGGAA
GCCCAGCGGCTGAAGGAGCTGCGGGAGGGTACTGAGAATGAGCGGAGCCGCCAAAAAT
ATGCTGAGGAGGAGTTGGAGCAGGTTCGGGAGGCCTTGAGGAAAGCAGAGAAGGAGCT
AGAATCTCACAGCTCATGGTATGCTCCAGAGGCCCTTCAGAAGTGGCTGCAGCTGACACA
TGAGGTGGAGGTGCAATATTACAACATCAAGAAGCAAAATGCTGAGAAGCAGCTGCTGGT
GGCCAAGGAGGGGGCTGAGAAGATAAAAAAGAAGAGAAACACACTCTTTGGCACCTTCC
ACGTGGCCCACAGCTCTTCCCTGGATGATGTAGATCATAAAATTCTAACAGCTAAGCAAG
CACTGAGCGAGGTGACAGCAGCATTGCGGGAGCGCCTGCACCGCTGGCAACAGATCGA
GATCCTCTGTGGCTTCCAGATTGTCAACAACCCTGGCATCCACTCACTGGTGGCTGCCCT
CAACATAGACCCCAGCTGGATGGGCAGTACACGCCCCAACCCTGCTCACTTCATCATGAC
TGACGACGTGGATGACATGGATGAGGAGATTGTGTCTCCCTTGTCCATGCAGTCCCCTAG
CCTGCAGAGCAGTGTTCGGCAGCGCCTGACGGAGCCACAGCATGGCCTGGGATCTCAG
AGAGGATCATCTCTAAAGGCAAACAGGCTCTCTAGTAAGGGATTTGACCCATTCCGATTC
GGAGTCCTCCCTCCACATGAGTGA

Figure 13

TSLP (thymic stromal lymphopoietin)

Human TSLP Protein (isoform 1):
MFPFALLYVLSVSFRKIFILQLVGLVLTYDFTNCDFEKIKAAYLSTISKDLITYMSGTKSTEFNNT
VSCSNRPHCLTEIQSLTFNPTAGCASLAKEMFAMKTKAALAIWCPGYSETQINATQAMKKRRK
RKVTTNKCLEQVSQLQGLWRRFNRPLLKQQ

Human TSLP Protein (isoform 2):
MFAMKTKAALAIWCPGYSETQINATQAMKKRRKRKVTTNKCLEQVSQLQGLWRRFNRPLLK
QQ

Human TSLP cDNA (isoform 1):
ATGTTCCCTTTTGCCTTACTATATGTTCTGTCAGTTTCTTTCAGGAAAATCTTCATCTTACAA
CTTGTAGGGCTGGTGTTAACTTACGACTTCACTAACTGTGACTTTGAGAAGATTAAAGCAG
CCTATCTCAGTACTATTTCTAAAGACCTGATTACATATATGAGTGGGACCAAAAGTACCGA
GTTCAACAACACCGTCTCTTGTAGCAATCGGCCACATTGCCTTACTGAAATCCAGAGCCT
AACCTTCAATCCCACCGCCGGCTGCGCGTCGCTCGCCAAAGAAATGTTCGCCATGAAAA
CTAAGGCTGCCTTAGCTATCTGGTGCCCAGGCTATTCGGAAACTCAGATAAATGCTACTC
AGGCAATGAAGAAGAGGAGAAAAAGGAAAGTCACAACCAATAAATGTCTGGAACAAGTGT
CACAATTACAAGGATTGTGGCGTCGCTTCAATCGACCTTTACTGAAACAACAGTAA

Human TSLP cDNA (isoform 2):
ATGTTCGCCATGAAAACTAAGGCTGCCTTAGCTATCTGGTGCCCAGGCTATTCGGAAACT
CAGATAAATGCTACTCAGGCAATGAAGAAGAGGAGAAAAAGGAAAGTCACAACCAATAAA
TGTCTGGAACAAGTGTCACAATTACAAGGATTGTGGCGTCGCTTCAATCGACCTTTACTGA
AACAACAGTAA

Figure 14

PAR2 (protease-activated receptor 2)
*Also called:* F2RL1 (coagulation factor II (thrombin) receptor-like 1); and GPR11 (G-protein coupled receptor 11)

Human PAR2 Protein:
MRSPSAAWLLGAAILLAASLSCSGTIQGTNRSSKGRSLIGKVDGTSHVTGKGVTVETVFSVDE
FSASVLTGKLTTVFLPIVYTIVFVVGLPSNGMALWVFLFRTKKKHPAVIYMANLALADLLSVIWF
PLKIAYHIHGNNWIYGEALCNVLIGFFYGNMYCSILFMTCLSVQRYWVIVNPMGHSRKKANIAI
GISLAIWLLILLVTIPLYVVKQTIFIPALNITTCHDVLPEQLLVGDMFNYFLSLAIGVFLFPAFLTAS
AYVLMIRMLRSSAMDENSEKKRKRAIKLIVTVLAMYLICFTPSNLLLVVHYFLIKSQGQSHVYAL
YIVALCLSTLNSCIDPFVYYFVSHDFRDHAKNALLCRSVRTVKQMQVSLTSKKHSRKSSSYSS
SSTTVKTSY

Human PAR2 cDNA:
ATGCGGAGCCCCAGCGCGGCGTGGCTGCTGGGGGCCGCCATCCTGCTAGCAGCCTCTC
TCTCCTGCAGTGGCACCATCCAAGGAACCAATAGATCCTCTAAAGGAAGAAGCCTTATTG
GTAAGGTTGATGGCACATCCCACGTCACTGGAAAAGGAGTTACAGTTGAAACAGTCTTTT
CTGTGGATGAGTTTTCTGCATCTGTCCTCACTGGAAAACTGACCACTGTCTTCCTTCCAAT
TGTCTACACAATTGTGTTTGTGGTGGGTTTGCCAAGTAACGGCATGGCCCTGTGGGTCTT
TCTTTTCCGAACTAAGAAGAAGCACCCTGCTGTGATTTACATGGCCAATCTGGCCTTGGCT
GACCTCCTCTGTCATCTGGTTCCCCTTGAAGATTGCCTATCACATACATGGCAACAACT
GGATTTATGGGGAAGCTCTTTGTAATGTGCTTATTGGCTTTTTCTATGGCAACATGTACTG
TTCCATTCTCTTCATGACCTGCCTCAGTGTGCAGAGGTATTGGGTCATCGTGAACCCCAT
GGGGCACTCCAGGAAGAAGGCAAACATTGCCATTGGCATCTCCCTGGCAATATGGCTGC
TGATTCTGCTGGTCACCATCCCTTTGTATGTCGTGAAGCAGACCATCTTCATTCCTGCCCT
GAACATCACGACCTGTCATGATGTTTTGCCTGAGCAGCTCTTGGTGGGAGACATGTTCAA
TTACTTCCTCTCTCTGGCCATTGGGGTCTTTCTGTTCCCAGCCTTCCTCACAGCCTCTGCC
TATGTGCTGATGATCAGAATGCTGCGATCTTCTGCCATGGATGAAAACTCAGAGAAGAAA
AGGAAGAGGGCCATCAAACTCATTGTCACTGTCCTGGCCATGTACCTGATCTGCTTCACT
CCTAGTAACCTTCTGCTTGTGGTGCATTATTTTCTGATTAAGAGCCAGGGCCAGAGCCAT
GTCTATGCCCTGTACATTGTAGCCCTCTGCCTCTCTACCCTTAACAGCTGCATCGACCCCT
TTGTCTATTACTTTGTTTCACATGATTTCAGGGATCATGCAAAGAACGCTCTCCTTTGCCG
AAGTGTCCGCACTGTAAAGCAGATGCAAGTATCCCTCACCTCAAAGAAACACTCCAGGAA
ATCCAGCTCTTACTCTTCAAGTTCAACCACTGTTAAGACCTCCTATTGA

DIAGNOSTIC AND SCREENING METHODS FOR ATOPIC DERMATITIS

CROSS-REFERENCE

This application claims the benefit of U.S. Provisional Patent Application No. 61/885,972, filed Oct. 2, 2013, which application is incorporated herein by reference in its entirety.

STATEMENT REGARDING FEDERALLY SPONSORED RESEARCH

This invention was made with government support under Grant Nos. AR059385 and DOD007123A awarded by the National Institutes of Health. The government has certain rights in the invention.

INTRODUCTION

Atopic dermatitis (AD) is a chronic itch and inflammatory disorder of the skin that affects one in ten people. AD is primarily characterized by intolerable and incurable itch. Up to 70% of AD patients go on to develop asthma in a process known as the "atopic march."

There is a need in the art for methods of identifying agents that are useful for treating atopic dermatitis. There is a need in the art for methods of diagnosing atopic dermatitis. There is a need in the art for methods and compositions for treating atopic dermatitis.

SUMMARY

The present disclosure provides methods for identifying agents that are candidate agents for treating atopic dermatitis. The present disclosure provides methods for diagnosing atopic dermatitis. The present disclosure provides compositions and methods for treating atopic dermatitis.

BRIEF DESCRIPTION OF THE DRAWINGS

FIGS. 1A-1F demonstrate that TSLP triggers robust itch behaviors in mice by activating sensory neurons.

FIGS. 2A-2C demonstrate that TSLP receptor components are expressed in sensory neurons.

FIGS. 5A-5B demonstrate that PAR2 activation promotes itch behaviors and $Ca^{2+}$ dependent release of TSLP.

FIGS. 6A-6G demonstrate that ORAI1 and STIM1 are required for PAR2- and TG-evoked $Ca^{2+}$ influx.

FIGS. 7A-7H demonstrate that PAR2 activation promotes $Ca^{2+}$-dependent NFAT translocation and TSLP secretion.

FIG. 8 depicts the human TSLPR protein (amino acid) and cDNA (nucleic acid) sequences. Top to bottom: SEQ ID NOs: 1, 2.

FIG. 9 depicts the human TSLPR protein (amino acid) and cDNA (nucleic acid) sequences. Top to bottom: SEQ ID NOs: 3, 4.

FIG. 10 depicts the human ORAI1 protein (amino acid) and cDNA (nucleic acid) sequences. Top to bottom: SEQ ID NOs: 5, 6.

FIG. 11 depicts the human ORAI2 protein (amino acid) and cDNA (nucleic acid) sequences. Top to bottom: SEQ ID NOs: 7, 8, 9, 10.

FIGS. 12A-12D depict the human STIM1 protein (amino acid) and cDNA (nucleic acid) sequences for isoforms 1-3. (A) Top to bottom: SEQ ID NOs: 11, 12, 13. (B) SEQ ID NO: 14. (C) SEQ ID NO: 15. (D) SEQ ID NO: 16.

FIG. 13 depicts the human TSLP protein (amino acid) and cDNA (nucleic acid) sequences. Top to bottom: SEQ ID NOs: 17, 18, 19, 20.

FIG. 14 depicts the human PAR2 protein (amino acid) and cDNA (nucleic acid) sequences. Top to bottom: SEQ ID NOs: 21, 22.

DEFINITIONS

Figure 3A:
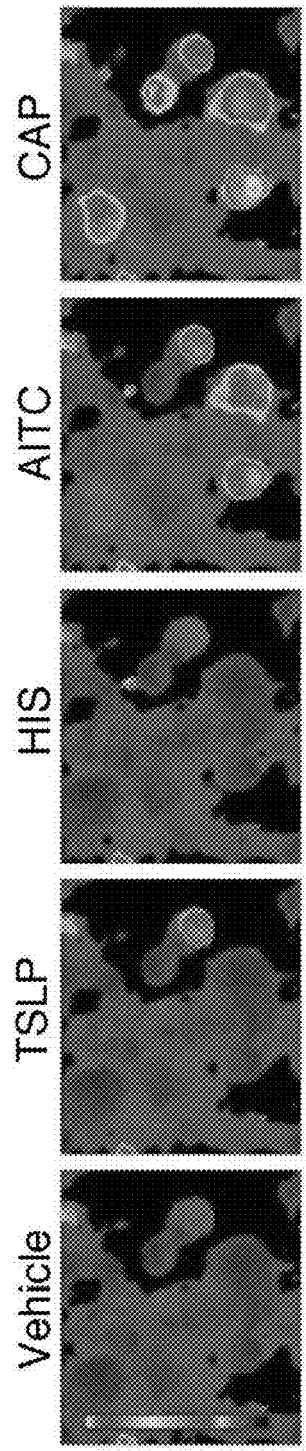
FIGS. 3A-3G demonstrate that TSLP directly activates a subset of sensory neurons.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense polynucleotide which is 18 nucleotides in length having 4 (four) noncomplementary nucleotides which are flanked by two regions of complete complementarity with the target nucleic acid would have 77.8% overall complementarity with the target nucleic acid. Percent complementarity of an oligomeric compound with a region of a target nucleic acid can be determined routinely using BLAST programs (basic local alignment search tools) and Power blast programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

The term "genetic modification" and refers to a permanent or transient genetic change induced in a cell following introduction of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

As used herein, the term "exogenous nucleic acid" refers to a nucleic acid that is not normally or naturally found in and/or produced by a cell in nature, and/or that is introduced into the cell (e.g., by electroporation, transfection, infection, lipofection, or any other means of introducing a nucleic acid into a cell).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, a human, a non-human primate, a rodent (e.g., a mouse, a rat, etc.), an ungulate, a canine, a lagomorph, a feline, etc. In some embodiments, a subject of interest is a human. In some embodiments, a subject is a non-human animal such as a rodent, or a lagomorph.

A "therapeutically effective amount" or "efficacious amount" means the amount of a compound, a nucleic acid, or a number of cells that, when administered to a subject for treating a disease, is sufficient to effect such treatment for the disease. The "therapeutically effective amount" will vary depending on the compound or the cell, the disease and its severity and the age, weight, etc., of the subject to be treated.

A "biological sample" encompasses a variety of sample types obtained from an individual and can be used in a diagnostic assay. The definition encompasses a skin biopsy or tissue cultures or cells derived therefrom and the progeny thereof. The definition also includes samples that have been manipulated in any way after their procurement, such as by treatment with reagents, solubilization, or enrichment for certain components, such as polypeptides and/or nucleic acids. A biological sample can be fresh, or can be frozen or otherwise treated. In some embodiments, a biological sample may include compounds which are not naturally intermixed with the sample in nature such as preservatives, anticoagulants, buffers, fixatives, nutrients, antibiotics, and the like. In some embodiments, a biological sample may include compounds which are not naturally intermixed with the sample in nature such as preservatives, anticoagulants, buffers, fixatives, nutrients, antibiotics, or the like The term "biological sample" encompasses a clinical sample, and also includes cells in culture, cell supernatants, cell lysates, biological fluid, and tissue samples.

"Isolated" refers to an entity of interest that is in an environment different from that in which the compound may naturally occur. "Isolated" is meant to include compounds that are within samples that are substantially enriched for the compound of interest and/or in which the compound of interest is partially or substantially purified.

By "purified" is meant a compound of interest (e.g., a nucleic acid agent; a polypeptide) has been separated from components that accompany it in nature. "Purified" can also be used to refer to a compound of interest separated from components that can accompany it during manufacture or preparation. In some embodiments, a compound is substantially pure when it is at least 50% to 60%, by weight, free from organic molecules with which it is naturally associated or with which it is associated during purification or synthesis. In some embodiments, the preparation is at least 85%, at least 90%, at least 95%, or at least 99%, by weight, of the compound of interest. Purity can be measured by any appropriate method, e.g., chromatography, mass spectroscopy, high performance liquid chromatography analysis, gel electrophoresis, an immunological method, fast protein liquid chromatography, etc.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, dyes, metal ions, metal sols, ligands (e.g., biotin, avidin, streptavidin, haptens, and the like), intercalating dyes, and the like. The term "fluorescer" refers to a substance or a portion thereof which is capable of exhibiting fluorescence in the detectable range.

The terms "polypeptide," "peptide," and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-59 is used.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a TSLP polypeptide" includes a plurality of such polypeptides and reference to "the nucleic acid agent" includes reference to one or more nucleic acid agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods for identifying agents that are candidate agents for treating atopic dermatitis. The present disclosure provides methods for diagnosing atopic dermatitis. The present disclosure provides compositions and methods for treating atopic dermatitis.

Screening Methods

The present disclosure provides methods for identifying agents that are candidate agents for treating atopic dermatitis. The methods are described below. The methods are also useful for identifying candidate agents for treating asthma, allergy, inflammatory bowel syndrome, or an inflammatory bowel disease. Although the description below focuses on identifying candidate agents for treating atopic dermatitis, it should be understood that the methods can also be used to identify candidate agents for treating asthma, allergy, inflammatory bowel syndrome, or an inflammatory bowel disease.

The present disclosure provides a method of identifying a candidate agent for treating atopic dermatitis, the method comprising: a) contacting a test agent in vitro with a cell expressing a Thymic Stromal Lymphopoietin (TSLPR) polypeptide and a Transient Receptor Potential Cation Channel, member A1 (TRPA1) polypeptide; and b) determining the effect of the test agent on coupling between TSLPR and TRPA1. A test agent that reduces coupling between TSLPR and TRPA1, compared to a control cell not contacted with the test agent, is considered a candidate agent for treating atopic dermatitis. In some cases, a reduction in coupling between TSLPR and TRPA1 is determined by assessing a reduction in intracellular calcium concentration. In some cases, assessing is carried out using a calcium-sensitive dye, wherein a test agent that reduces the intracellular concentration of calcium is considered a candidate agent for treating atopic dermatitis. In some cases, a reduction in coupling between TSLPR and TRPA1 is determined by assessing the effect of the agent on membrane depolarization, wherein a test agent that reduces membrane depolarization is considered a candidate agent for treating atopic dermatitis. In some cases, the cell is a keratinocyte. In some cases, the keratinocyte is a primary keratinocyte or a keratinocyte cell line. In some cases, the cell is a mammalian cell line genetically modified to express TSLPR and TRPA1.

The present disclosure provides a method of identifying a candidate agent for treating atopic dermatitis, the method comprising: a) contacting a test agent in vitro with a cell that expresses a PAR2 polypeptide and ORAI1 polypeptide; and b) assaying the level and/or localization of one or more of an ORAI1 gene product, a STIM1 gene product, and an NFAT1 gene product in the cell, wherein a test agent that reduces the level of one or more of an ORAI1 gene product, a STIM1 gene product, and an NFAT1 gene product in the cell and/or inhibits translocation of one or more of ORAI1, STIM1, and NFAT1 from the cytosol to the nucleus, compared to a control cell not contacted with the test agent, is considered a candidate agent for treating atopic dermatitis. In some cases, the cell is a keratinocyte. In some cases, the keratinocyte is a primary keratinocyte or a keratinocyte cell line. In some cases, the cell is a mammalian cell line genetically modified to express a PAR2 polypeptide and ORAI1 polypeptide. In some cases, the gene product is an mRNA, and wherein the level of the mRNA is determined by a quantitative polymerase chain reaction. In some cases, the gene product is a polypeptide, and wherein the level of the polypeptide is determined using an immunological assay. In some cases, an effect on the level of the one or more of an ORAI1 gene product, a STIM1 gene product, and an NFAT1 gene product in the cell is determined by assaying the level of TSLP produced by the cell.

The present disclosure provides a method of identifying a candidate agent for treating atopic dermatitis, the method comprising: a) contacting a test agent in vitro with a cell that expresses a PAR2 polypeptide and ORAI1 polypeptide; and b) assaying the level of TSLP gene product produced by the cell, wherein a test agent that reduces the level of a TSLP gene product produced by the cell, compared to a control cell not contacted with the test agent, is considered a candidate agent for treating atopic dermatitis. In some cases, the cell is a keratinocyte. In some cases, the cell is a mammalian cell line genetically modified to express a PAR2 polypeptide and ORAI1 polypeptide. In some cases, the TSLP gene product is an mRNA, and wherein the level of the mRNA is determined by a quantitative polymerase chain reaction. In some cases, the TSLP gene product is a polypeptide, and wherein the level of the polypeptide is determined using an immunological assay.

The present disclosure provides a method of identifying a candidate agent for treating atopic dermatitis, the method comprising: a) contacting a TSLPR+ sensory neuron with a test agent; and b) determining the effect of the test agent on the activity of the sensory neuron, wherein a test agent that inhibits the activity of the sensory neuron, compared to a control cell not contacted with the test agent, is considered a candidate agent for treating atopic dermatitis. In some cases, the readout of activity is intracellular calcium concentration, wherein an agent that reduces intracellular calcium concentration, compared to a control cell not contacted with the test agent, is considered a candidate agent for treating atopic dermatitis. In some cases, the readout of activity is membrane depolarization, wherein a test agent that reduces membrane depolarization, compared to a control cell not contacted with the test agent, is considered a candidate agent for treating atopic dermatitis. In some cases, the effect of the test agent on activity of the sensory neuron is assessed using an electrophysiological assay.

Gene Products

Suitable gene products include nucleic acid gene products, e.g., mRNA. Suitable gene products include polypeptide gene products.

A "TSLPR nucleic acid gene product" encompasses a nucleic acid comprising a nucleotide sequence encoding polypeptide comprising any known TSLPR amino acid sequence, a fragment thereof (e.g., an active fragment thereof), or an ortholog thereof. The term "TSLPR nucleic acid gene product" further encompasses a nucleic acid comprising a nucleotide sequence having at least about 70%, at least about 75%, at least about 80%, at least about 85%, at least about 90%, at least about 95%, at least about 98%, or at least about 99% nucleotide sequence identity to the TSLPR nucleotide sequence depicted in FIG. 8. Also encompassed are nucleic acids comprising nucleotide sequences encoding TSLPR fusion proteins.

A "TSLPR polypeptide" encompasses a polypeptide comprising an amino acid sequence having at least about 70%, at least about 75%, at least about 80%, at least about 85%, at least about 90%, at least about 95%, at least about 98%, or at least about 99% amino acid sequence identity to the TSLPR amino acid sequence depicted in FIG. 8. Also encompassed are TSLPR fusion proteins.

A "TRPA1 nucleic acid gene product" encompasses a nucleic acid comprising a nucleotide sequence encoding polypeptide comprising any known TRPA1 amino acid sequence, a fragment thereof (e.g., an active fragment thereof), or an ortholog thereof. The term "TRPA1 nucleic acid gene product" further encompasses a nucleic acid comprising a nucleotide sequence having at least about 70%, at least about 75%, at least about 80%, at least about 85%, at least about 90%, at least about 95%, at least about 98%, or at least about 99% nucleotide sequence identity to the TRPA1 nucleotide sequence depicted in FIG. 9. Also encompassed are nucleic acids comprising nucleotide sequences encoding TRPA1 fusion proteins.

A "TRPA1 polypeptide" encompasses a polypeptide comprising an amino acid sequence having at least about 70%, at least about 75%, at least about 80%, at least about 85%, at least about 90%, at least about 95%, at least about 98%, or at least about 99% amino acid sequence identity to the TRPA1 amino acid sequence depicted in FIG. 8. Also encompassed are TRPA1 fusion proteins.

An "ORAI1 nucleic acid gene product" encompasses a nucleic acid comprising a nucleotide sequence encoding polypeptide comprising any known ORAI1 amino acid sequence, a fragment thereof (e.g., an active fragment thereof), or an ortholog thereof. The term "ORAI1 nucleic acid gene product" further encompasses a nucleic acid comprising a nucleotide sequence having at least about 70%, at least about 75%, at least about 80%, at least about 85%, at least about 90%, at least about 95%, at least about 98%, or at least about 99% nucleotide sequence identity to the ORAI1 nucleotide sequence depicted in FIG. 10. Also encompassed are nucleic acids comprising nucleotide sequences encoding ORAI1 fusion proteins.

An "ORAI1 polypeptide" encompasses a polypeptide comprising an amino acid sequence having at least about 70%, at least about 75%, at least about 80%, at least about 85%, at least about 90%, at least about 95%, at least about 98%, or at least about 99% amino acid sequence identity to the ORAI1 amino acid sequence depicted in FIG. 10. Also encompassed are ORAI1 fusion proteins.

A "STIM1 nucleic acid gene product" encompasses a nucleic acid comprising a nucleotide sequence encoding polypeptide comprising any known STIM1 amino acid sequence, a fragment thereof (e.g., an active fragment thereof), or an ortholog thereof. The term "STIM1 nucleic acid gene product" further encompasses a nucleic acid comprising a nucleotide sequence having at least about 70%, at least about 75%, at least about 80%, at least about 85%, at least about 90%, at least about 95%, at least about 98%, or at least about 99% nucleotide sequence identity to the STIM1 nucleotide sequence depicted in one of FIGS. 12B-D. Also encompassed are nucleic acids comprising nucleotide sequences encoding STIM1 fusion proteins.

A "STIM1 polypeptide" encompasses a polypeptide comprising an amino acid sequence having at least about 70%, at least about 75%, at least about 80%, at least about 85%, at least about 90%, at least about 95%, at least about 98%, or at least about 99% amino acid sequence identity to the STIM1 amino acid sequence depicted in FIG. 12A. Also encompassed are STIM1 fusion proteins.

A "PAR2 nucleic acid gene product" encompasses a nucleic acid comprising a nucleotide sequence encoding polypeptide comprising any known PAR2 amino acid sequence, a fragment thereof (e.g., an active fragment thereof), or an ortholog thereof. The term "PAR2 nucleic acid gene product" further encompasses a nucleic acid comprising a nucleotide sequence having at least about 70%, at least about 75%, at least about 80%, at least about 85%, at least about 90%, at least about 95%, at least about 98%, or at least about 99% nucleotide sequence identity to the PAR2 nucleotide sequence depicted in FIG. 14. Also encompassed are nucleic acids comprising nucleotide sequences encoding PAR2 fusion proteins.

A "PAR2 polypeptide" encompasses a polypeptide comprising an amino acid sequence having at least about 70%, at least about 75%, at least about 80%, at least about 85%, at least about 90%, at least about 95%, at least about 98%, or at least about 99% amino acid sequence identity to the PAR2 amino acid sequence depicted in FIG. 14. Also encompassed are PAR2 fusion proteins.

A "TSLP nucleic acid gene product" encompasses a nucleic acid comprising a nucleotide sequence encoding polypeptide comprising any known TSLP amino acid sequence, a fragment thereof (e.g., an active fragment thereof), or an ortholog thereof. The term "TSLP nucleic acid gene product" further encompasses a nucleic acid comprising a nucleotide sequence having at least about 70%, at least about 75%, at least about 80%, at least about 85%, at least about 90%, at least about 95%, at least about 98%, or at least about 99% nucleotide sequence identity to the TSLP nucleotide sequence depicted in FIG. 13. Also encompassed are nucleic acids comprising nucleotide sequences encoding TSLP fusion proteins.

A "TSLP polypeptide" encompasses a polypeptide comprising an amino acid sequence having at least about 70%, at least about 75%, at least about 80%, at least about 85%, at least about 90%, at least about 95%, at least about 98%, or at least about 99% amino acid sequence identity to the TSLP amino acid sequence depicted in FIG. 13. Also encompassed are TSLP fusion proteins.

In some embodiments, a gene product is a polypeptide that is a fusion protein comprising a marker polypeptide and a fusion partner polypeptide such as a fluorescent or chromogenic polypeptide, or an enzyme that generates a product that produces a detectable signal. Suitable enzymes include, but are not limited to, β-galactosidase luciferase, horse radish peroxidase, alkaline phosphatase, etc. Suitable fluorescent proteins include, but are not limited to, a green fluorescent protein (GFP), including, but not limited to, a GFP derived from *Aequoria victoria* or a derivative thereof, a number of which are commercially available; a GFP from a species such as *Renilla reniformis, Renilla mulleri*, or *Ptilosarcus guernyi*, as described in, e.g., WO 99/49019 and Peelle et al. (2001) *J. Protein Chem.* 20:507-519; a yellow fluorescent protein; a red fluorescent protein; mCherry; any of a variety of fluorescent and colored proteins from *Anthozoan* species, as described in, e.g., Matz et al. (1999) *Nature Biotechnol.* 17:969-973, U.S. Patent Publication No. 2002/0197676, or U.S. Patent Publication No. 2005/0032085; and the like.

Cells

Cells that produce a TSLPR and a TRPA1 gene product and that are suitable for use in a subject screening method include mammalian cells that normally produce a TSLPR and a TRPA1 gene product, and mammalian cells that are genetically modified to produce a TSLPR and a TRPA1 gene product (e.g., cells that are genetically modified with a nucleic acid comprising a nucleotide sequence encoding a TSLPR and a TRPA1 gene product, where expression of the nucleic acid results in production of the TSLPR and the TRPA1 gene product in the genetically modified cell). Suitable cells include, e.g., primary keratinocytes; a keratinocyte cell line (e.g., HaCaT cell line); and a mammalian cell line. In some cases, a suitable cell is a primary sensory neuron, e.g., a TSLPR$^+$ sensory neuron; a PC12 cell (e.g., ATCC CRL-1721); an N2A cell (e.g., ATCC CCL-131); an F11 cell; and the like.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Test Agents

By "test agent," "candidate agent," and grammatical equivalents herein, which terms are used interchangeably herein, is meant any molecule (e.g. proteins (which herein includes proteins, polypeptides, and peptides), small (i.e., 5-1000 Da, 100-750 Da, 200-500 Da, or less than 500 Da in size), or organic or inorganic molecules, polysaccharides, polynucleotides, etc.) which are to be tested for activity in a subject assay.

A variety of different candidate agents may be screened by the above methods. Candidate agents encompass numerous chemical classes, e.g., small organic compounds having a molecular weight of more than 50 daltons (e.g., at least about 50 Da, at least about 100 Da, at least about 150 Da, at least about 200 Da, at least about 250 Da, or at least about 500 Da) and less than about 20,000 daltons, less than about 10,000 daltons, less than about 5,000 daltons, or less than about 2,500 daltons. For example, in some embodiments, a suitable candidate agent is an organic compound having a molecular weight in a range of from about 500 Da to about 20,000 Da, e.g., from about 500 Da to about 1000 Da, from about 1000 Da to about 2000 Da, from about 2000 Da to about 2500 Da, from about 2500 Da to about 5000 Da, from about 5000 Da to about 10,000 Da, or from about 10,000 Da to about 20,000 Da.

Candidate agents can comprise functional groups necessary for structural interaction with proteins, e.g., hydrogen bonding, and can include at least an amine, carbonyl, hydroxyl or carboxyl group, or at least two of the functional chemical groups. The candidate agents can comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Moreover, screening may be directed to known pharmacologically active compounds and chemical analogs thereof, or to new agents with unknown properties such as those created through rational drug design.

In one embodiment, candidate modulators are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

In another embodiment, the candidate agents are provided as libraries of natural compounds in the form of bacterial, fungal, plant and animal extracts that are available or readily produced. Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In one embodiment, candidate agents include proteins (including antibodies, antibody fragments (i.e., a fragment containing an antigen-binding region, single chain antibodies, and the like), nucleic acids, and chemical moieties. In one embodiment, the candidate agents are naturally occurring proteins or fragments of naturally occurring proteins. Thus, for example, cellular extracts containing proteins, or random or directed digests of proteinaceous cellular extracts, may be tested. In this way libraries of prokaryotic and eukaryotic proteins may be made for screening. Other embodiments include libraries of bacterial, fungal, viral, and mammalian proteins (e.g., human proteins).

In one embodiment, the candidate agents are organic moieties. In this embodiment, as is generally described in WO 94/243 14, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested.

In some embodiments, known agents, including agents disclosed in the Examples, are specifically excluded. For example, in some cases, histamine, chloroquine, BAM8-22 (Val-Gly-Arg-Pro-Glu-Trp-Trp-Met-Asp-Tyr-Gln-Lys-Arg-Tyr-Gly) (SEQ ID NO: 23), U73122 (1-[6-[[(17β)-3-Methoxyestra-1,3,5(10)-trien-17-yl]amino]hexyl]-1H-pyrrole-2,5-dione), thapsigargin, and SLIGRL (Ser-Leu-Ile-Gly-Arg-Leu) (SEQ ID NO: 24) are excluded as test agents.

As used herein, the term "determining" refers to both quantitative and qualitative determinations and as such, the term "determining" is used interchangeably herein with "assaying," "measuring," and the like.

The assay can include one or more additional reagents. These include reagents like salts, neutral proteins, e.g. albumin, detergents, etc., including agents that are used to facilitate optimal enzyme activity and/or reduce non-specific or background activity. Reagents that improve the efficiency of the assay, such as protease inhibitors, anti-microbial agents, etc. may be used. The components of the assay mixture are added in any order that provides for the requisite activity. Incubations are performed at any suitable temperature, e.g., between 4° C. and 40° C. Incubation periods are selected for optimum activity, but may also be optimized to facilitate rapid high-throughput screening. Typically between 0.1 hour and 1 hour will be sufficient.

Assays of the present disclosure include controls, where suitable controls include a cell not contacted with the test agent. Generally a plurality of assay mixtures is run in parallel with different agent concentrations to obtain a differential response to the various concentrations. Typically, one of these concentrations serves as a negative control, i.e. at zero concentration or below the level of detection.

A candidate agent is assessed for any cytotoxic activity (other than anti-proliferative activity) it may exhibit toward a living eukaryotic cell, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

Assaying a Level of Nucleic Acid Gene Product

In some embodiments, a subject screening method involves determining the level of a nucleic acid gene product. Nucleic acid gene products include mRNA; a cDNA copy of a mRNA; etc. Suitable methods for detecting the level of a nucleic acid in a cell include nucleic acid hybridization methods and/or nucleic acid amplification methods. For example, nucleic acid hybridization can be carried out using a nucleic acid probe that detects an mRNA in a cell, or a cDNA copy of an mRNA. Nucleic acid amplification methods can be carried out using nucleic acid primers that specifically amplify a particular mRNA (or a cDNA copy of the mRNA). In some embodiments, nucleic acid amplification using gene-specific primers is followed by nucleic acid hybridization using a specific probe. In some cases, a quantitative polymerase chain reaction (qPCR) is used.

Assaying the Level of a Polypeptide

In some embodiments, a subject method involves detecting the level of a polypeptide gene product. Suitable methods for detecting the level of a polypeptide include immunological assays, e.g., an enzyme-linked immunosorbent assay, a radioimmunoassay, an immunoprecipitation assay, a protein ("Western") blot; assays that detect a fusion partner of a fusion protein; and the like.

In some embodiments, an immunological assay involves use of an antibody specific for a polypeptide. The antibody can include a detectable label. The antibody will in some embodiments be detectably labeled, e.g., with a radioisotope, an enzyme which generates a detectable product, a fluorescent protein, a chromogenic protein, and the like. An antibody can be further conjugated to other moieties, such as members of specific binding pairs, e.g., biotin (member of biotin-avidin specific binding pair), and the like. An antibody can also be bound to a solid support, including, but not limited to, polystyrene plates or beads, magnetic beads, test strips, membranes, and the like.

In some embodiments, the antibody is detectably labeled, either directly or indirectly. Direct labels include radioisotopes (e.g., $^{125}$I; $^{35}$S, and the like); enzymes whose products are detectable (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; and the like. Indirect labels include second antibodies specific for a gene product-specific antibody, wherein the second antibody is labeled as described above; and members of specific binding pairs, e.g., biotin-avidin, and the like.

In some embodiments, an antibody comprises, covalently linked to the antibody, a protein that provides for a detectable signal. Suitable proteins include, but are not limited to, fluorescent proteins and enzymes (e.g., (β-galactosidase, luciferase, horse radish peroxidase, alkaline phosphatase, etc.). Suitable fluorescent proteins include, but are not limited to, a green fluorescent protein (GFP), including, but not limited to, a GFP derived from *Aequoria victoria* or a derivative thereof, a number of which are commercially available; a GFP from a species such as *Renilla reniformis*, *Renilla mulleri*, or *Ptilosarcus guernyi*, as described in, e.g., WO 99/49019 and Peelle et al. (2001) *J. Protein Chem.* 20:507-519; a yellow fluorescent protein; a blue fluorescent protein; a red fluorescent protein; any of a variety of fluorescent and colored proteins from *Anthozoan* species, as described in, e.g., Matz et al. (1999) *Nature Biotechnol.* 17:969-973, U.S. Patent Publication No. 2002/0197676, or U.S. Patent Publication No. 2005/0032085; and the like.

Assaying Intracellular Calcium Ion Concentration

In some embodiments, a subject method involves determining the intracellular calcium ion concentration ($[Ca^{2+}]_i$) in a cell. The intracellular calcium ion concentration in a cell can be determined using a calcium-sensing dye.

Suitable intracellular $Ca^{2+}$ ion-detecting dyes include, but are not limited to, fura-2, bis-fura 2, indo-1, Quin-2, Quin-2 AM, Benzothiaza-1, Benzothiaza-2, indo-5F, Fura-FF, BTC, Mag-Fura-2, Mag-Fura-5, Mag-Indo-1, fluo-3, rhod-2, fura-4F, fura-5F, fura-6F, fluo-4, fluo-5F, fluo-5N, Oregon Green 488 BAPTA, Calcium Green, Calcein, Fura-C18, Calcium Green-C18, Calcium Orange, Calcium Crimson, Calcium Green-5N, Magnesium Green, Oregon Green 488 BAPTA-1, Oregon Green 488 BAPTA-2, X-rhod-1, Fura Red, Rhod-5F, Rhod-5N, X-Rhod-5N, Mag-Rhod-2, Mag-X-Rhod-1, Fluo-5N, Fluo-5F, Fluo-4FF, Mag-Fluo-4, Aequorin, dextran conjugates or any other derivatives of any of these dyes, and others (see, e.g., the catalog or Internet site for Molecular Probes, Eugene, see, also, Nuccitelli, ed., Methods in Cell Biology, Volume 40: A Practical Guide to the Study of Calcium in Living Cells, Academic Press (1994); Lambert, ed., Calcium Signaling Protocols (Methods in Molecular Biology Volume 114), Humana Press (1999); W. T. Mason, ed., Fluorescent and Luminescent Probes for Biological Activity. A Practical Guide to Technology for Quantitative Real-Time Analysis, Second Ed, Academic Press (1999); Calcium Signaling Protocols (Methods in Molecular Biology), 2005, D. G. Lamber, ed., Humana Press).

Assaying Voltage Changes

In some embodiments, a subject method involves determining the effect of a test agent on membrane voltage. Changes in membrane voltage can be determined using voltage-sensitive dyes.

Suitable voltage-sensitive dyes include, but are not limited to, merocyanine-oxazolone dyes (e.g., NK2367); merocyanine-rhodanine dyes (e.g., NK2495, NK2761, NK2776, NK3224, and NK3225); oxonol dyes (e.g., RH155, RH479, RH482, RH1691, RH1692, and RH1838); styryl dyes (e.g., RH237, RH414, RH421, RH437, RH461, RH795, JPW 1063, JPW3028, di-4-ANEPPS, di-9-ANEPPS, di-2-ANEPEQ, di-12-ANEPEQ, di-8-ANEPPQ, and di-12-ANEPPQ); and the like.

Determining Electrophysiological Changes

In some embodiments, a subject method involves determining the effect of a test agent on electrophysiology of a cell. Electrophysiological changes can be determined using any known method including, e.g., a standard patch clamp method.

Diagnostic Methods

The present disclosure provides methods for diagnosing atopic dermatitis. The methods described below for diagnosing atopic dermatitis can also be used to diagnose asthma, allergy, inflammatory bowel syndrome, or an inflammatory bowel disease. Thus, although the description below focuses on methods for diagnosing atopic dermatitis, the methods can also be used to diagnose asthma, allergy, inflammatory bowel syndrome, or an inflammatory bowel disease. Where a subject method is used to diagnose asthma, allergy, inflammatory bowel syndrome, or an inflammatory bowel disease, the sample that is assayed will be one appropriate to asthma, allergy, inflammatory bowel syndrome, or an inflammatory bowel disease. For example, the biological sample can be lung tissue, bronchoalveolar lavage, a bowel biopsy sample, and the like.

The present disclosure provides a method of diagnosing atopic dermatitis in an individual, the method comprising assaying the level of a gene product of one or more of ORAI1, STIM1, and NFAT in a keratinocyte present in a skin sample obtained from the individual, wherein an elevated level of a gene product of one or more of ORAI1, STIM1, and NFAT in the keratinocyte, compared to a normal control level, indicates that the individual has atopic dermatitis.

The present disclosure provides a method of diagnosing atopic dermatitis in an individual, the method comprising: assaying the level of Substance P and/or CGRP (Calcitonin Gene-Related Peptide; acdtatcvth rlagllsrsg gvvknnfvpt nvgskaf) (SEQ ID NO: 25) in a skin sample obtained from the individual, wherein an elevated level of Substance P and/or CGRP in the skin sample, compared to a normal control level, indicates that the individual has atopic dermatitis.

The present disclosure provides a method of diagnosing atopic dermatitis in an individual, the method comprising: determining a subcellular localization of one or more of ORAI1, STIM1, and NFAT in a keratinocyte present in a skin sample obtained from the individual, wherein a clustering of one or more of ORAI1, STIM1, and NFAT in the keratinocyte indicates that the individual has atopic dermatitis.

Control Values

Levels of a gene product in a biological sample obtained from a test subject are compared to a normal control value(s) or range of normal control values. The control value can be based on levels of the gene product in comparable samples (e.g., blood, plasma, or serum sample, or other biological sample) obtained from a control population, e.g., the general population or a select population of human subjects. For example, the select population may be comprised of apparently healthy subjects, e.g., individuals who have not previously had any signs or symptoms of atopic dermatitis. Apparently healthy individuals also generally do not otherwise exhibit symptoms of disease. In other words, such individuals, if examined by a medical professional, would be characterized as healthy and free of symptoms of disease.

The control value can take a variety of forms. The control value can be a single cut-off value, such as a median or mean. A normal control value can be a normal control range.

Subjects

Individuals who are to be tested using a method of the present disclosure include individuals who have never previously been diagnosed as having atopic dermatitis.

Generating a Report

A subject method can include generating a report that provides an indication of the likelihood that an individual has atopic dermatitis.

In some embodiments, a subject method of diagnosing atopic dermatitis involves generating a report. Such a report can include information such as the likelihood that the individual has atopic dermatitis; a recommendation regarding further evaluation; a recommendation regarding therapeutic drug intervention; and the like.

For example, the methods disclosed herein can further include a step of generating or outputting a report providing the results of a subject diagnostic method, which report can be provided in the form of an electronic medium (e.g., an electronic display on a computer monitor), or in the form of a tangible medium (e.g., a report printed on paper or other tangible medium). An assessment as to the likelihood can be referred to as a "risk report" or, simply, "risk score." A person or entity that prepares a report ("report generator") may also perform steps such as sample gathering, sample processing, and the like. Alternatively, an entity other than the report generator can perform steps such as sample gathering, sample processing, and the like. A risk assessment report can be provided to a user. A "user" can be a health professional (e.g., a clinician, a laboratory technician, a physician (e.g., a cardiologist), etc.).

A subject report can further include one or more of: 1) service provider information; 2) patient data; 3) data regarding the level of a marker (e.g., ORAI1; STIM1; etc.); 4) follow-up evaluation recommendations; 5) therapeutic intervention recommendations; and 6) other features.

Further Evaluation

Based on detection of a level a gene product, as described above, and/or based on a report (as described above), a physician or other qualified medical personnel can determine whether further evaluation of the test subject (the patient) is require. Further evaluation can include, e.g., tests for allergic reactions; tests for inflammation; and the like.

Therapeutic Intervention

Based on detection of a level of a gene product, and/or based on a report (as described above), a physician or other qualified medical personnel can determine whether appropriate therapeutic intervention is advised, e.g., in order to treat atopic dermatitis.

Therapeutic intervention includes drug-based therapeutic intervention, such as an anti-inflammatory agent, a corticosteroid, and the like.

Nucleic Acid Agents

The present disclosure provides nucleic acid agents (e.g., antisense nucleic acids, siRNA, etc.) nucleic acids encoding the nucleic acid agents, and composition comprising the nucleic acid agents, where a subject nucleic acid agents is effective to reduce the level of an ORAI1 gene produce or a STIM1 gene product in a cell (e.g., a keratinocyte). In some embodiments, a subject nucleic acid agent comprises a nucleotide sequence capable of hybridizing to an ORAI1 mRNA. In some embodiments, a subject nucleic acid agent comprises a nucleotide sequence capable of hybridizing to a STIM1 mRNA.

In some embodiments, a subject nucleic acid agent reduces the level of an ORAI1 gene product in a keratinocyte by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more than 90%, compared to the level of the ORAI1 gene product in the keratinocyte cell in the absence of the nucleic acid agent.

In some embodiments, a subject nucleic acid agent reduces the level of a STIM1 gene product in a keratinocyte by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more than 90%, compared to the level of the STIM1 gene produce in the absence of the nucleic acid agent.

A STIM1 nucleic acid comprises a nucleotide sequence having at least about 75%, at least about 80%, at least about 85%, at least about 90%, at least about 95%, at least about 98%, at least about 99%, or 100%, nucleotide sequence identity to the nucleotide sequence depicted in one of FIGS. 12B-D.

A ORAI1 nucleic acid comprises a nucleotide sequence having at least about 75%, at least about 80%, at least about 85%, at least about 90%, at least about 95%, at least about 98%, at least about 99%, or 100%, nucleotide sequence identity to the nucleotide sequence depicted in FIG. 10.

The portion of a subject nucleic acid that hybridizes with an ORAI1 mRNA or a STIM1 mRNA has a length of from about 18 nucleotides to about 50 nucleotides (nt). For example, a subject antisense nucleic acid can have a length of from about 18 nt to about 50 nt. One having ordinary skill in the art will appreciate that this embodies antisense nucleic acids having a length of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

The total length of a subject antisense nucleic acid can be greater than the duplex-forming portion, e.g., the total length of a subject antisense nucleic acid can be from about 20 nucleotides (nt) to about 30 nt, from about 30 nt to about 40 nt, from about 40 nt to about 50 nt, from about 50 nt to about 75 nt, from about 75 nt to about 100 nt, from about 100 nt to about 125 nt, from about 125 nt to about 150 nt, from about 150 nt to about 175 nt, or from about 175 nt to about 200 nt, or greater than 200 nt, in length.

Interfering Nucleic Acids

Suitable agents that reduce the level of an ORAI gene product or a STIM1 gene product in a cell include interfering nucleic acids, e.g., interfering RNA molecules. In one embodiment, reduction of an ORAI gene product or a STIM1 gene product level is accomplished through RNA interference (RNAi) by contacting a cell with a small nucleic acid molecule, such as a short interfering nucleic acid (siNA), a short interfering RNA (siRNA), a double-stranded RNA (dsRNA), a micro-RNA (miRNA), or a short hairpin RNA (shRNA) molecule, or modulation of expression of a small interfering RNA (siRNA) so as to provide for decreased levels of an ORAI gene product or a STIM1 gene product.

Interfering nucleic acids can be designed based on the nucleotide sequence of an ORAI1- or a STIM1-encoding nucleotide sequence. For example, in some embodiments, an ORAI1-encoding nucleotide sequence as set forth in FIG. 10, or a nucleotide sequence having at least 90%, at least 95%, at least 98%, or at least 99%, nucleotide sequence identity to the ORAI1 nucleotide sequence depicted in FIG. 10, is used to design an interfering nucleic acid. For example, in some embodiments, a STIM1-encoding nucleotide sequence as set forth in one of FIGS. 12B-D, or a nucleotide sequence having at least 90%, at least 95%, at least 98%, or at least 99%, nucleotide sequence identity to the STIM1 nucleotide sequence depicted in one of FIGS. 12B-D, is used to design an interfering nucleic acid.

The term "short interfering nucleic acid," "siNA," "short interfering RNA," "siRNA," "short interfering nucleic acid molecule," "short interfering oligonucleotide molecule," or "chemically-modified short interfering nucleic acid molecule" as used herein refers to any nucleic acid molecule capable of inhibiting or down regulating gene expression, for example by mediating RNA interference "RNAi" or gene silencing in a sequence-specific manner. Design of RNAi molecules when given a target gene is routine in the art. See also US 2005/0282188 (which is incorporated herein by reference) as well as references cited therein. See, e.g., Pushparaj et al. Clin Exp Pharmacol Physiol. 2006 May-June; 33(5-6):504-10; Lutzelberger et al. Handb Exp Pharmacol. 2006; (173):243-59; Aronin et al. Gene Ther. 2006 March; 13(6):509-16; Xie et al. Drug Discov Today. 2006 January; 11(1-2):67-73; Grunweller et al. Curr Med Chem. 2005; 12(26):3143-61; and Pekaraik et al. Brain Res Bull. 2005 Dec. 15; 68(1-2):115-20. Epub 2005 Sep. 9.

Methods for design and production of siRNAs to a desired target are known in the art, and their application to ORAI1 or STIM1 genes for the purposes disclosed herein will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US 2002/0120129, each of which are incorporated herein by reference.

Publicly available tools to facilitate design of siRNAs are available in the art. See, e.g., DEQOR: Design and Quality Control of RNAi (available on the internet at cluster-1.mpi-cbg.de/Deqor/deqor.html). See also, Henschel et al. Nucleic Acids Res. 2004 Jul. 1; 32(Web Server issue):W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand generally comprises nucleotide sequence that is complementary to nucleotide sequence in the other strand; such as where the antisense strand and sense strand form a duplex or double stranded structure, for example wherein the double stranded region is about 15 base pairs to about 30 base pairs, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 nucleotides to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules lack 2'-hydroxy (2'-OH) containing nucleotides. siNAs do not necessarily require the presence of nucleotides having a 2'-hydroxy group for mediating RNAi and as such, siNA molecules optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules can be used to epigenetically silence a target gene at both the post-transcriptional level or the pre-transcriptional level. In a non-limiting example, epigenetic regulation of gene expression by siNA molecules can result from siNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

siNA molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, for example, two regions of a target nucleic acid (e.g., ORAI1; STIM1).

siNA molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162;

Sproat, U.S. Pat. No. 5,334,711; Gold et al., U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334, 711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Eamshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; each of which are hereby incorporated in their totality by reference herein). In view of such teachings, similar modifications can be used as described herein to modify the siNA nucleic acid molecules of disclosed herein so long as the ability of siNA to promote RNAi is cells is not significantly inhibited.

Short interfering nucleic acid (siNA) molecules having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, Nucleic Acids Res. 23, 2677; Caruthers et al., 1992, Methods in Enzymology 211, 3-19, incorporated by reference herein. In one embodiment, nucleic acid molecules include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, J. Am. Chem. Soc., 120, 8531-8532). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes includes those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine) In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

The present disclosure further provides a nucleic acid (including an expression vector) that comprises a nucleotide sequence that encodes a subject nucleic acid agent. Suitable expression vectors include, e.g., a viral vector. In some embodiments, the nucleic acid agent-encoding nucleotide sequence is operably linked to a keratinocyte-specific promoter. In some embodiments, the nucleic acid agent-encoding nucleotide sequence is operably linked to an inducible promoter. In the discussion herein relating to compositions comprising, and methods involving use of, a nucleic acid agent, it should be understood that the present disclosure contemplates compositions comprising a nucleic acid comprising a nucleotide sequence that encodes a subject nucleic acid agent, and methods involving use of a nucleic acid comprising a nucleotide sequence that encodes a subject nucleic acid agent.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Modifications

In some embodiments, a subject nucleic acid (e.g., an siRNA; an antisense nucleic acid) comprises one or more modifications, e.g., a base modification, a backbone modification, etc. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable modifications include modified backbones or non-natural internucleoside linkages. Nucleic acids (e.g., a subject siRNA; a subject antisense nucleic acid) having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3',5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid (e.g., a subject siRNA; a subject antisense nucleic acid) comprises one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids (e.g., a subject siRNA; a subject antisense nucleic acid) having morpholino backbone structures as described in, e.g., U.S. Pat. No. 5,034,506. For example, in some embodiments, a subject nucleic acid (e.g., a subject antisense nucleic acid; a subject synthetic target protector nucleic acid) comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A subject nucleic acid (e.g., a subject siRNA; a subject antisense nucleic acid) can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($-CH_2-$), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A subject nucleic acid (e.g., a subject siRNA; a subject antisense nucleic acid) can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nO(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—O $CH_2$ $CH_2$ $CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid (e.g., a subject siRNA; a subject antisense nucleic acid) may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound (e.g., an antisense nucleic acid; a target protector nucleic acid). These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Conjugates

Another possible modification of a subject nucleic acid (e.g., a subject siRNA; a subject antisense nucleic acid) involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject antisense nucleic acid or target protector nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.

Treatment Methods

The present disclosure provides compositions and methods for treating atopic dermatitis. The methods described below can also be used to treat asthma, allergy, inflammatory bowel syndrome, or an inflammatory bowel disease.

The present disclosure provides a method of treating atopic dermatitis in an individual, the method comprising administering to the individual an effective amount of one or both of: a) a nucleic acid agent that specifically reduces the level of ORAI1 in a keratinocyte in the individual; and b) a nucleic acid agent that specifically reduces the level of STIM1 in a keratinocyte in the individual, wherein reduction in the level of ORAI1 and/or STIM1 in a keratinocyte treats atopic dermatitis.

In some cases, an effective amount of a nucleic acid agent that specifically reduces the level of ORAI1 in a keratinocyte in the individual is an amount that, when administered in one or more doses to an individual in need thereof, as monotherapy or in combination therapy, is effective to ameliorate one or more symptoms of atopic dermatitis by at least about 10%, at least about 20%, at least about 30%, at least about 40%, at least about 50%, or more than 50%, compared to the degree or severity of the symptom in the individual in the absence of treatment with the nucleic acid agent.

In some cases, an effective amount of a nucleic acid agent that specifically reduces the level of STIM1 in a keratinocyte in the individual is an amount that, when administered in one or more doses to an individual in need thereof, as monotherapy or in combination therapy, is effective to ameliorate one or more symptoms of atopic dermatitis by at least about 10%, at least about 20%, at least about 30%, at least about 40%, at least about 50%, or more than 50%, compared to the degree or severity of the symptom in the individual in the absence of treatment with the nucleic acid agent.

In some cases, the nucleic acid agent is an antisense nucleic acid. In some cases, the nucleic acid agent is an siRNA, e.g., a short interfering RNA. In some cases, the nucleic acid agent comprises at least one modified nucleotide. In some cases, the modified nucleotide is a 2'-deoxy-2'-fluoro modified nucleotide, a 2'-deoxy-modified nucleotide, a locked nucleotide, an abasic nucleotide, a 2'-ammo-modified nucleotide, a 2"-alkyl-modified nucleotide, a morpholino nucleotide, a phosphoramidate, or a non-natural base comprising nucleotide. In some cases, at least one deoxyribose ring in the nucleic acid agent is substituted. In some cases, at least one deoxyribose ring in the nucleic acid agent is substituted with a 6-membered morpholine ring. In some cases, the nucleic acid agent comprises at least one substituted sugar moiety. In some cases, the nucleic acid agent is conjugated to a lipid moiety or to poly(L-lysine). In some cases, the nucleic acid agent comprises at least one nuclease-resistant internucleosidic linkage. In some cases, the internucleosidic linkage is selected from phosphorothioate, phosphorodithioate, phosphoramidate, phosphorodiamidate, methylphosphonate, P-chiral linkage, chiral phosphorothioate, phosphoroselenoate, phosphorodiselenoate, phosphoroanilothioate, phosphoranilidates, phosphotriester, aminoalkylphosphotriester, alkylphosphotriester, carbonate, carbamate, morpholino carbamate, 3'-thioformacetal, and silyl.

Compositions and Formulations

The present disclosure provides compositions, e.g., pharmaceutical compositions, comprising a subject nucleic acid agent (e.g., a subject siRNA; a subject antisense nucleic acid). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A subject composition can include: a) a subject nucleic acid; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl)amino-tris(hydroxymethyl) methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris (hydroxymethyl)-aminomethane (Tris), etc.). Suitable salts include, e.g., NaCl, $MgCl_2$, KCl, $MgSO_4$, etc.

A subject pharmaceutical formulation can include a subject target protector nucleic acid in an amount of from about 0.001% to about 90% (w/w). In the description of formulations, below, "subject nucleic acid" will be understood to include a subject synthetic target protector nucleic acid. For example, in some embodiments, a subject formulation comprises a subject target protector nucleic acid.

A subject nucleic acid can be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption.

A subject nucleic acid can encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of an active agent, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. For example, prodrug versions a subject nucleic acid can be prepared as SATE ((S acetyl-2-thioethyl) phosphate) derivatives according to the methods disclosed in WO 93/24510, WO 94/26764, and U.S. Pat. No. 5,770,713.

The term "pharmaceutically acceptable salts" refers to physiologically and pharmaceutically acceptable salts of a subject nucleic acid: i.e., salts that retain the desired biological activity of the parent compound and do not impart undesired toxicological effects thereto. For polynucleotides, suitable examples of pharmaceutically acceptable salts and their uses are further described in U.S. Pat. No. 6,287,860, which is incorporated herein by reference in its entirety.

The present disclosure also includes compositions and formulations, including pharmaceutical compositions and formulations, which include one or more of a subject nucleic acid agent. A subject composition can be administered in a number of ways depending upon whether local or systemic treatment is desired and upon the area to be treated. Administration can be systemic or local, e.g., where local administration includes topical (e.g., topically to the skin), intradermal, subcutaneous. Parenteral administration includes, but is not limited to, intravenous, intraarterial, subcutaneous, intraperitoneal, or intramuscular injection or infusion; or intracranial, e.g., intrathecal or intraventricular, administration. Nucleic acids with at least one 2'-O-methoxyethyl modification can be used for oral administration. Compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be necessary or desirable.

A subject formulation, which may conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

A subject composition can be formulated into any of many possible dosage forms such as, but not limited to, tablets, capsules, gel capsules, liquid syrups, soft gels, suppositories, and enemas. A subject composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A subject composition may include solutions, emulsions, foams and liposome-containing formulations. A subject composition or formulation can comprise one or more penetration enhancers, carriers, excipients, or other active or inactive ingredients.

Emulsions are typically heterogeneous systems of one liquid dispersed in another in the form of droplets, which can exceed 0.1 μm in diameter. Emulsions may contain additional components in addition to the dispersed phases, and the active agent (e.g., antisense polynucleotides) which can be present as a solution in the aqueous phase, the oily phase, or as a separate phase. Microemulsions are also suitable. Emulsions and their uses are well known in the art and are further described in U.S. Pat. No. 6,287,860.

A subject formulation can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and non-cationic liposomes can be used to deliver a subject nucleic acid.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions of the present disclosure may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

A subject nucleic acid can be conjugated to poly(L-lysine) to increase cell penetration. Such conjugates are described by Lemaitre et al., Proc. Natl. Acad. Sci. USA, 84, 648-652 (1987). The procedure requires that the 3'-terminal nucleotide be a ribonucleotide. The resulting aldehyde groups are then randomly coupled to the epsilon-amino groups of lysine residues of poly(L-lysine) by Schiff base formation, and then reduced with sodium cyanoborohydride.

One of skill in the art will recognize that formulations are routinely designed according to their intended use and/or route of administration.

Suitable formulations for topical administration include those in which a subject nucleic acid is in admixture with a topical delivery agent such as lipids, liposomes, fatty acids, fatty acid esters, steroids, chelating agents and surfactants. Suitable lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoyl-phosphatidyl ethanolamine DOTMA).

For topical or other administration, a subject nucleic acid can be encapsulated within liposomes or may form complexes thereto, in particular to cationic liposomes. Alternatively, a subject nucleic acid can be complexed to lipids, in particular to cationic lipids. Suitable fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanoiamine, N,N-dimethylacetamide, N,N-dimethylformamide, 2-pyrrolidone and derivatives thereof, tetrahydrofurfuryl alcohol, and AZONE™.

A subject nucleic acid agent can be delivered orally, in granular form including sprayed dried particles, or complexed to form micro or nanoparticles. Nucleic acid complexing agents and their uses are further described in U.S. Pat. No. 6,287,860.

Compositions and formulations for enteral or parenteral administration may include sterile aqueous solutions which may also contain buffers, diluents and other suitable additives such as, but not limited to, penetration enhancers, carrier compounds and other pharmaceutically acceptable carriers or excipients. In some cases, the formulation is one that is suitable for topical application to the skin.

Delivery and Routes of Administration

A subject nucleic acid agent can be administered by any suitable means. One skilled in the art will appreciate that many suitable methods of administering a subject nucleic acid agent to a host in the context of the present disclosure, in particular a human, are available, and, although more than one route may be used to administer a particular nucleic acid agent, a particular route of administration may provide a more immediate and more effective reaction than another route.

Suitable routes of administration include enteral and parenteral routes. Administration can be via a local or a systemic route of administration. A subject nucleic acid (e.g., a subject nucleic acid agent) can be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes, but is not limited to, intravenous, intraarterial, subcutaneous, intraperitoneal, or intramuscular injection or infusion; and intracranial, e.g., intrathecal or intraventricular, administration.

In some embodiments, a subject nucleic acid agent is administered topically to the skin. In other embodiments, a subject nucleic acid agent is administered intradermally. In other embodiments, a subject nucleic acid agent is administered subcutaneously.

Dosing

The formulation of therapeutic compositions and their subsequent administration (dosing) is within the skill of those in the art. Dosing is dependent on several criteria, including severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual nucleic acid agents, and can generally be estimated based on EC50s found to be effective in vitro and in vivo animal models.

For example, a suitable dose of a subject nucleic acid agent is from 0.01 µg to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 µg to 1 mg per kg of body weight. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein a subject nucleic acid agent is administered in maintenance doses, ranging from 0.01 µg to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 µg to 1 mg per kg of body weight.

In some embodiments, multiple doses of a subject nucleic acid (e.g., a subject nucleic acid agent) are administered. The frequency of administration of an active agent (a subject nucleic acid agent) can vary depending on any of a variety of factors, e.g., severity of the symptoms, etc. For example, in some embodiments, a subject nucleic acid (e.g., a subject nucleic acid agent) is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of an active agent (e.g., a subject nucleic acid agent), e.g., the period of time over which an active agent is administered, can vary, depending on any of a variety of factors, e.g., patient response, etc. For example, an active agent can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Combination Therapy

A subject method of treating atopic dermatitis can involve administering an agent (e.g., a subject nucleic acid agent), and can further involve administering at least a second therapeutic agent. For example, a subject method of treating atopic dermatitis can involve administering a subject nucleic acid agent, and can further involve administering at least a second therapeutic agent. Suitable second therapeutic agents include agents that treat atopic dermatitis include, e.g., anti-inflammatory agents; topical or oral corticosteroids (e.g., hydrocortisone; betamethasone; fluticasone); a calcineurin inhibitor (e.g., pimecrolimus; tacrolimus); an antihistamine (e.g., diphenhydramine; hydroxyzine; etc.); cyclosporine; interferon.

Subjects Suitable for Treatment

Subjects suitable for treatment with a subject method for treating atopic dermatitis include individuals who have been diagnosed as having atopic dermatitis; individuals who have atopic dermatitis, and who have failed treatment with an agent other than a subject nucleic acid agent; etc. In some cases, a subject suitable for treatment with a subject method has asthma, allergy, inflammatory bowel syndrome, or an inflammatory bowel disease.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

This example demonstrates the identification of the ORAI1/NFAT calcium signaling pathway as an essential regulator of TSLP release from keratinocytes, the primary epithelial cells of the skin. TSLP acts directly on a subset of TRPA1-positive sensory neurons to trigger robust itch behaviors. The results disclosed below demonstrate a new model whereby calcium-dependent TSLP release by keratinocytes activates both primary afferent neurons and immune cells to promote inflammatory responses in the skin and airways.

Materials and Methods

Cell Culture

Primary human epidermal keratinocytes (PromoCell) and HaCaT cells were cultured in PromoCell Keratinocyte Medium 2 and DMEM, respectively. siRNA directed against ORAI1, ORAI2, and STIM1 (Qiagen; 100 ng) were transfected using HiPerFect (Qiagen). HaCaT cells were transiently transfected with Lipofectamine 2000 (Invitrogen) using 1 μg HA-NFAT1(1-460)-GFP plasmid (Addgene 11107). DRG neurons were isolated from P18-30 mice and cultured as previously described (Wilson et al., 2011). All media and cell culture supplements were purchased from the UCSF Cell Culture Facility.

$Ca^{2+}$ Imaging $Ca^{2+}$ imaging was carried out as previously described (Wilson et al., 2011). Physiological Ringer solution: 140 mM NaCl, 5 mM KCl, 10 mM HEPES, 2 mM $CaCl_2$, 2 mM $MgCl_2$, 10 mM D-(+)-glucose, pH 7.4 with NaOH. Images were collected and analyzed using MetaFluor (Molecular Devices). $[Ca^{2+}]_i$ was determined from background-corrected $F_{340}/F_{380}$ ratio images using the relation $[Ca^{2+}]_i=K^*(R-R_{min})/(R_{max}-R)$ (Almers 1985), with the following parameters measured in keratinocytes: $R_{min}=0.3$; $R_{max}$32 2.2; and $K^*=3$ μM. Cells were classified as responders if $[Ca^{2+}]_i$ increased 15% above baseline.

Electrophysiology

Recordings were collected at 5 kHz and filtered at 2 kHz using an Axopatch 200B and PClamp software. Electrode resistances were 2-6 MΩ. Perforated patch internal solution: 140 mM CsCl, 5 mM EGTA, 10 mM HEPES, pH 7.4 with CsOH, 0.24 mg $ml^{-1}$ Amphotericin B (Rae et al., 1991). Stimulation protocol: 10 ms step to −80 mV, 150 ms ramp from −80 mV to +80 mV. Current clamp internal solution: 140 mM KCl, 5 mM EGTA and 10 mM HEPES (pH 7.4 with KOH). Series resistance of all cells were <30 MΩ and liquid junction potentials were <5 mV (no correction).

RT-PCR

RNA was extracted using RNeasy (Qiagen) and reverse transcription was performed using Superscript III. RT-PCR was carried out using SYBR Green (Invitrogen) on a StepOnePlus ABI machine. Threshold cycles for each transcript (Bogiatzi et al.) were normalized to GAPDH (ΔC). Calibrations and normalizations used the $2^{-\Delta\Delta Ct}$ method where $\Delta\Delta C_t=[(C_t(\text{target gene})-C_t(\text{reference gene})]-[C_t(\text{calibrator})-C_t(\text{reference gene})]$; GAPDH=reference gene; scrambled siRNA=calibrator. Experiments were performed in triplicate.

Histology

Histology was carried out as previously described (Gerhold, 2013). Antibodies: rabbit anti-PGP9.5 and rabbit anti-peripherin (Millipore) 1:1000; goat anti-TSLPR and mouse anti-NFATc1 (Santa Cruz Biotechnology) 1:100. IL7Rα and TSLPR probes (Panomics) were used for in situ hybridization following the Quantigene protocol (Panomics).

Protein Detection

TSLP protein levels were measured using the DuoSet ELISA kit (R&D Systems) on media collected 24 h after stimulation. TSLP release was normalized to vehicle. For western blots, 50 μg of cleared tissue lysate was resolved by SDS-PAGE, transferred to nitrocellulose membranes and probed with Anti-TSLP (1:250, Genetex), Anti-Calnexin (1:2,000, Abcam) and Anti-Actin (1:2,000).

Mice and Behavior

Mice (20-35 g) were housed in 12 h light-dark cycle at 21° C. Behavioral measurements were performed as previously described (Wilson et al., 2011). Compounds injected: 2.5 µg TSLP, 200 µg CQ, 100 pg tryptase dissolved in PBS, or RTX 1 µg/mL in 0.05% ascorbic acid and 7% Tween 80 (two days prior to pruritogen injection). For AITC behavior, 5 µL 10% AITC in mineral oil was applied to the right hind paw. Behavioral scoring was performed while blind to treatment and genotype. All experiments were performed under the policies and recommendations of the International Association for the Study of Pain and approved by the University of California, Berkeley Animal Care and Use Committee.

Data Analysis

Data are shown as mean±s.e.m. Statistical significance was evaluated using a one-way ANOVA followed by a Tukey-Kramer post hoc test or unpaired two-tailed Student's t-test for comparing difference between two samples. *$p<0.05$, $p<0.01$, *$p<0.001$.

Results

TSLP Evokes Robust Itch Behaviors in Mice.

To identify proteins that mediate itch transduction in somatosensory neurons, biomarkers of AD (Lee and Yu, 2011) in the mouse DRG transcriptome (Gerhold et al., 2013) were searched. Expression of the TSLP Receptor (TSLPR) was found in mouse sensory ganglia. While studies have shown that TSLP acts on various immune cells, TSLP signaling in the nervous system has not been reported. TSLPR is a heterodimer, composed of the IL7 receptor alpha (IL7Rα) chain and a TSLP-specific receptor chain (TSLPR; also Crlf2; (Pandey et al., 2000). Consistent with the presence of TSLPRs in sensory neurons, both TSLPR and IL7Rα transcripts were detected in mouse and human DRG using RT-PCR (FIG. 1A).

Somatosensory neurons mediate itch, touch and pain. Thus, it was asked if TSLP injection triggers itch and/or pain behaviors by using a mouse cheek model of itch, which permits easy distinction between these behaviors (Shimada and LaMotte, 2008). Injection of TSLP into the cheek of wild type mice evoked robust scratching that was not observed following vehicle injection (FIG. 1B-C). Wiping was never observed, indicating that TSLP triggers itch, rather than pain (Shimada and LaMotte, 2008). Intradermal injection of TSLP has been previously shown to evoke inflammation of the skin and lung over the course of hours or days (Jessup et al., 2008). However, robust itch behaviors were observed within 5 minutes of TSLP injection (latency to scratch=4.1±0.3 min).

While immune cells play a key role in long-term TSLP-evoked inflammation, whether immune cells are required for acute TSLP-triggered itch behaviors is unknown. The current model posits that TSLP acts on various immune cells to promote TH2 cell differentiation and inflammation. TSLP-evoked itch behaviors of wild type mice were compared to mouse strains lacking either T and B cells (RAG1−/−, NOD SCID) or mast cells (Kit(W-sh), FIG. 1D-E). TSLP triggered robust itch behaviors in all strains, with no significant differences between transgenic and congenic wild type littermates. Together, these data indicate that acute TSLP-evoked itch does not specifically require lymphocytes or mast cells, nor does it require the cytokines or other products produced when these cells are activated, and suggest that TSLP may act directly on sensory neurons.

Previous studies have shown that intradermal injection of the TRPV1 agonist, resiniferatoxin (RTX), results in ablation of primary afferent sensory neurons that express TRPV1, or TRPV1 and TRPA1, and consequently eliminates pain and itch behaviors (Imamachi et al., 2009; Mitchell et al., 2010). TSLP-evoked scratching was significantly decreased in RTX-treated mice as compared to control mice (FIG. 1F). These findings show for the first time that the AD cytokine, TSLP, induces itch via sensory neurons.

FIG. 1.

TSLP triggers robust itch behaviors in mice by activating sensory neurons. (A) PCR analysis of TSLPR and IL7Rα in mouse (left) and human (right) dorsal root ganglia (DRG). No product was amplified from the "no RT" control. (B) Image of itch-evoked scratching following intradermal injection of TSLP (2.5 µg/20 µl) into the cheek. (C) Quantification of scratching following TSLP injection in the cheek. TSLP (black) induced robust scratching compared to vehicle (white). n≥18 per group. (D) Itch behavior in $RAG^{+/+}$, $RAG^{−/−}$, NOD, and NOD/SCID mice following vehicle (PBS) or TSLP cheek injection. n≥8 per group. (E) Itch behavior in $cKIT^{+/+}$ and $cKIT^{−/−}$ mice following vehicle (PBS) or TSLP injection. n≥8 per group. (F) TSLP-evoked scratching following neuronal ablation by RTX (red) versus control (black). n≥6 per group. *$P<0.05$; $P<0.01$: *$P<0.001$. Error bars represent s.e.m.

TSLP Directly Activates an Uncharacterized Subset of Sensory Neurons.

It was asked whether TSLPRs are expressed in sensory neurons. DRG neurons are a heterogeneous population of cells, including a subset of small-diameter, peripherin-positive neurons that transmit itch and pain signals to the CNS, and release inflammatory mediators in the skin and other target organs (Basbaum et al., 2009). The prevalence of TSLPR-positive neurons and co-localization with known neuronal markers was examined. In situ hybridization revealed that TSLPR and IL7Rα were expressed in a subset of small diameter DRG neurons (FIG. 2A). Using antibodies against TSLPR, TSLPR protein expression was observed in 5.9% of cells in DRG sections (FIG. 2B). Co-staining of TSLPR and peripherin, a marker of small-diameter DRG neurons, demonstrated that all TSLPR-positive neurons are also peripherin-positive, with an average diameter of 18.1±0.6 µm (FIG. 2B). Overall, the characteristics of TSLPR-positive neurons match those of sensory neurons that mediate itch and/or pain (McCoy et al., 2013).

If TSLPRs mediate somatosensory transduction, they should localize to primary afferent nerve terminals in the skin Immunohistochemistry was performed with antibodies against TSLPR and the pan-neuronal fiber marker PGP9.5 on mouse skin (FIG. 2C). TSLPR staining was observed in 9% of PGP9.5-positive free nerve endings in the skin (FIG. 2C). These data show that TSLPRs are localized to sensory neuronal endings that innervate the skin in close apposition to keratinocytes in the epidermis. Taken together, these data demonstrate that the TSLPR subunits are expressed in a subset of sensory neurons that innervate the skin and mediate itch and/or pain transduction.

FIG. 2.

TSLP receptor components are expressed in sensory neurons. (A) DIC overlay images of in situ hybridization with cDNA probes detecting TSLPR, IL7Rα and TRPV1 in mouse DRG. Scale bar=400 µm. (B) Immunostaining of DRG sections with antibodies against peripherin and TSLPR in DRG sections. White arrows (right) mark peripherin- and TSLPR-positive neurons. Scale bar=400 µm. n≥4 mice/condition. (C) Immunostaining of PGP 9.5 and TSLPR in glabrous hind paw skin. The white arrows (right) mark PGP 9.5- and TSLPR-positive neurons. Scale bar=200 μm. n≥3 mice per condition.

Figure 3C:
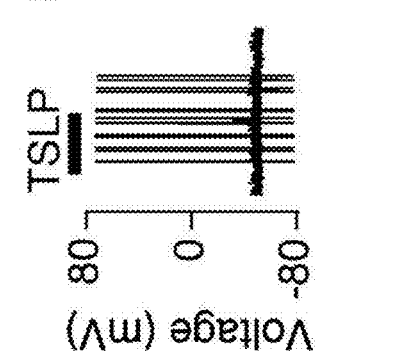
Figure 3B:
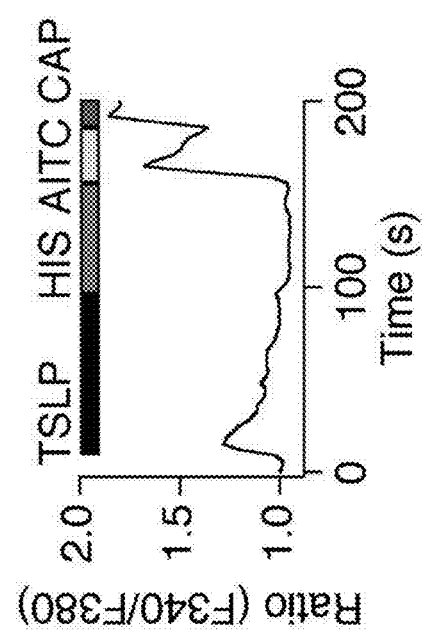

To test whether TSLPR is functional in sensory neurons, ratiometric $Ca^{2+}$ imaging was used (FIGS. 3A-B). It was found that 4.1±0.6% of DRG neurons showed robust increases in intracellular $Ca^{2+}$ following TSLP application (FIG. 3E); this is similar to the percentage of neurons that respond to other endogenous pruritogens, like BAM8-22 (Liu et al., 2009; Wilson et al., 2011). Previous studies have shown that small diameter sensory neurons transduce itch and/or pain signals via the ion channels TRPA1 and TRPV1 (Basbaum et al., 2009; Ross, 2011). Indeed, subsequent exposure to the TRPA1 agonist, allyl isothiocyanate (AITC), or the TRPV1 agonist, capsaicin (CAP), further increased $Ca^{2+}$ levels in all TSLP-positive cells (FIGS. 3A-B). Similarly, TSLP triggered action potential firing in a subset of CAP-sensitive neurons (FIG. 3C). These data suggest that TSLP activates a subset of TRPV1- and TRPA1-positive sensory neurons. The itch compounds histamine, chloroquine (CQ) and BAM8-22 have been shown to activate 5-20% of sensory neurons (Ikoma et al., 2006; Imamachi et al., 2009; Liu et al., 2009; Wilson et al., 2011) that express TRPA1 and/or TRPV1. TSLP appears to activate an undescribed subset of itch neurons, as most TSLP-positive neurons were insensitive to other itch compounds (FIG. 3A,B, D).

TSLPR and TRPA1 Mediate TSLP-Evoked Neuronal Activation.

Figure 3E:
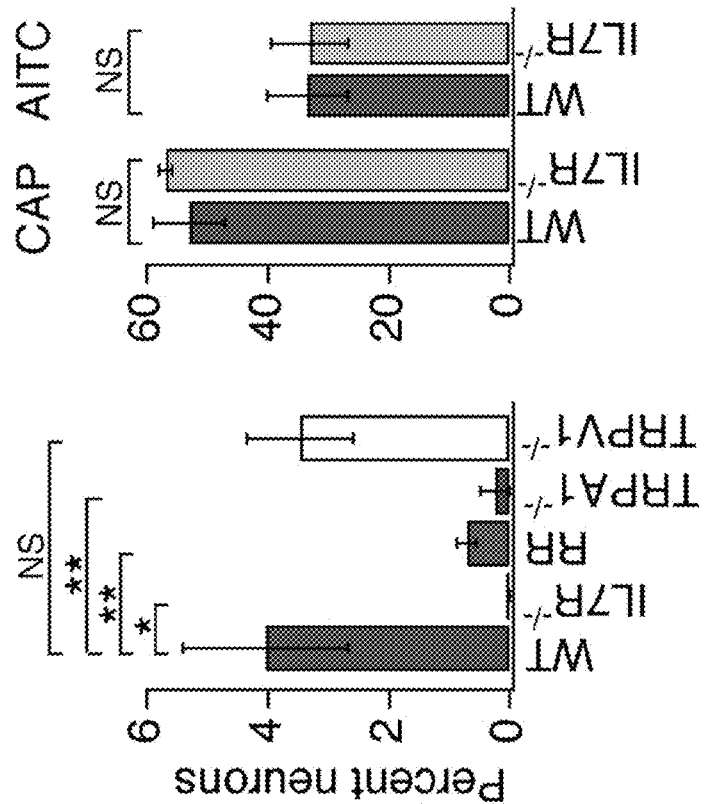
Figure 3D:
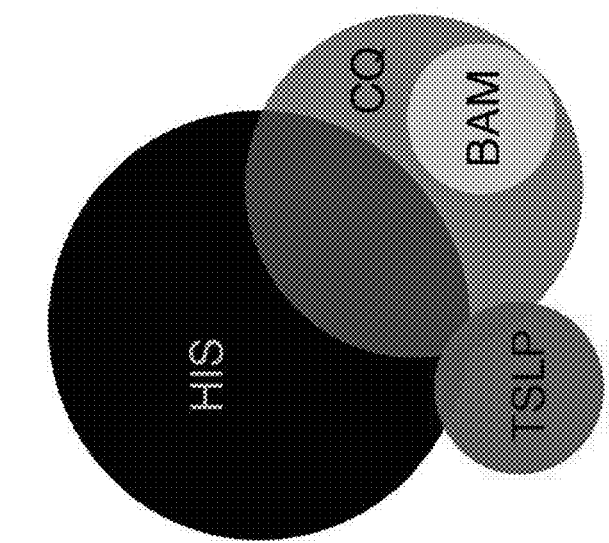

To ask whether TSLPRs mediate TSLP-evoked neuronal activation, TSLP-evoked $Ca^{2+}$ signals in neurons isolated from IL7Rα-deficient mice were examined TSLP-, but not AITC- or CAP-evoked $Ca^{2+}$ signaling, was abolished in IL7α-deficient neurons (FIG. 3E). These results are consistent with previous studies in immune cells showing that functional IL7Rα is required for TSLP signaling (Pandey et al., 2000). Here it is shown that functional TSLPRs are required for TSLP-evoked neuronal activation.

TRPV1 and TRPA1 channels are required for acute itch signaling and behavior (Ross, 2011). It was asked whether these channels are required for TSLP-evoked neuronal activation. TRPV1 and TRPA1 inhibition by the nonselective inhibitor, ruthenium red, significantly decreased neuronal sensitivity to TSLP (FIG. 3E). Neurons isolated from TRPA1- and TRPV1-deficient mice were compared to those from wild type littermates. TSLP-evoked $Ca^{2+}$ signals were significantly attenuated in TRPA1-deficient neurons, but not TRPV1-deficient neurons (FIG. 3E). The results show that TRPA1 channels mediate TSLP-evoked neuronal excitability.

Figure 3G:
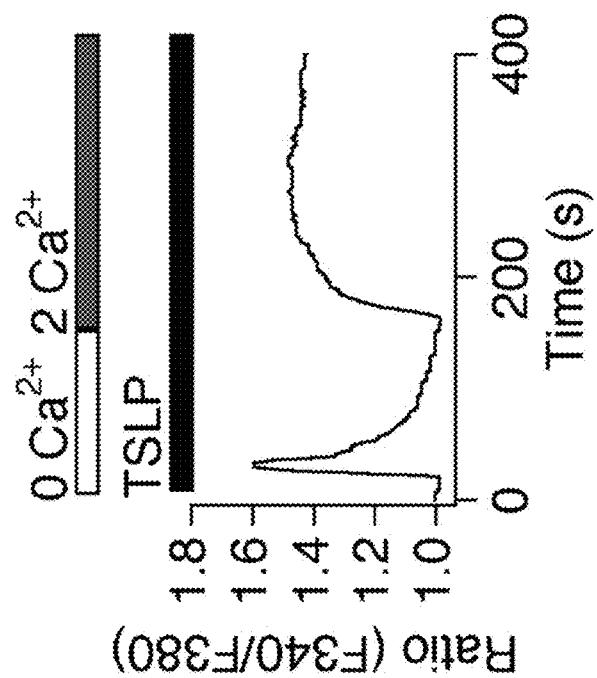
Figure 3F:
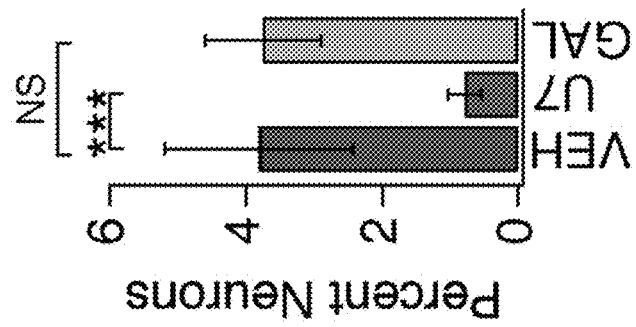

The mechanisms by which TSLPR activation promotes TRPA1 activity was examined Two signaling pathways have linked itch receptors to TRPA1 activation: Phospholipase C (PLC) signaling couples MrgprC11 to TRPA1; and, Gβγ signaling couples MrgprA3 to TRPA1 (Wilson et al., 2011). Treatment of cells with the PLC inhibitor, U73122, significantly reduced the prevalence of TSLP-sensitive neurons (FIG. 3F). In contrast, gallein, a Gβγ inhibitor, had no effect on TSLP-evoked $Ca^{2+}$ signals (FIG. 3F). Consistent with TSLP activation of the PLC pathway, TSLP triggers both release of $Ca^{2+}$ from intracellular stores, and subsequent $Ca^{2+}$ influx in sensory neurons (FIG. 3G). Overall, these experiments suggest that TSLPR and TRPA1 communicate via PLC signaling.

FIG. 3.

TSLP directly activates a subset of sensory neurons. (A) Representative images of Fura-2 loaded DRG neurons treated with vehicle, TSLP (2 ng/mL), histamine (HIS, 1 mM), AITC (200 μM) and capsaicin (CAP, 1 μM). (B) Representative trace shows a neuron that responds to TSLP, AITC and CAP, but not HIS. (C) Current-clamp recording showing TSLP- and CAP-evoked action potential firing in a DRG neuron. n≥60 cells. (D) A small percentage of the TSLP-sensitive population overlaps with the population of histamine- (HIS, 6%) or chloroquine-sensitive neurons (CQ, 6%), but not the BAM8-22 population (BAM, 0%). (E) Left: Prevalence of TSLP sensitivity in wild-type neurons (black), IL7Rα-deficient (grey) neurons, neurons treated with 20 μM ruthenium red (RR; red), TRPA1-deficient neurons (blue) and TRPV1-deficient neurons (white). Right: prevalence of AITC and CAP sensitivity in wild-type (black) and IL7Rα-deficient (grey) neurons n≥1000 cells. (F) Prevalence of TSLP sensitivity in neurons pre-treated with vehicle (black), a PLC blocker, U73122 (red) and the Gβγ blocker, gallein (grey) n≥600 cells. (G) Representative response to TSLP in the absence (0 mM $Ca^{2+}$) and presence (2 mM $Ca^{2+}$) of extracellular $Ca^{2+}$ n≥200 cells. *P<0.05; P<0.01: *P<0.001. Error bars represent s.e.m.

TSLPR and TRPA1 Mediate TSLP-Evoked Itch.

Figure 4A:
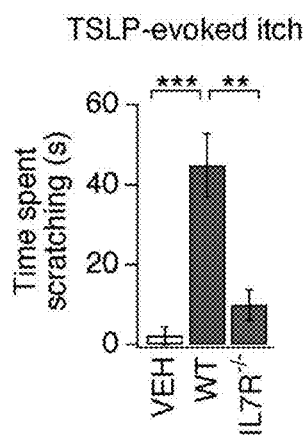
FIGS. 4A-4E demonstrate that TSLP induces robust TSLPR- and TRPA1-dependent itch behaviors.
Figure 4B:
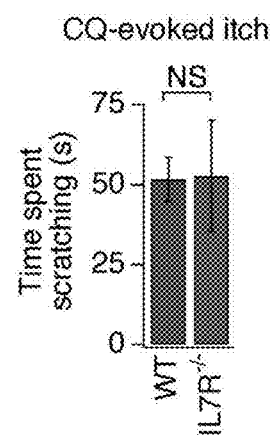
Figure 4C:
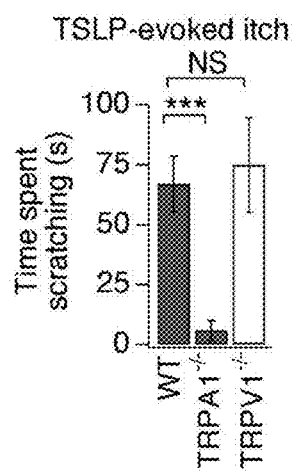

To test whether TSLP and TRPA1 receptors are required for TSLP-evoked itch behaviors, the cheek model of itch was used. TSLP-evoked scratching was significantly attenuated in IL7Rα-deficient mice, supporting a role for TSLPRs in TSLP itch signaling (FIG. 4A). These mice were not generally deficient in itch behaviors, as CQ-evoked scratching, which occurs via MrgprA3 (Liu et al., 2009), was normal (FIG. 4B). These data demonstrate that TSLP targets TSLPRs to trigger itch behaviors in vivo.

Figure 4D:
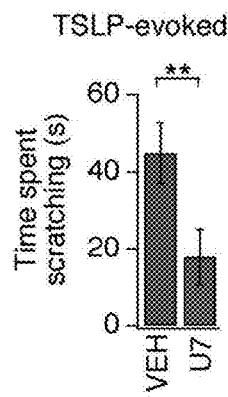
Figure 4E:
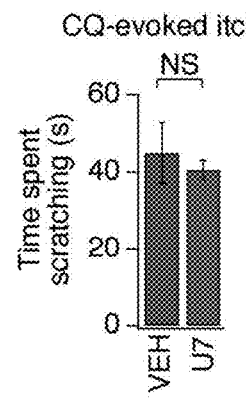

It was asked whether TSLP-evoked itch behaviors require TRP channels. TSLP-evoked scratching was abolished in TRPA1-deficient mice, but normal in TRPV1-deficient mice (FIG. 4D). These experiments show that both functional TSLPRs and TRPA1 channels are required for TSLP-evoked itch. PLC signaling is also required for the functional coupling between TSLPR and TRPA1 in vivo, as TSLP-evoked scratching was significantly attenuated by intradermal injection of U73122. Such treatment selectively silenced TSLP-evoked behaviors, as these mice displayed normal CQ-evoked scratching, which is PLC-independent (Wilson et al., 2011). Overall, these data demonstrate a new role for TSLP as a pruritogen and a robust activator of sensory neurons, and suggest that these neurons may contribute to the initiation of TSLP-evoked inflammatory responses in the skin in AD, and airways in asthma.

FIG. 4.

TSLP induces robust TSLPR- and TRPA1-dependent itch behaviors. (A) Itch behaviors following intradermal cheek injection of vehicle (10 μL PBS, white) or TSLP (2.5 μg/10 μL) into wild type (WT; black) or IL7Rα-deficient (red) mice. (B) Scratching in WT (black) and IL7Rα-deficient (red) mice following chloroquine (CQ) injection in the cheek. (C) Scratching in WT (black), TRPA1-deficient (red) and TRPV1-deficient (white) mice following TSLP injection (2.5 μg/10 μL). (D) Attenuation of TSLP-evoked scratching by 30 min preinjection with the PLC blocker, U73122 (U7) compared to vehicle (VEH). (E) CQ-evoked scratching in mice preinjected with U73122 or vehicle. The time spent scratching was quantified for 20 min after injection. n≥7 mice/condition. P<0.01; *P<0.001. Error bars represent s.e.m.

Keratinocyte Release of TSLP is $Ca^{2+}$-Dependent.

Our data establish a new cellular target for TSLP, supporting a model whereby both immune cells and sensory neurons are activated by keratinocyte-derived TSLP to drive itch and AD. What are the upstream mechanisms that govern the expression and release of TSLP by keratinocytes? Protease signaling via PAR2 plays a key role in TSLP production and AD. PAR2 activity, and levels of the endogenous PAR2 agonist, tryptase, are increased in the skin of AD patients (Steinhoff et al., 2003). Consistent with a previous study (Ui et al., 2006), injection of tryptase induced robust itch behaviors in mice (FIG. 5A). Tryptase-evoked itch was significantly attenuated in both PAR2- and IL7Rα-deficient mice (FIG. 5A), consistent with a pathway where PAR2 signaling promotes the release of TSLP from keratinocytes, which then acts on TSLPR-positive neurons to drive itch behaviors. The signaling pathways that control PAR2-induced TSLP expression in keratinocytes were determined.

Studies on keratinocytes have shown that the endogenous PAR2 agonist, tryptase, and the widely used PAR2 ligand mimetic, Ser-Leu-Ile-Gly-Arg-Leu (SLIGRL), elicits $Ca^{2+}$ influx (Schechter et al., 1998; Zhu et al., 2009) and triggers the $Ca^{2+}$-dependent release of inflammatory mediators (Halfter et al., 2005; Santulli et al., 1995; Schechter et al., 1998). For example, SLIGRL triggers a rise in intracellular $Ca^{2+}$ in keratinocytes (Zhu et al., 2009) and also promotes TSLP expression (Moniaga et al., 2013). It was asked if PAR2-evoked TSLP expression is $Ca^{2+}$-dependent. ELISA measurements revealed that treatment of keratinocytes with tryptase or SLIGRL, but not vehicle, triggered the robust secretion of TSLP (FIG. 5B). These data show that PAR2 stimulation of keratinocytes triggers TSLP release.

TSLP secretion was highly dependent on $Ca^{2+}$. First, TSLP secretion was not observed in keratinocytes treated with tryptase or SLIGRL in the absence of external $Ca^{2+}$ (FIG. 5B). In addition, treatment with the drug thapsigargin (TG), which promotes depletion of intracellular $Ca^{2+}$ stores and subsequent $Ca^{2+}$ influx, caused a significant increase in TSLP secretion (FIG. 5B). These data demonstrate that $Ca^{2+}$ is required and sufficient to drive TSLP secretion.

Figure 15A:
FIGS. 15A-15D demonstrate that human keratinocytes do not express human MRGPRX11; and that the PAR2 agonist, tryptase, does not activate mouse MrgprC11.
Figure 15B:
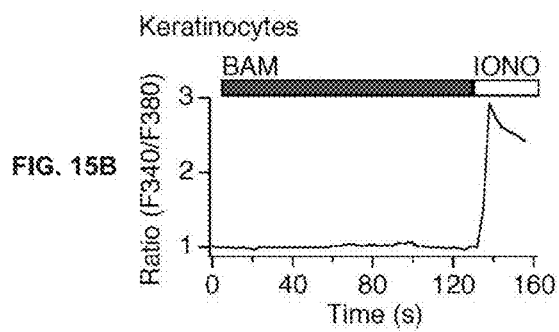
Figure 15C:
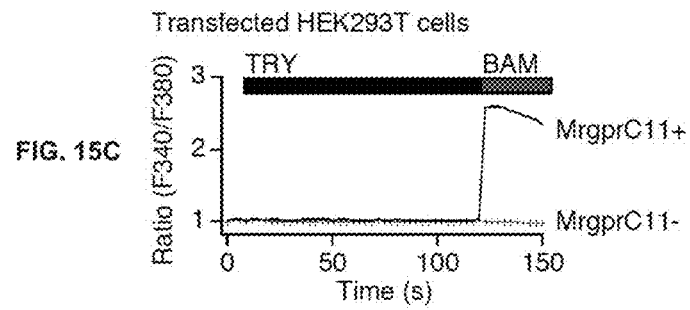
Figure 15D:
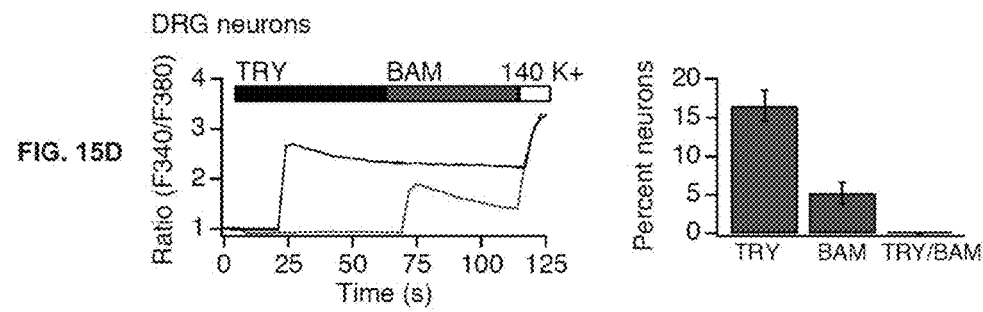

A recent study has shown that some PAR2 agonists, including SLIGRL, also activate the sensory neuron-specific itch receptor, MrgprC11 (MrgprX1 in human, (Liu et al., 2011). However, this result does not impact our in vitro studies for several reasons. First, keratinocytes do not express MrgprX1 (FIG. 15A). Second, keratinocytes are insensitive to the MrgprX1-specific ligand, BAM8-22 (FIG. 15B). Third, tryptase-evoked itch is dependent on PAR2 (FIG. 5A). Finally, tryptase does not activate MrgprC11 in mice (FIG. 15C-D). Overall, our findings support a model where tryptase- and SLIGRL treatment of keratinocytes promotes PAR2-evoked $Ca^{2+}$ signaling and subsequent secretion of TSLP.

FIG. 5.

PAR2 activation promotes itch behaviors and $Ca^{2+}$-dependent release of TSLP. (A) Itch-evoked scratching following injection of tryptase into the cheek (100 pg/20 μL) of wild type (WT; black), PAR2-deficient (blue) or IL7Rα-deficient mice (red), or PBS (white, 20 μL) injection into WT mice, n≥8 mice per condition. The time spent scratching was quantified for 1 h after injection. (B) TSLP secretion evoked by 24 h treatment with vehicle (VEH), tryptase (TRY, 100 nM), tryptase in the absence of extracellular $Ca^{2+}$ (TRY 0Ca), SLIGRL (100 μM), SLIGRL in the absence of extracellular $Ca^{2+}$ (SLIGRL 0Ca), or TG (1 μM). n≥4 replicates/condition *$P<0.05$; $P<0.01$; *$P<0.001$. Error bars represent s.e.m.

FIG. 15.

Human keratinocytes do not express human MRGPRX11 and the PAR2 agonist, tryptase, does not activate mouse MrgprC11 (A) PCR analysis of the human BAM8-22 (BAM) receptor, MrgprX1, in human dorsal root ganglia (DRG) and human keratinocytes (KRT). MrgprX1 was amplified from DRG, but not keratinocytes. MrgprX1 and GAPDH were amplified from RT-treated tissue but not from "no RT" controls. (B) Representative response to BAM8-22 (BAM, 2 μM) in human keratinocytes. (C) Representative response to tryptase (TRY, 3 μM) and BAM8-22 (BAM, 2 μM) in the presence or absence of the mouse BAM8-22 receptor, MrgprC11. (D) Left: representative traces showing a neuron that is sensitive to BAM8-22 (BAM) but not tryptase (TRY, blue), and a neuron that is sensitive to tryptase but not BAM8-22 (black). Right: quantification of the prevalence of tryptase-responsive (TRY, black), BAM8-22-responsive (blue, BAM), and tryptase- and BAM8-22-responsive neurons in mouse dorsal root ganglia. n≥500 cells. Data are represented as mean+/−SEM ORAI1 and STIM1 are Required for PAR2-Evoked $Ca^{2+}$ Influx.

Ratiometric $Ca^{2+}$ imaging was used to dissect the mechanisms underlying PAR2-evoked $Ca^{2+}$ signals. Consistent with previous studies, tryptase and SLIGRL evoked a rise in intracellular $Ca^{2+}$ in keratinocytes (FIG. 6A-C; Zhu et al., 2009). In some cells, PAR2 signals via PLC (Dai et al., 2007), and PLC activation leads to $Ca^{2+}$-release from $IP_3$-dependent stores and influx via the store-operated $Ca^{2+}$ entry (SOCE) pathway. Indeed, PAR2 activation in keratinocytes induced both $Ca^{2+}$ release from intracellular stores and $Ca^{2+}$ influx, consistent with activation of SOCE (FIG. 6A-B).

What are the molecules mediating PAR2-evoked SOCE in keratinocytes? Both ORAI and TRPC channels have been implicated in SOCE (Cahalan, 2009; Ramsey et al., 2006). It was asked whether PAR2 activates SOCE via ORAI or TRPC channels, which can be distinguished by their distinct pharmacological profiles (DeHaven et al., 2008; Lis et al., 2007; Zhang et al., 2008). The drugs 2-Aminoethoxydiphenyl borate (2-APB) and lanthanum ($La^{3+}$) inhibit ORAI1 and ORAI2 channels, but not ORAI3 or TRPC channels (DeHaven et al., 2008; Lis et al., 2007; Zhang et al., 2008). Tryptase and SLIGRL-evoked $Ca^{2+}$ influx was significantly attenuated by treatment with 2-APB or $La^{3+}$. These data show that tryptase and SLIGRL activate the same SOCE pathway and support a role for ORAI channels in PAR2-evoked SOCE (FIG. 6C).

ORAI and TRPC channels can also be distinguished by their distinct biophysical characteristics: ORAI1 and ORAI2 are $Ca^{2+}$-selective channels that are inwardly-rectifying, while TRPC channels are outwardly-rectifying, non-selective channels (Cahalan, 2009; Owsianik et al., 2006; Yeromin et al., 2006). Thus, SLIGRL-evoked currents were measured using perforated-patch, voltage-clamp recordings on keratinocytes. Treatment with SLIGRL triggered an ORAI1/2-like current; the currents were dependent on extracellular $Ca^{2+}$, displayed an inwardly-rectifying current-voltage relationship, and displayed no measurable reversal potentials below +80 mV (FIG. 6D). These results implicate ORAI1 and/or ORAI2 in PAR2-evoked SOCE.

qPCR demonstrated that keratinocytes express ORAI1, ORAI2 and the ORAI regulator, Stromal Interaction Molecule 1 (STIM1). The role of ORAI1, ORAI2, and STIM1 in SOCE was examined using siRNA-mediated knockdown. Depletion of ORAI1 transcripts by 71% or STIM1 transcripts by 84% significantly diminished $Ca^{2+}$ entry in response to SLIGRL as compared to scrambled control siRNA (FIG. 6E-G). ORAI1 and STIM1 knockdown also significantly attenuated tryptase-evoked $Ca^{2+}$ signals. In contrast, depletion of ORAI2 transcripts by 86% had no effect on SLIGRL-evoked SOCE (FIG. 6E, 6G). These data demonstrate that ORAI1 and STIM1 are required for PAR2-evoked SOCE in human keratinocytes. ORAI1 and STIM1 knockdown also attenuated TG-evoked SOCE (FIG. 6G), suggesting that ORAI1 is the primary store-operated $Ca^{2+}$ pathway in keratinocytes.

FIG. 6.

ORAI1 and STIM1 are required for PAR2- and TG-evoked $Ca^{2+}$ influx. (A) Representative response to SLIGRL (100 μM) following pretreatment with vehicle (black) or 2-aminoethoxydiphenyl borate (50 μM 2-APB; red). (B) Representative response to tryptase (100 nM) following pretreatment with vehicle (black) or 2-APB (red). (C) Average steady state $Ca^{2+}$ level following SLIGRL- or tryptase (TRY)-evoked $Ca^{2+}$ influx (2 mM $Ca^{2+}$), in the presence of 2-APB (red), lanthanum (50 nM $La^{3+}$, blue), or vehicle (CTRL, black). n≥1000 cells. (D) Representative current-voltage trace in the presence of SLIGRL (100 μM) in perforated-patch, whole-cell voltage-clamp recordings. Representative baseline subtracted currents before (red) and during application of SLIGRL (black). n≥3 cells/condition. (E) siRNA-induced silencing of STIM1 (red), ORAI1 (blue), and ORAI2 (grey) mRNA in keratinocytes. Expression was normalized to scrambled-siRNA control (black). n≥1000 cells. (F) Representative traces of SLIGRL-evoked (100 μM) $Ca^{2+}$ signals following treatment with siRNA targeting STIM1 (red) or scrambled control (CTRL, black). (G) Average steady state $Ca^{2+}$ concentration after treatment with SLIGRL (100 μM) or TG (1 μM) in cells treated with scrambled siRNA (black), STIM1 (red), ORAI1 (blue), or ORAI2 (grey) siRNA. n≥500 cells. *$P<0.05$; $P<0.01$; *$P<0.001$. Error bars represent s.e.m.

PAR2-Activation Induces $Ca^{2+}$-Dependent NFAT Translocation and TSLP Secretion.

In immune cells, ORAI1 signaling activates NFAT, which triggers cytokine expression and secretion (Feske et al., 2006; Gwack et al., 2007). The ORAI1/NFAT pathway may play a similar role in keratinocytes, promoting the expression and secretion of TSLP. Consistent with a regulatory role for NFAT in TSLP expression, two NFAT binding motifs (GGAAAATN) (Rao et al., 1997; Zhu et al., 2009) are present in the 5'-upstream regulatory region of the human TSLP gene. These findings imply that PAR2 may trigger NFAT-dependent expression and release of TSLP; however, the evidence is merely correlative. To directly test this hypothesis, PAR2-dependent NFAT translocation and TSLP expression and release was measured in keratinocytes.

Following a rise in $Ca^{2+}$, NFAT is dephosphorylated by the $Ca^{2+}$-dependent phosphatase calcineurin and translocates from the cytosol to the nucleus to promote transcription of target genes (Rao et al., 1997) Immunostaining demonstrated that treatment of keratinocytes with SLIGRL for 30 minutes induced robust NFAT translocation to the nucleus (FIG. 7A). This translocation was attenuated by blocking ORAI channels with 2-APB, or by inhibiting NFAT activity with cyclosporine A (CsA), an inhibitor of calcineurin (FIG. 7A); similar results were observed using live cell imaging of a human keratinocyte cell line, HaCat, that expressed NFAT-GFP (FIG. 7B). These results show that PAR2 activation induces $Ca^{2+}$-dependent NFAT translocation, which may lead to NFAT-dependent changes in gene expression. In support of this model, PAR2-evoked SOCE robustly increased expression of TSLP transcripts in keratinocytes (FIG. 7C).

The question of whether ORAI1/NFAT signaling mediates PAR2-evoked TSLP release was addressed. It was found that siRNA-mediated knockdown of ORAI1 or STIM1 significantly attenuated SLIGRL-evoked TSLP release by keratinocytes, suggesting that ORAI1 is required for PAR2-evoked TSLP secretion (FIG. 7D). Likewise, inhibition of NFAT-mediated transcription with CsA also attenuated TSLP release (FIG. 7E), but had no effect on SOCE-evoked $Ca^{2+}$ signals (not shown). In addition to cutaneous epithelial cells, airway epithelial cells of patients with allergic rhinitis, AD and asthma also display high TSLP expression (Ziegler et al., 2013). Previous studies have shown that TG induces ORAI1-dependent $Ca^{2+}$ signals in human airway epithelial cells (Gusarova et al., 2011). Interestingly, it was found that, like keratinocytes, SOCE triggers robust TSLP expression in human airway epithelial cells, which can be blocked by CsA (not shown). These data identify ORAI1-dependent NFAT activation as a regulator of TSLP expression and release in both cutaneous and airway epithelial cells.

Figure 7F:
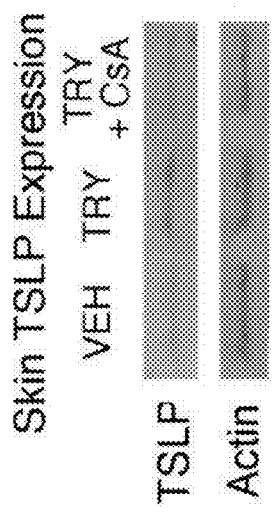
Figure 7G:
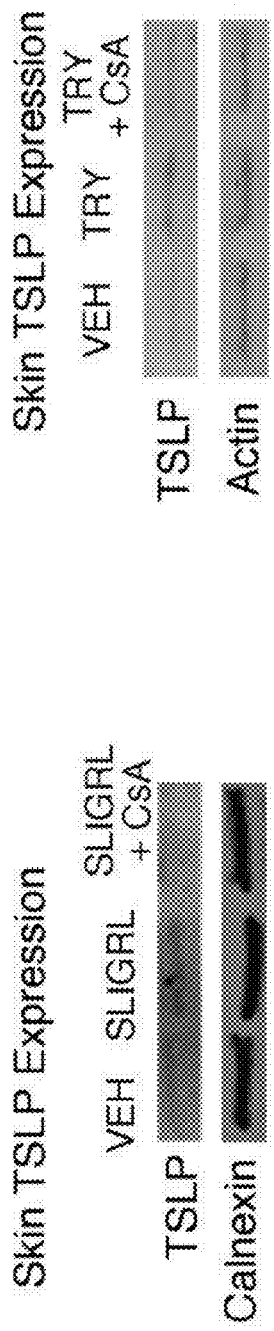

The hypothesis that NFAT promotes TSLP expression in vivo was tested. Mice were treated with SLIGRL, SLIGRL and CSA, or vehicle via intradermal injection into the back. TSLP protein levels in treated skin were measured three hours after injection. Co-injection of CsA significantly attenuated SLIGRL-evoked TSLP protein expression in skin (FIG. 7F). Similar results were also observed with the endogenous PAR2 agonist, tryptase (FIG. 7G), demonstrating that PAR2 triggers TSLP expression via the $Ca^{2+}$-calmodulin/NFAT pathway in vivo.

Figure 7H:
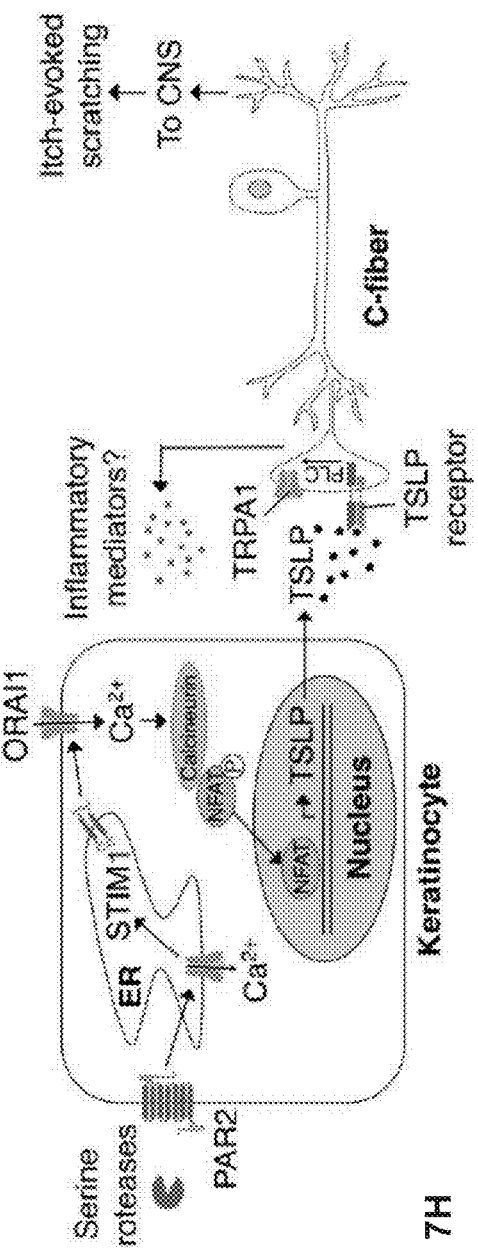

In conclusion, cellular and behavioral data shows that ORAI1/NFAT signaling regulates TSLP release by keratinocytes, and that TRPA1 is required for TSLP-evoked activation of sensory neurons and subsequent itch behaviors. The data presented herein support a new model whereby TSLP released from keratinocytes acts directly on sensory neurons to trigger robust itch-evoked scratching (FIG. 7H).

FIG. 7.

PAR2 activation promotes $Ca^{2+}$-dependent NFAT translocation and TSLP secretion. (A) Representative images displaying cytosolic and nuclear localization of NFAT (green) and DAPI (red) in keratinocytes after a 30 min incubation with vehicle (VEH), SLIGRL (100 μM), SLIGRL+2APB (50 μM) or SLIGRL+CsA (1 μM). Pretreatment with 2APB or CsA prevented SLIGRL-induced NFAT nuclear translocation. n≥300 cells. (B) Fraction of HaCaT keratinocytes displaying nuclear localization of NFAT-GFP following treatment with SLIGRL (100 μM; black), SLIGRL and 2APB (50 μM; red), SLIGRL+CsA (1 μM; blue) or vehicle (VEH; white). n≥1000 cells. (C) TSLP expression in human keratinocytes following a 3 h treatment with vehicle (VEH, black) or SLIGRL (100 μM, red). n≥3. (D) SLIGRL-evoked TSLP release in cells treated with scrambled (black), STIM1 (red) or ORAI1 siRNA (blue). Secretion was normalized to vehicle-treated cells (white). n≥3. (E) TSLP release in response to treatment with vehicle (VEH, black), SLIGRL (100 μM, red) or SLIGRL+CsA (1 μM, blue). (F) Western blot of skin lysates from mice following intradermal injection with vehicle (VEH), SLIGRL, or SLIGRL+CsA. Samples were probed with antibodies against TSLP and calnexin (loading control). n≥3 mice. (G) Western blot of skin lysates isolated from mice following intradermal injection with vehicle (VEH), tryptase (TRY; 100 pg/20 μL), or tryptase+CsA (TRY+CsA). Samples were probed with antibodies against TSLP, and actin (loading control). n≥3 mice. *$P<0.05$; $P<0.01$; *$P<0.001$. Error bars represent s.e.m. (H) Schematic diagram depicting the ORAI1 signaling pathway in keratinocytes that links PAR2 to TSLP secretion and activation of itch neurons. Activation of PAR2 triggers release of $Ca^{2+}$ from the ER and activation of STIM1, which opens ORAI1 channels to promote Ca$^{2+}$ influx. Ca$^{2+}$ activates the phosphatase calcineurin, which dephosphorylates NFAT and causes nuclear translocation, thus inducing transcription of TSLP. Secreted TSLP depolarizes a subset of C-fibers to evoke itch, in a TSLPR- and TRPA1-dependent manner Activation of TRPA1-expressing sensory neurons can then lead to release of neuropeptides in the skin in a process known as neurogenic inflammation.

REFERENCES

Al-Daraji, W. I., Grant, K. R., Ryan, K., Saxton, A., and Reynolds, N. J. (2002). Localization of calcineurin/NFAT in human skin and psoriasis and inhibition of calcineurin/NFAT activation in human keratinocytes by cyclosporin A. J Invest Dermatol 118, 779-788.

Almers, N. (1985). The Ca signal from fura-2 loaded mast cells depends strongly on the method of dye-loading. FEBS Letters 192, 13-18.

Andoh, T., Katsube, N., Maruyama, M., and Kuraishi, Y. (2001). Involvement of leukotriene B(4) in substance P-induced itch-associated response in mice. J Invest Dermatol 117, 1621-1626.

Basbaum, A. I., Bautista, D. M., Scherrer, G., and Julius, D. (2009). Cellular and molecular mechanisms of pain. Cell 139, 267-284.

Bautista, D. M., Pellegrino, M., and Tsunozaki, M. (2013). TRPA1: A gatekeeper for inflammation. Annu Rev Physiol 75, 181-200.

Bogiatzi, S. I., Guillot-Delost, M., Cappuccio, A., Bichet, J. C., Chouchane-Mlik, O, Donnadieu, M. H., Barillot, E., Hupe, P., Chlichlia, K., Efremidou, E. I., et al. (2012). Multiple-checkpoint inhibition of thymic stromal lymphopoietin-induced TH2 response by TH17-related cytokines. J Allergy Clin Immunol 130, 233-240 e235.

Briot, A., Deraison, C., Lacroix, M., Bonnart, C., Robin, A., Besson, C., Dubus, P., and Hovnanian, A. (2009). Kallikrein 5 induces atopic dermatitis-like lesions through PAR2-mediated thymic stromal lymphopoietin expression in Netherton syndrome. J Exp Med 206, 1135-1147.

Briot, A., Lacroix, M., Robin, A., Steinhoff, M., Deraison, C., and Hovnanian, A. (2010). Par2 inactivation inhibits early production of TSLP, but not cutaneous inflammation, in Netherton syndrome adult mouse model. J Invest Dermatol 130, 2736-2742.

Cahalan, M. D. (2009). STIMulating store-operated Ca(2+) entry. Nat Cell Biol 11, 669-677.

Cevikbas, F., Steinhoff, A., Homey, B., and Steinhoff, M. (2007). Neuroimmune interactions in allergic skin diseases. Curr Opin Allergy Clin Immunol 7, 365-373.

Chang, W. C., Lee, C. H., Hirota, T., Wang, L. F., Doi, S., Miyatake, A., Enomoto, T., Tomita, K., Sakashita, M., Yamada, T., et al. (2012). ORAI1 genetic polymorphisms associated with the susceptibility of atopic dermatitis in Japanese and Taiwanese populations. PLoS One 7, e29387.

Dai, Y., Wang, S., Tominaga, M., Yamamoto, S., Fukuoka, T., Higashi, T., Kobayashi, K., Obata, K., Yamanaka, H., and Noguchi, K. (2007). Sensitization of TRPA1 by PAR2 contributes to the sensation of inflammatory pain. J Clin Invest 117, 1979-1987.

DeHaven, W. I., Smyth, J. T., Boyles, R. R., Bird, G. S., and Putney, J. W., Jr. (2008). Complex actions of 2-aminoethyldiphenyl borate on store-operated Ca2+ entry. J Biol Chem 283, 19265-19273.

Feske, S. (2010). CRAC channelopathies. Pflugers Arch 460, 417-435.

Feske, S., Gwack, Y., Prakriya, M., Srikanth, S., Puppel, S. H., Tanasa, B., Hogan, P. G., Lewis, R. S., Daly, M., and Rao, A. (2006). A mutation in Orai1 causes immune deficiency by abrogating CRAC channel function. Nature 441, 179-185.

Fitzsimons, C., Engel, N., Duran, H., Policastro, L., Cricco, G., Martin, G., Molinari, B., and Rivera, E. (2001). Histamine production in mouse epidermal keratinocytes is regulated during cellular differentiation. Inflamm Res 50 Suppl 2, S100-101.

Gerhold, K. A., Pellegrino, M., Tsunozaki, M., Morita, T., Leitch, D. B., Tsuruda, P. R., Brem, R. B., Catania, K. C., and Bautista, D. M. (2013). The star-nosed mole reveals clues to the molecular basis of mammalian touch. PLoS One 8, e55001.

Gusarova, G. A., Trejo, H. E., Dada, L. A., Briva, A., Welch, L. C., Hamanaka, R. B., Mutlu, G. M., Chandel, N. S., Prakriya, M., and Sznajder, J. I. (2011). Hypoxia leads to Na,K-ATPase downregulation via Ca(2+) release-activated Ca(2+) channels and AMPK activation. Mol Cell Biol 31, 3546-3556.

Gwack, Y., Feske, S., Srikanth, S., Hogan, P. G., and Rao, A. (2007). Signalling to transcription: store-operated Ca2+ entry and NFAT activation in lymphocytes. Cell Calcium 42, 145-156.

Halfter, U. M., Derbyshire, Z. E., and Vaillancourt, R. R. (2005). Interferon-gamma-dependent tyrosine phosphorylation of MEKK4 via Pyk2 is regulated by annexin II and SHP2 in keratinocytes. Biochem J 388, 17-28.

He, R., and Geha, R. S. (2010). Thymic stromal lymphopoietin. Ann NY Acad Sci 1183, 13-24.

Holgate, S. T. (2007). The epithelium takes centre stage in asthma and atopic dermatitis. Trends Immunol 28, 248-251.

Hovnanian, A. (2013). Netherton syndrome: skin inflammation and allergy by loss of protease inhibition. Cell Tissue Res 351, 289-300.

Ikoma, A., Rukwied, R., Stander, S., Steinhoff, M., Miyachi, Y., and Schmelz, M. (2003). Neuronal sensitization for histamine-induced itch in lesional skin of patients with atopic dermatitis. Arch Dermatol 139, 1455-1458.

Ikoma, A., Steinhoff, M., Stander, S., Yosipovitch, G., and Schmelz, M. (2006). The neurobiology of itch. Nat Rev Neurosci 7, 535-547.

Imamachi, N., Park, G. H., Lee, H., Anderson, D. J., Simon, M. I., Basbaum, A. I., and Han, S. K. (2009). TRPV1-expressing primary afferents generate behavioral responses to pruritogens via multiple mechanisms. Proc Natl Acad Sci USA 106, 11330-11335.

Jariwala, S. P., Abrams, E., Benson, A., Fodeman, J., and Zheng, T. (2011). The role of thymic stromal lymphopoietin in the immunopathogenesis of atopic dermatitis. Clin Exp Allergy 41, 1515-1520.

Jessup, H. K., Brewer, A. W., Omori, M., Rickel, E. A., Budelsky, A. L., Yoon, B. R., Ziegler, S. F., and Comeau, M. R. (2008). Intradermal administration of thymic stromal lymphopoietin induces a T cell- and eosinophil-dependent systemic Th2 inflammatory response. J Immunol 181, 4311-4319.

Kanda, N., Koike, S., and Watanabe, S. (2005). Prostaglandin E2 enhances neurotrophin-4 production via EP3 receptor in human keratinocytes. J Pharmacol Exp Ther 315, 796-804.

Kouzaki, H., O'Grady, S. M., Lawrence, C. B., and Kita, H. (2009). Proteases induce production of thymic stromal lymphopoietin by airway epithelial cells through protease-activated receptor-2. J Immunol 183, 1427-1434.

Lee, C. H., and Yu, H. S. (2011). Biomarkers for itch and disease severity in atopic dermatitis. Curr Probl Dermatol 41, 136-148.

Li, M., Messaddeq, N., Teletin, M., Pasquali, J. L., Metzger, D., and Chambon, P. (2005). Retinoid X receptor ablation in adult mouse keratinocytes generates an atopic dermatitis triggered by thymic stromal lymphopoietin. Proc Natl Acad Sci USA 102, 14795-14800.

Lis, A., Peinelt, C., Beck, A., Parvez, S., Monteilh-Zoller, M., Fleig, A., and Penner, R. (2007). CRACM1, CRACM2, and CRACM3 are store-operated Ca2+ channels with distinct functional properties. Curr Biol 17, 794-800.

Liu, B., Escalera, J., Balakrishna, S., Fan, L., Caceres, A. I., Robinson, E., Sui, A., McKay, M. C., McAlexander, M. A., Herrick, C. A., et al. (2013). TRPA1 controls inflammation and pruritogen responses in allergic contact dermatitis. FASEB J.

Liu, Q., Tang, Z., Surdenikova, L., Kim, S., Patel, K. N., Kim, A., Ru, F., Guan, Y., Weng, H. J., Geng, Y., et al. (2009). Sensory neuron-specific GPCR Mrgprs are itch receptors mediating chloroquine-induced pruritus. Cell 139, 1353-1365.

Liu, Q., Weng, H. J., Patel, K. N., Tang, Z., Bai, H., Steinhoff, M., and Dong, X. (2011). The distinct roles of two GPCRs, MrgprC11 and PAR2, in itch and hyperalgesia. Sci Signal 4, ra45.

Locksley, R. M. (2010). Asthma and allergic inflammation. Cell 140, 777-783.

Madan, V., and Griffiths, C. E. (2007). Systemic ciclosporin and tacrolimus in dermatology. Dermatol Ther 20, 239-250.

McCoy, E. S., Taylor-Blake, B., Street, S. E., Pribisko, A. L., Zheng, J., and Zylka, M. J. (2013). Peptidergic CGRPalpha Primary Sensory Neurons Encode Heat and Itch and Tonically Suppress Sensitivity to Cold. Neuron 78, 138-151.

McCoy, E. S., Taylor-Blake, B., and Zylka, M. J. (2012). CGRPalpha-expressing sensory neurons respond to stimuli that evoke sensations of pain and itch. PLoS One 7, e36355.

Mitchell, K., Bates, B. D., Keller, J. M., Lopez, M., Scholl, L., Navarro, J., Madian, N., Haspel, G., Nemenov, M. I., and Iadarola, M. J. (2010). Ablation of rat TRPV1-expressing Adelta/C-fibers with resiniferatoxin: analysis of withdrawal behaviors, recovery of function and molecular correlates. Mol Pain 6, 94.

Moniaga, C. S., Jeong, S. K., Egawa, G., Nakajima, S., Hara-Chikuma, M., Jeon, J. E., Lee, S. H., Hibino, T., Miyachi, Y., and Kabashima, K. (2013). Protease activity enhances production of thymic stromal lymphopoietin and basophil accumulation in flaky tail mice. Am J Pathol 182, 841-851.

Owsianik, G., Talavera, K., Voets, T., and Nilius, B. (2006). Permeation and selectivity of TRP channels. Annu Rev Physiol 68, 685-717.

Pandey, A., Ozaki, K., Baumann, H., Levin, S. D., Puel, A., Farr, A. G., Ziegler, S. F., Leonard, W. J., and Lodish, H. F. (2000). Cloning of a receptor subunit required for signaling by thymic stromal lymphopoietin. Nat Immunol 1, 59-64.

Prakriya, M., Feske, S., Gwack, Y., Srikanth, S., Rao, A., and Hogan, P. G. (2006). Orai1 is an essential pore subunit of the CRAC channel. Nature 443, 230-233.

Rae, J., Cooper, K., Gates, P., and Watsky, M. (1991). Low access resistance perforated patch recordings using amphotericin B. J Neurosci Methods 37, 15-26.

Ramsey, I. S., Delling, M., and Clapham, D. E. (2006). An introduction to TRP channels. Annu Rev Physiol 68, 619-647.

Rao, A., Luo, C., and Hogan, P. G. (1997). Transcription factors of the NFAT family: regulation and function. Annu Rev Immunol 15, 707-747.

Ross, S. E. (2011). Pain and itch: insights into the neural circuits of aversive somatosensation in health and disease. Curr Opin Neurobiol 21, 880-887.

Santulli, R. J., Derian, C. K., Darrow, A. L., Tomko, K. A., Eckardt, A. J., Seiberg, M., Scarborough, R. M., and Andrade-Gordon, P. (1995). Evidence for the presence of a protease-activated receptor distinct from the thrombin receptor in human keratinocytes. Proc Natl Acad Sci USA 92, 9151-9155.

Schechter, N. M., Brass, L. F., Lavker, R. M., and Jensen, P. J. (1998). Reaction of mast cell proteases tryptase and chymase with protease activated receptors (PARs) on keratinocytes and fibroblasts. J Cell Physiol 176, 365-373.

Shimada, S. G., and LaMotte, R. H. (2008). Behavioral differentiation between itch and pain in mouse. Pain 139, 681-687.

Spergel, J. M., and Paller, A. S. (2003). Atopic dermatitis and the atopic march. J Allergy Clin Immunol 112, S118-127.

Tobin, D., Nabarro, G., Baart de la Faille, H., van Vloten, W. A., van der Putte, S. C., and Schuurman, H. J. (1992). Increased number of immunoreactive nerve fibers in atopic dermatitis. J Allergy Clin Immunol 90, 613-622.

Tominaga, M., Tengara, S., Kamo, A., Ogawa, H., and Takamori, K. (2009). Psoralen-ultraviolet A therapy alters epidermal Sema3A and NGF levels and modulates epidermal innervation in atopic dermatitis. J Dermatol Sci 55, 40-46.

Ui, H., Andoh, T., Lee, J. B., Nojima, H., and Kuraishi, Y. (2006). Potent pruritogenic action of tryptase mediated by PAR-2 receptor and its involvement in anti-pruritic effect of nafamostat mesilate in mice. Eur J Pharmacol 530, 172-178.

Wilson, S. R., Gerhold, K. A., Bifolck-Fisher, A., Liu, Q., Patel, K. N., Dong, X., and Bautista, D. M. (2011). TRPA1 is required for histamine-independent, Mas-related G protein-coupled receptor-mediated itch. Nat Neurosci 14, 595-602.

Wilson, S. R., Nelson, A. M., Batia, L., Morita, T., Estandian, D., Owens, D. M., Lumpkin, E. A., and Bautista, D. M. (2013). The Ion Channel TRPA1 Is Required for Chronic Itch. J Neurosci 33, 9283-9294.

Yeromin, A. V., Zhang, S. L., Jiang, W., Yu, Y., Safrina, O., and Cahalan, M. D. (2006). Molecular identification of the CRAC channel by altered ion selectivity in a mutant of Orai. Nature 443, 226-229.

Ying, S., O'Connor, B., Ratoff, J., Meng, Q., Mallett, K., Cousins, D., Robinson, D., Zhang, G., Zhao, J., Lee, T. H., et al. (2005). Thymic stromal lymphopoietin expression is increased in asthmatic airways and correlates with expression of Th2-attracting chemokines and disease severity. J Immunol 174, 8183-8190.

Yoo, J., Omori, M., Gyarmati, D., Zhou, B., Aye, T., Brewer, A., Comeau, M. R., Campbell, D. J., and Ziegler, S. F. (2005). Spontaneous atopic dermatitis in mice expressing an inducible thymic stromal lymphopoietin transgene specifically in the skin. J Exp Med 202, 541-549.

Zhang, S. L., Kozak, J. A., Jiang, W., Yeromin, A. V., Chen, J., Yu, Y., Penna, A., Shen, W., Chi, V., and Cahalan, M. D. (2008). Store-dependent and -independent modes regulating Ca2+ release-activated Ca2+ channel activity of human Orai1 and Orai3. J Biol Chem 283, 17662-17671.

Zhu, Y., Wang, X. R., Peng, C., Xu, J. G., Liu, Y. X., Wu, L., Zhu, Q. G., Liu, J. Y., Li, F. Q., Pan, Y. H., et al. (2009). Induction of leukotriene B(4) and prostaglandin E(2) release from keratinocytes by protease-activated receptor-2-activating peptide in ICR mice. Int Immunopharmacol 9, 1332-1336.

Ziegler, S. F., Roan, F., Bell, B. D., Stoklasek, T. A., Kitajima, M., and Han, H. (2013). The Biology of Thymic Stromal Lymphopoietin (TSLP). Adv Pharmacol 66, 129-155.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of identifying a candidate agent for treating atopic dermatitis, the method comprising:
   a) contacting a test agent in vitro with a cell that expresses a Protease Activated Receptor 2 (PAR2) polypeptide and an ORAI1 polypeptide, wherein the PAR2 polypeptide comprises an amino acid sequence having at least 95% amino acid sequence identity to the amino acid sequence set forth in SEQ ID NO:21, and wherein the ORAI1 polypeptide comprises an amino acid sequence having at least 95% amino acid sequence identity to the amino acid sequence set forth in SEQ ID NO: 5;
   b) assaying the level of one or more of an ORAI1 gene product, a STIM1 gene product, and an NFAT1 gene product in the cell; and c) identifying a test agent that reduces the level of one or more of an ORAI1 gene product, a STIM1 gene product, and an NFAT1 gene product in the cell, compared to a control cell not contacted with the test agent, as a candidate agent for treating atopic dermatitis.

2. The method of claim 1, wherein the cell is a keratinocyte.

3. The method of claim 2, wherein the keratinocyte is a primary keratinocyte or a keratinocyte cell line.

4. The method of claim 1, wherein the cell is a mammalian cell line genetically modified to express PAR2 and ORAI1.

5. The method of claim 1, wherein the one or more of an ORAI1 gene product, a STIM1 gene product, and an NFAT1 gene product is an mRNA, and wherein the level of the mRNA is determined by a quantitative polymerase chain reaction.

6. The method of claim 1, wherein the one or more of an ORAI1 gene product, a STIM1 gene product, and an NFAT1 gene product in the cell is a polypeptide.

7. The method of claim 1, wherein the one or more of an ORAI1 gene product, a STIM1 gene product, and an NFAT1 gene product in the cell is determined using an immunological assay.

8. The method of claim 7, wherein the immunological assay is an enzyme-linked immunosorbent assay.

9. The method of claim 7, wherein the immunological assay is a radioimmunoassay.

10. The method of claim 7, wherein the immunological assay is a protein Western Blot.

11. The method of claim 7, wherein the immunological assay is an assay that detects a fusion partner of a fusion protein.

12. The method of claim 1, wherein assaying the level of the one or more of an ORAI1 gene product, a STIM1 gene product, and an NFAT1 gene product in the cell is determined by assessing the level of Thymic Stromal Lymphopoietin polypeptide (TSLP) TSLP produced by the cell.

13. The method of claim 12, wherein assessing the level of TSLP produced by the cell is carried out using a calcium-sensing dye.

14. The method of claim 12, wherein the test agent that reduces an intracellular calcium ion concentration in the cell is considered the candidate agent for treating atopic dermatitis.

15. The method of claim 1, wherein assaying the level of one or more of an ORAI1 gene product, a STIM1 gene product, and an NFAT1 gene product in the cell is determined by assessing the effect of the test agent on membrane depolarization, wherein a test agent that reduces membrane depolarization is considered a candidate agent for treating atopic dermatitis.

16. The method of claim 1, wherein the test agent is a nucleic acid agent.

17. The method of claim 16, wherein the nucleic acid agent is an antisense nucleic acid or a short interfering RNA.

18. The method of claim 17, wherein the nucleic acid agent comprises at least one modified nucleotide.

19. The method of claim 18, wherein the modified nucleotide is a 2'-deoxy-2'-fluoro modified nucleotide, a 2'-deoxy-modified nucleotide, a locked nucleotide, an abasic nucleotide, a 2'-ammo-modified nucleotide, a 2"-alkyl-modified nucleotide, a morpholino nucleotide, a phosphoramidate, or a non-natural base comprising nucleotide.

* * * * *

SEQUENCE LISTING

<160> NUMBER OF SEQ ID NOS: 25

<210> SEQ ID NO 1
<211> LENGTH: 371
<212> TYPE: PRT
<213> ORGANISM: Homo sapiens

<400> SEQUENCE: 1

```
Met Gly Arg Leu Val Leu Leu Trp Gly Ala Val Phe Leu Leu Gly
1               5                   10                  15

Gly Trp Met Ala Leu Gly Gln Gly Gly Ala Ala Glu Gly Val Gln Ile
                20                  25                  30

Gln Ile Ile Tyr Phe Asn Leu Glu Thr Val Gln Val Thr Trp Asn Ala
                35                  40                  45

Ser Lys Tyr Ser Arg Thr Asn Leu Thr Phe His Tyr Arg Phe Asn Gly
        50                  55                  60

Asp Glu Ala Tyr Asp Gln Cys Thr Asn Tyr Leu Leu Gln Glu Gly His
65                  70                  75                  80

Thr Ser Gly Cys Leu Leu Asp Ala Glu Gln Arg Asp Asp Ile Leu Tyr
                85                  90                  95

Phe Ser Ile Arg Asn Gly Thr His Pro Val Phe Thr Ala Ser Arg Trp
                100                 105                 110

Met Val Tyr Tyr Leu Lys Pro Ser Ser Pro Lys His Val Arg Phe Ser
                115                 120                 125

Trp His Gln Asp Ala Val Thr Val Thr Cys Ser Asp Leu Ser Tyr Gly
        130                 135                 140

Asp Leu Leu Tyr Glu Val Gln Tyr Arg Ser Pro Phe Asp Thr Glu Trp
145                 150                 155                 160

Gln Ser Lys Gln Glu Asn Thr Cys Asn Val Thr Ile Glu Gly Leu Asp
                165                 170                 175

Ala Glu Lys Cys Tyr Ser Phe Trp Val Arg Val Lys Ala Met Glu Asp
                180                 185                 190

Val Tyr Gly Pro Asp Thr Tyr Pro Ser Asp Trp Ser Glu Val Thr Cys
                195                 200                 205

Trp Gln Arg Gly Glu Ile Arg Asp Ala Cys Ala Glu Thr Pro Thr Pro
        210                 215                 220

Pro Lys Pro Lys Leu Ser Lys Phe Ile Leu Ile Ser Ser Leu Ala Ile
225                 230                 235                 240

Leu Leu Met Val Ser Leu Leu Leu Ser Leu Trp Lys Leu Trp Arg
                245                 250                 255

Val Lys Lys Phe Leu Ile Pro Ser Val Pro Asp Pro Lys Ser Ile Phe
                260                 265                 270

Pro Gly Leu Phe Glu Ile His Gln Gly Asn Phe Gln Glu Trp Ile Thr
                275                 280                 285

Asp Thr Gln Asn Val Ala His Leu His Lys Met Ala Gly Ala Glu Gln
                290                 295                 300
```

Glu Ser Gly Pro Glu Glu Pro Leu Val Val Gln Leu Ala Lys Thr Glu
305                 310                 315                 320

Ala Glu Ser Pro Arg Met Leu Asp Pro Gln Thr Glu Glu Lys Glu Ala
            325                 330                 335

Ser Gly Gly Ser Leu Gln Leu Pro His Gln Pro Leu Gln Gly Gly Asp
            340                 345                 350

Val Val Thr Ile Gly Gly Phe Thr Phe Val Met Asn Asp Arg Ser Tyr
        355                 360                 365

Val Ala Leu
    370

<210> SEQ ID NO 2
<211> LENGTH: 1116
<212> TYPE: DNA
<213> ORGANISM: Homo sapiens

<400> SEQUENCE: 2
atggggcggc tggttctgct gtggggagct gccgtctttc tgctgggagg ctggatggct      60
ttggggcaag gaggagcagc agaaggagta cagattcaga tcatctactt caatttagaa     120
accgtgcagg tgcatggaa tgccagcaaa tactccagga ccaacctgac tttccactac     180
agattcaacg gtgatgaggc ctatgaccag tgcaccaact accttctcca ggaaggtcac     240
acttcggggt gcctcctaga cgcagagcag cgagacgaca ttctctattt ctccatcagg     300
aatgggacgc accccgtttt caccgcaagt cgctggatgg tttattacct gaaacccagt     360
tccccgaagc acgtgagatt ttcgtggcat caggatgcag tgacggtgac gtgttctgac     420
ctgtcctacg gggatctcct ctatgaggtt cagtaccgga gcccttcga caccgagtgg     480 cagtccaaac aggaaaatac ctgcaacgtc accatagaag gcttggatgc cgagaagtgt     540
tactctttct gggtcagggt gaaggctatg gaggatgtat atgggccaga cacatacccca    600 agcgactggt cagaggtgac atgctggcag agaggcgaga ttcggatgc ctgtgcagag      660 acaccaacgc ctcccaaacc aaagctgtcc aaatttattt taatttccag cctggccatc     720
cttctgatgg tgtctctcct ccttctgtct ttatggaaat tatggagagt gaagaagttt     780
ctcattccca gcgtgccaga cccgaaatcc atcttccccg ggctctttga gatacaccaa     840
gggaacttcc aggagtggat cacagacacc cagaacgtgg cccacctcca agatggca      900 ggtgcagagc aagaaagtgg ccccgaggag ccctggtag tccagttggc caagactgaa      960
gccgagtctc ccaggatgct ggacccacag accgaggaga agaggcctc tggggatcc      1020 ctccagcttc cccaccagcc cctccaaggc ggtgatgtgg tcacaatcgg gggcttcacc    1080
tttgtgatga atgaccgctc ctacgtggcg ttgtga                              1116

<210> SEQ ID NO 3
<211> LENGTH: 1119
<212> TYPE: PRT
<213> ORGANISM: Homo sapiens

<400> SEQUENCE: 3

Met Lys Arg Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
                20                  25                  30

Lys Glu Ser Leu Lys Val Val Phe Glu Gly Ser Ala Tyr Gly Leu Gln
            35                  40                  45

Asn Phe Asn Lys Gln Lys Lys Leu Lys Arg Cys Asp Asp Met Asp Thr

```
            50                  55                  60
Phe Phe Leu His Tyr Ala Ala Glu Gly Gln Ile Glu Leu Met Glu
 65                  70                  75                  80

Lys Ile Thr Arg Asp Ser Ser Leu Glu Val Leu His Glu Met Asp Asp
                 85                  90                  95

Tyr Gly Asn Thr Pro Leu His Cys Ala Val Glu Lys Asn Gln Ile Glu
                100                 105                 110

Ser Val Lys Phe Leu Leu Ser Arg Gly Ala Asn Pro Asn Leu Arg Asn
            115                 120                 125

Phe Asn Met Met Ala Pro Leu His Ile Ala Val Gln Gly Met Asn Asn
130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                165                 170                 175

Asn Ser Glu Ala Leu Gln Ile Leu Leu Lys Lys Gly Ala Lys Pro Cys
            180                 185                 190

Lys Ser Asn Lys Trp Gly Cys Phe Pro Ile His Gln Ala Ala Phe Ser
            195                 200                 205

Gly Ser Lys Glu Cys Met Glu Ile Ile Leu Arg Phe Gly Glu Glu His
            210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
                245                 250                 255

Met Cys Leu Asp Asn Gly Ala Gln Ile Asp Pro Val Glu Lys Gly Arg
                260                 265                 270

Cys Thr Ala Ile His Phe Ala Ala Thr Gln Gly Ala Thr Glu Ile Val
            275                 280                 285

Lys Leu Met Ile Ser Ser Tyr Ser Gly Ser Val Asp Ile Val Asn Thr
290                 295                 300

Thr Asp Gly Cys His Glu Thr Met Leu His Arg Ala Ser Leu Phe Asp
305                 310                 315                 320

His His Glu Leu Ala Asp Tyr Leu Ile Ser Val Gly Ala Asp Ile Asn
                325                 330                 335

Lys Ile Asp Ser Glu Gly Arg Ser Pro Leu Ile Leu Ala Thr Ala Ser
            340                 345                 350

Ala Ser Trp Asn Ile Val Asn Leu Leu Leu Ser Lys Gly Ala Gln Val
            355                 360                 365

Asp Ile Lys Asp Asn Phe Gly Arg Asn Phe Leu His Leu Thr Val Gln
370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                405                 410                 415

Leu His Tyr Ala Cys Arg Gln Gly Gly Pro Gly Ser Val Asn Asn Leu
            420                 425                 430

Leu Gly Phe Asn Val Ser Ile His Ser Lys Ser Lys Asp Lys Lys Ser
            435                 440                 445

Pro Leu His Phe Ala Ala Ser Tyr Gly Arg Ile Asn Thr Cys Gln Arg
            450                 455                 460

Leu Leu Gln Asp Ile Ser Asp Thr Arg Leu Leu Asn Glu Gly Asp Leu
465                 470                 475                 480
```

```
His Gly Met Thr Pro Leu His Leu Ala Ala Lys Asn Gly His Asp Lys
                485                 490                 495

Val Val Gln Leu Leu Lys Lys Gly Ala Leu Phe Leu Ser Asp His
            500                 505                 510

Asn Gly Trp Thr Ala Leu His His Ala Ser Met Gly Gly Tyr Thr Gln
            515                 520                 525

Thr Met Lys Val Ile Leu Asp Thr Asn Leu Lys Cys Thr Asp Arg Leu
    530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys
            595                 600                 605

Leu Lys Ile Phe Ser His Asn Ser Pro Gly Asn Lys Cys Pro Ile Thr
    610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
            660                 665                 670

Thr Pro Thr Gln Asp Val Ile Tyr Glu Pro Leu Thr Ala Leu Asn Ala
            675                 680                 685

Met Val Gln Asn Asn Arg Ile Glu Leu Leu Asn His Pro Val Cys Lys
    690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
            755                 760                 765

Leu Ile Lys Thr Cys Met Ile Leu Val Phe Leu Ser Ser Ile Phe Gly
    770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
            835                 840                 845

Tyr Leu Gln Arg Phe Glu Asn Cys Gly Ile Phe Ile Val Met Leu Glu
    850                 855                 860

Val Ile Leu Lys Thr Leu Leu Arg Ser Thr Val Phe Ile Phe Leu
865                 870                 875                 880

Leu Leu Ala Phe Gly Leu Ser Phe Tyr Ile Leu Leu Asn Leu Gln Asp
                885                 890                 895
```

```
Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
        915                 920                 925

Asn Glu Leu Ala His Pro Val Leu Ser Phe Ala Gln Leu Val Ser Phe
        930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
            965                 970                 975

Ala Met Gln Val Glu Leu His Thr Ser Leu Glu Lys Lys Leu Pro Leu
        980                 985                 990

Trp Phe Leu Arg Lys Val Asp Gln Lys Ser Thr Ile Val Tyr Pro Asn
        995                 1000                1005

Lys Pro Arg Ser Gly Gly Met  Leu Phe His Ile Phe  Cys Phe Leu
    1010                1015                1020

Phe Cys Thr Gly Glu Ile Arg  Gln Glu Ile Pro Asn  Ala Asp Lys
    1025                1030                1035

Ser Leu Glu Met Glu Ile Leu  Lys Gln Lys Tyr Arg  Leu Lys Asp
    1040                1045                1050

Leu Thr Phe Leu Leu Glu Lys  Gln His Glu Leu Ile  Lys Leu Ile
    1055                1060                1065

Ile Gln Lys Met Glu Ile Ile  Ser Glu Thr Glu Asp  Asp Asp Ser
    1070                1075                1080

His Cys Ser Phe Gln Asp Arg  Phe Lys Lys Glu Gln  Met Glu Gln
    1085                1090                1095

Arg Asn Ser Arg Trp Asn Thr  Val Leu Arg Ala Val  Lys Ala Lys
    1100                1105                1110

Thr His His Leu Glu Pro
    1115

<210> SEQ ID NO 4
<211> LENGTH: 3360
<212> TYPE: DNA
<213> ORGANISM: Homo sapiens

<400> SEQUENCE: 4
atgaagcgca gcctgaggaa gatgtggcgc cctggagaaa agaaggagcc ccagggcgtt      60
gtctatgagg atgtgccgga cgacacggag gatttcaagg aatcgcttaa ggtggttttt     120
gaaggaagtg catatggatt acaaaacttt aataagcaaa agaaattaaa agatgtgacg     180
gatatggaca ccttcttctt gcattatgct gcagcagaag ccaaattga gctaatggag     240 aagatcacca gagattcctc tttggaagtg ctgcatgaaa tggatgatta tggaaatacc     300
cctctgcatt gtgctgtaga aaaaaaccaa attgaaagcg ttaagtttct tctcagcaga     360
ggagcaaacc caaatctccg aaacttcaac atgatggctc ctctccacat agctgtgcag     420
ggcatgaata atgaggtgat gaaggtcttg cttgagcata gaactattga tgttaatttg     480
gaaggagaaa atggaaacac agctgtgatc attgcgtgca ccacaaataa tagcgaagca     540
ttgcagattt tgcttaaaaa aggagctaag ccatgtaaat caaataaatg gggatgtttc     600
cctattcacc aagctgcatt ttcaggttcc aaagaatgca tggaaataat actaaggttt     660
ggtgaagagc atgggtacag tagacagttg cacattaact ttatgaataa tgggaaagcc     720
acccctctcc acctggctgt gcaaaatggt gacttggaaa tgatcaaaat gtgcctggac     780
```

```
aatggtgcac aaatagaccc agtggagaag ggaaggtgca cagccattca ttttgctgcc    840
acccagggag ccactgagat tgttaaactg atgatatcgt cctattctgg tagcgtggat    900
attgttaaca caaccgatgg atgtcatgag accatgcttc acagagcttc attgtttgat    960
caccatgagc tagcagacta tttaatttca gtgggagcag atattaataa gatcgattct   1020
gaaggacgct ctccacttat attagcaact gcttctgcat cttggaatat tgtaaatttg   1080
ctactctcta aaggtgccca agtagacata aagataatt ttggacgtaa ttttctgcat    1140
ttaactgtac agcaacctta tggattaaaa aatctgcgac ctgaatttat gcagatgcaa   1200
cagatcaaag agctggtaat ggatgaagac aacgatgggt gtactcctct acattatgca   1260
tgtagacagg ggggccctgg ttctgtaaat aacctacttg gctttaatgt gtccattcat   1320
tccaaaagca aagataagaa atcacctctg cattttgcag ccagttatgg gcgtatcaat   1380
acctgtcaga ggctcctaca agacataagt gatacgaggc ttctgaatga aggtgacctt   1440 catgaatga ctcctctcca tctggcagca agaatggac atgataaagt agttcagctt     1500
cttctgaaaa aaggtgcatt gtttctcagt gaccacaatg gctggacagc tttgcatcat   1560
gcgtccatgg gcgggtacac tcagaccatg aaggtcattc ttgatactaa tttgaagtgc   1620
acagatcgcc tggatgaaga cgggaacact gcacttcact tgctgcaag gaaggccac    1680 gccaaagccg ttgcgcttct tctgagccac aatgctgaca tagtcctgaa caagcagcag   1740
gcctcctttt tgcaccttgc acttcacaat aagaggaagg aggttgttct tacgatcatc   1800
aggagcaaaa gatgggatga atgtcttaag attttcagtc ataattctcc aggcaataaa   1860
tgtccaatta cagaaatgat agaataccctc cctgaatgca tgaaggtact tttagatttc   1920
tgcatgttgc attccacaga agacaagtcc tgccgagact attatatcga gtataatttc   1980
aaatatcttc aatgtccatt agaattcacc aaaaaaacac ctacacagga tgttatatat   2040
gaaccgctta cagccctcaa cgcaatggta caaaataacc gcatagagct tctcaatcat   2100
cctgtgtgta aagaatattt actcatgaaa tggttggctt atggatttag agctcatatg   2160
atgaatttag gatcttactg tcttggtctc atacctatga ccattctcgt tgtcaatata   2220
aaaccaggaa tggcttttcaa ctcaactggc atcatcaatg aaactagtga tcattcagaa   2280
atactagata ccacgaattc atatctaata aaaacttgta tgattttagt gttttttatca   2340 agtatatttg ggtattgcaa agaagcgggg caaatttcc aacagaaaag gaattatttt    2400
atggatataa gcaatgttct tgaatggatt atctacacga cgggcatcat ttttgtgctg   2460
cccttgtttg ttgaaatacc agctcatctg cagtggcaat gtggagcaat tgctgtttac   2520
ttctattgga tgaatttctt attgtatctt caaagatttg aaaattgtgg aattttttatt   2580 gttatgttgg aggtaatttt gaaactttg ttgaggtcta cagttgtatt tatcttcctt    2640
cttctggctt ttggactcag cttttacatc ctcctgaatt tacaggatcc cttcagctct   2700
ccattgcttt ctataatcca gaccttcagc atgatgctag gagatatcaa ttatcgagag   2760
tccttcctag aaccatatct gagaaatgaa ttggcacatc cagttctgtc ctttgcacaa   2820
cttgtttcct tcacaatatt tgtcccaatt gtcctcatga atttacttat tggtttggca   2880
gttggcgaca ttgctgaggt ccagaaacat gcatcattga gaggatagc tatgcaggtg   2940 gaacttcata ccagcttaga aagaagctg ccactttggt ttctacgcaa agtggatcag   3000
aaatccacca tcgtgtatcc caacaaaccc agatctggtg ggatgttatt ccatatattc   3060
tgttttttat tttgcactgg ggaaataaga caagaaatac caaatgctga taaatctta    3120 gaaatggaaa tattaaagca gaaataccgg ctgaaggatc ttacttttct cctggaaaaa   3180
```

```
cagcatgagc tcattaaact gatcattcag aagatggaga tcatctctga gacagaggat    3240
gatgatagcc attgttcttt tcaagacagg tttaagaaag agcagatgga acaaggaat     3300 agcagatgga atactgtgtt gagagcagtc aaggcaaaaa cacaccatct tgagccttag    3360
```

<210> SEQ ID NO 5
<211> LENGTH: 301
<212> TYPE: PRT
<213> ORGANISM: Homo sapiens

<400> SEQUENCE: 5

```
Met His Pro Glu Pro Ala Pro Pro Ser Arg Ser Ser Pro Glu Leu
1               5                   10                  15

Pro Pro Ser Gly Gly Ser Thr Thr Ser Gly Ser Arg Arg Ser Arg Arg
                20                  25                  30

Arg Ser Gly Asp Gly Glu Pro Pro Gly Ala Pro Pro Pro Pro Ser
            35                  40                  45

Ala Val Thr Tyr Pro Asp Trp Ile Gly Gln Ser Tyr Ser Glu Val Met
    50                  55                  60

Ser Leu Asn Glu His Ser Met Gln Ala Leu Ser Trp Arg Lys Leu Tyr
65                  70                  75                  80

Leu Ser Arg Ala Lys Leu Lys Ala Ser Ser Arg Thr Ser Ala Leu Leu
                85                  90                  95

Ser Gly Phe Ala Met Val Ala Met Val Glu Val Gln Leu Asp Ala Asp
            100                 105                 110

His Asp Tyr Pro Pro Gly Leu Leu Ile Ala Phe Ser Ala Cys Thr Thr
        115                 120                 125

Val Leu Val Ala Val His Leu Phe Ala Leu Met Ile Ser Thr Cys Ile
130                 135                 140

Leu Pro Asn Ile Glu Ala Val Ser Asn Val His Asn Leu Asn Ser Val
145                 150                 155                 160

Lys Glu Ser Pro His Glu Arg Met His Arg His Ile Glu Leu Ala Trp
                165                 170                 175

Ala Phe Ser Thr Val Ile Gly Thr Leu Leu Phe Leu Ala Glu Val Val
            180                 185                 190

Leu Leu Cys Trp Val Lys Phe Leu Pro Leu Lys Lys Gln Pro Gly Gln
        195                 200                 205

Pro Arg Pro Thr Ser Lys Pro Pro Ala Ser Gly Ala Ala Ala Asn Val
    210                 215                 220

Ser Thr Ser Gly Ile Thr Pro Gly Gln Ala Ala Ala Ile Ala Ser Thr
225                 230                 235                 240

Thr Ile Met Val Pro Phe Gly Leu Ile Phe Ile Val Phe Ala Val His
                245                 250                 255

Phe Tyr Arg Ser Leu Val Ser His Lys Thr Asp Arg Gln Phe Gln Glu
            260                 265                 270

Leu Asn Glu Leu Ala Glu Phe Ala Arg Leu Gln Asp Gln Leu Asp His
        275                 280                 285

Arg Gly Asp His Pro Leu Thr Pro Gly Ser His Tyr Ala
    290                 295                 300
```

<210> SEQ ID NO 6
<211> LENGTH: 906
<212> TYPE: DNA
<213> ORGANISM: Homo sapiens

<400> SEQUENCE: 6

-continued

```
atgcatccgg agcccgcccc gcccccgagc cgcagcagtc ccgagcttcc cccaagcggc      60
ggcagcacca ccagcggcag ccgccggagc cgccgccgca gcggggacgg ggagcccccg     120
ggggccccgc accgccgcc gtccgccgtc acctacccgg actggatcgg ccagagttac     180
tccgaggtga tgagcctcaa cgagcactcc atgcaggcgc tgtcctggcg caagctctac    240
ttgagccgcg ccaagcttaa agcctccagc cggacctcgg ctctgctctc cggcttcgcc    300
atggtggcaa tggtggaggt gcagctggac gctgaccacg actacccacc ggggctgctc    360
atcgccttca gtgcctgcac cacagtgctg gtggctgtgc acctgtttgc gctcatgatc    420
agcacctgca tcctgcccaa catcgaggcg tgagcaacg tgcacaatct caactcggtc    480
aaggagtccc cccatgagcg catgcaccgc cacatcgagc tggcctgggc cttctccacc    540
gtcatcggca cgctgctctt cctagctgag gtggtgctgc tctgctgggt caagttcttg    600
cccctcaaga agcagccagg ccagccaagg cccaccagca agcccccgc cagtggcgca    660
gcagccaacg tcagcaccag cggcatcacc ccgggccagg cagctgccat cgcctcgacc    720
accatcatgg tgcccttcgg cctgatcttt atcgtcttcg ccgtccactt ctaccgctca    780
ctggttagcc ataagactga ccacagttc caggagctca cgagctggc ggagtttgcc    840
cgcttacagg accagctgga ccacagaggg gaccacccc tgacgcccgg cagccactat    900
gcctag                                                               906
```

<210> SEQ ID NO 7
<211> LENGTH: 254
<212> TYPE: PRT
<213> ORGANISM: Homo sapiens

<400> SEQUENCE: 7

```
Met Ser Ala Glu Leu Asn Val Pro Ile Asp Pro Ser Ala Pro Ala Cys
1               5                   10                  15

Pro Glu Pro Gly His Lys Gly Met Asp Tyr Arg Asp Trp Val Arg Arg
            20                  25                  30

Ser Tyr Leu Glu Leu Val Thr Ser Asn His His Ser Val Gln Ala Leu
        35                  40                  45

Ser Trp Arg Lys Leu Tyr Leu Ser Arg Ala Lys Leu Lys Ala Ser Ser
    50                  55                  60

Arg Thr Ser Ala Leu Leu Ser Gly Phe Ala Met Val Ala Met Val Glu
65                  70                  75                  80

Val Gln Leu Glu Thr Gln Tyr Gln Tyr Pro Arg Pro Leu Leu Ile Ala
                85                  90                  95

Phe Ser Ala Cys Thr Thr Val Leu Val Ala Val His Leu Phe Ala Leu
            100                 105                 110

Leu Ile Ser Thr Cys Ile Leu Pro Asn Val Glu Ala Val Ser Asn Ile
        115                 120                 125

His Asn Leu Asn Ser Ile Ser Glu Ser Pro His Glu Arg Met His Pro
    130                 135                 140

Tyr Ile Glu Leu Ala Trp Gly Phe Ser Thr Val Leu Gly Ile Leu Leu
145                 150                 155                 160

Phe Leu Ala Glu Val Val Leu Leu Cys Trp Ile Lys Phe Leu Pro Val
                165                 170                 175

Asp Ala Arg Arg Gln Pro Gly Pro Pro Gly Pro Gly Ser His Thr
            180                 185                 190

Gly Trp Gln Ala Ala Leu Val Ser Thr Ile Ile Met Val Pro Val Gly
        195                 200                 205
```

Leu Ile Phe Val Val Phe Thr Ile His Phe Tyr Arg Ser Leu Val Arg
    210                 215                 220

His Lys Thr Glu Arg His Asn Arg Glu Ile Glu Glu Leu His Lys Leu
225                 230                 235                 240

Lys Val Gln Leu Asp Gly His Glu Arg Ser Leu Gln Val Leu
                245                 250

<210> SEQ ID NO 8
<211> LENGTH: 177
<212> TYPE: PRT
<213> ORGANISM: Homo sapiens

<400> SEQUENCE: 8

Met Val Glu Val Gln Leu Glu Thr Gln Tyr Gln Tyr Pro Arg Pro Leu
1               5                   10                  15

Leu Ile Ala Phe Ser Ala Cys Thr Thr Val Leu Val Ala Val His Leu
                20                  25                  30

Phe Ala Leu Leu Ile Ser Thr Cys Ile Leu Pro Asn Val Glu Ala Val
            35                  40                  45

Ser Asn Ile His Asn Leu Asn Ser Ile Ser Glu Ser Pro His Glu Arg
    50                  55                  60

Met His Pro Tyr Ile Glu Leu Ala Trp Gly Phe Ser Thr Val Leu Gly
65                  70                  75                  80

Ile Leu Leu Phe Leu Ala Glu Val Val Leu Leu Cys Trp Ile Lys Phe
                85                  90                  95

Leu Pro Val Asp Ala Arg Arg Gln Pro Gly Pro Pro Gly Pro Gly
                100                 105                 110

Ser His Thr Gly Trp Gln Ala Ala Leu Val Ser Thr Ile Ile Met Val
            115                 120                 125

Pro Val Gly Leu Ile Phe Val Val Phe Thr Ile His Phe Tyr Arg Ser
    130                 135                 140

Leu Val Arg His Lys Thr Glu Arg His Asn Arg Glu Ile Glu Glu Leu
145                 150                 155                 160

His Lys Leu Lys Val Gln Leu Asp Gly His Glu Arg Ser Leu Gln Val
                165                 170                 175

Leu

<210> SEQ ID NO 9
<211> LENGTH: 765
<212> TYPE: DNA
<213> ORGANISM: Homo sapiens

<400> SEQUENCE: 9
atgagtgctg agcttaacgt gcctatcgac ccctctgctc ctgcctgccc tgagcccggc      60
cataagggca tggattaccg ggactgggtc cgccgcagct acctggaact ggtcacctct     120
aaccaccact cggtacaggc cctgtcgtgg cggaagctct acctgagcag gccaagctg      180 aaggcctcca gcaggacctc cgccctcctc tccggctttg ccatggtggc catggtggag     240
gtgcagctgg agacgcagta ccagtacccg cggccgctgc tgattgcctt cagcgcctgc     300
accacggtgc tggtggccgt gcacctgttc gcctcctca tcagcacctg catcctgccc      360
aatgtggagg ccgtgagcaa catccacaac ctgaactcca tcagcgagtc ccgcatgag      420 cgcatgcacc cctacatcga gctggcctgg ggcttctcca ccgtgcttgg catcctactc     480
ttcctggccg aggtggtgct gctctgctgg atcaagttcc tccccgtgga tgcccggcgc     540

```
cagcctggcc ccccacctgg ccctgggagt cacacgggct ggcaggccgc cctggtgtcc      600
accatcatca tggtgcccgt gggcctcatc ttcgtggtct tcaccatcca cttctaccgc      660
tccctggtgc gccacaaaac ggagcgccac aaccgcgaga tcgaggagct ccacaagctc      720
aaggtccagc tggacgggca tgagcgcagc ctgcaggtct tgtga                     765

<210> SEQ ID NO 10
<211> LENGTH: 534
<212> TYPE: DNA
<213> ORGANISM: Homo sapiens

<400> SEQUENCE: 10
atggtggagg tgcagctgga gacgcagtac cagtacccgc ggccgctgct gattgccttc       60
agcgcctgca ccacggtgct ggtggccgtg cacctgttcg ccctcctcat cagcacctgc      120
atcctgccca atgtggaggc cgtgagcaac atccacaacc tgaactccat cagcgagtcc      180
ccgcatgagc gcatgcaccc ctacatcgag ctggcctggg gcttctccac cgtgcttggc      240
atcctactct tcctggccga ggtggtgctg ctctgctgga tcaagttcct ccccgtggat      300
gcccggcgcc agcctggccc ccacctggcc ctgggagtc acacgggctg gcaggccgcc      360
ctggtgtcca ccatcatcat ggtgcccgtg ggcctcatct tcgtggtctt caccatccac      420
ttctaccgct ccctggtgcg ccacaaaacg gagcgccaca accgcgagat cgaggagctc      480
cacaagctca aggtccagct ggacgggcat gagcgcagcc tgcaggtctt gtga            534

<210> SEQ ID NO 11
<211> LENGTH: 791
<212> TYPE: PRT
<213> ORGANISM: Homo sapiens

<400> SEQUENCE: 11
```

Met Asp Val Cys Val Arg Leu Ala Leu Trp Leu Leu Trp Gly Leu Leu
1               5                   10                  15

Leu His Gln Gly Gln Ser Leu Ser His Ser His Ser Glu Lys Ala Thr
            20                  25                  30

Gly Thr Ser Ser Gly Ala Asn Ser Glu Glu Ser Thr Ala Ala Glu Phe
        35                  40                  45

Cys Arg Ile Asp Lys Pro Leu Cys His Ser Glu Asp Glu Lys Leu Ser
    50                  55                  60

Phe Glu Ala Val Arg Asn Ile His Lys Leu Met Asp Asp Asp Ala Asn
65                  70                  75                  80

Gly Asp Val Asp Val Glu Glu Ser Asp Glu Phe Leu Arg Glu Asp Leu
                85                  90                  95

Asn Tyr His Asp Pro Thr Val Lys His Ser Thr Phe His Gly Glu Asp
            100                 105                 110

Lys Leu Ile Ser Val Glu Asp Leu Trp Lys Ala Trp Lys Ser Ser Glu
        115                 120                 125

Val Tyr Asn Trp Thr Val Asp Glu Val Val Gln Trp Leu Ile Thr Tyr
    130                 135                 140

Val Glu Leu Pro Gln Tyr Glu Glu Thr Phe Arg Lys Leu Gln Leu Ser
145                 150                 155                 160

Gly His Ala Met Pro Arg Leu Ala Val Thr Asn Thr Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Leu Thr Arg His

-continued

```
            195                 200                 205
Asn His Leu Lys Asp Phe Met Leu Val Val Ser Ile Val Ile Gly Val
210                 215                 220
Gly Gly Cys Trp Phe Ala Tyr Ile Gln Asn Arg Tyr Ser Lys Glu His
225                 230                 235                 240
Met Lys Lys Met Met Lys Asp Leu Glu Gly Leu His Arg Ala Glu Gln
                245                 250                 255
Ser Leu His Asp Leu Gln Glu Arg Leu His Lys Ala Gln Glu Glu His
            260                 265                 270
Arg Thr Val Glu Val Glu Lys Val His Leu Glu Lys Lys Leu Arg Asp
        275                 280                 285
Glu Ile Asn Leu Ala Lys Gln Glu Ala Gln Arg Leu Lys Glu Leu Arg
290                 295                 300
Glu Gly Thr Glu Asn Glu Arg Ser Arg Gln Lys Tyr Ala Glu Glu Glu
305                 310                 315                 320
Leu Glu Gln Val Arg Glu Ala Leu Arg Lys Ala Glu Lys Glu Leu Glu
                325                 330                 335
Ser His Ser Ser Trp Tyr Ala Pro Glu Ala Leu Gln Lys Trp Leu Gln
            340                 345                 350
Leu Thr His Glu Val Glu Val Gln Tyr Tyr Asn Ile Lys Lys Gln Asn
        355                 360                 365
Ala Glu Lys Gln Leu Leu Val Ala Lys Glu Gly Ala Glu Lys Ile Lys
370                 375                 380
Lys Lys Arg Asn Thr Leu Phe Gly Thr Phe His Val Ala His Ser Ser
385                 390                 395                 400
Ser Leu Asp Asp Val Asp His Lys Ile Leu Thr Ala Lys Gln Ala Leu
                405                 410                 415
Ser Glu Val Thr Ala Ala Leu Arg Glu Arg Leu His Arg Trp Gln Gln
            420                 425                 430
Ile Glu Ile Leu Cys Gly Phe Gln Ile Val Asn Asn Pro Gly Ile His
        435                 440                 445
Ser Leu Val Ala Ala Leu Asn Ile Asp Pro Ser Trp Met Gly Ser Thr
450                 455                 460
Arg Pro Asn Pro Ala His Phe Ile Met Thr Asp Asp Val Asp Asp Met
465                 470                 475                 480
Asp Glu Glu Ile Val Ser Pro Leu Ser Met Gln Ser Pro Ser Leu Gln
                485                 490                 495
Ser Ser Val Arg Gln Arg Leu Thr Glu Pro Gln His Gly Leu Gly Ser
            500                 505                 510
Gln Arg Leu Val Glu Gly Glu Ala Gly His Phe Leu Thr Ser Arg Val
        515                 520                 525
Ser Leu Arg Arg Met Arg Ser Leu Ser Ser Gly Gln Ser Phe Ser Ser
530                 535                 540
Glu Gly Tyr Gly Thr Ser Ser Pro Ser Ala Ser Ala Ala Ser Cys
545                 550                 555                 560
Ser Ser Ser Ile Thr Thr Ile Thr Thr Thr Thr Thr Thr Thr Thr
                565                 570                 575
Phe Thr Thr Val His Val His Pro Val Tyr Tyr His Ser Thr Ser
            580                 585                 590
Tyr Phe Leu Gln Met Glu Pro Tyr Pro Asp Thr Pro Pro Ser Asp Ser
        595                 600                 605
Thr Ala Val Met Pro Gly His Ser Glu Ser Leu Gly Asp Leu Thr His
610                 615                 620
```

Ser Asp Ser Glu Ser Ser Leu His Met Ser Asp Arg Gln Arg Val Ala
625                 630                 635                 640

Pro Lys Pro Pro Gln Met Ser Arg Ala Ala Asp Glu Ala Leu Asn Ala
            645                 650                 655

Met Thr Ser Asn Gly Ser His Arg Leu Ile Glu Gly Val His Pro Gly
        660                 665                 670

Ser Leu Val Glu Lys Leu Pro Asp Ser Pro Ala Leu Ala Lys Lys Ala
    675                 680                 685

Leu Leu Ala Leu Asn His Gly Leu Asp Lys Ala His Ser Leu Met Glu
690                 695                 700

Leu Ser Pro Ser Ala Pro Pro Gly Gly Ser Pro His Leu Asp Ser Ser
705                 710                 715                 720

Arg Ser His Ser Pro Ser Pro Asp Pro Asp Thr Pro Ser Pro Val
                725                 730                 735

Gly Asp Ser Arg Ala Leu Gln Ala Ser Arg Asn Thr Arg Ile Pro His
            740                 745                 750

Leu Ala Gly Lys Lys Ala Val Ala Glu Glu Asp Asn Gly Ser Ile Gly
        755                 760                 765

Glu Glu Thr Asp Ser Ser Pro Gly Arg Lys Lys Phe Pro Leu Lys Ile
770                 775                 780

Phe Lys Lys Pro Leu Lys Lys
785                 790

<210> SEQ ID NO 12
<211> LENGTH: 685
<212> TYPE: PRT
<213> ORGANISM: Homo sapiens

<400> SEQUENCE: 12

Met Asp Val Cys Val Arg Leu Ala Leu Trp Leu Leu Trp Gly Leu Leu
1               5                   10                  15

Leu His Gln Gly Gln Ser Leu Ser His Ser His Ser Glu Lys Ala Thr
            20                  25                  30

Gly Thr Ser Ser Gly Ala Asn Ser Glu Glu Ser Thr Ala Ala Glu Phe
        35                  40                  45

Cys Arg Ile Asp Lys Pro Leu Cys His Ser Glu Asp Glu Lys Leu Ser
    50                  55                  60

Phe Glu Ala Val Arg Asn Ile His Lys Leu Met Asp Asp Asp Ala Asn
65                  70                  75                  80

Gly Asp Val Asp Val Glu Glu Ser Asp Glu Phe Leu Arg Glu Asp Leu
                85                  90                  95

Asn Tyr His Asp Pro Thr Val Lys His Ser Thr Phe His Gly Glu Asp
            100                 105                 110

Lys Leu Ile Ser Val Glu Asp Leu Trp Lys Ala Trp Lys Ser Ser Glu
        115                 120                 125

Val Tyr Asn Trp Thr Val Asp Glu Val Val Gln Trp Leu Ile Thr Tyr
    130                 135                 140

Val Glu Leu Pro Gln Tyr Glu Glu Thr Phe Arg Lys Leu Gln Leu Ser
145                 150                 155                 160

Gly His Ala Met Pro Arg Leu Ala Val Thr Asn Thr Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Leu Thr Arg His

-continued

```
            195                 200                 205
Asn His Leu Lys Asp Phe Met Leu Val Val Ser Ile Val Ile Gly Val
210                 215                 220
Gly Gly Cys Trp Phe Ala Tyr Ile Gln Asn Arg Tyr Ser Lys Glu His
225                 230                 235                 240
Met Lys Lys Met Met Lys Asp Leu Glu Gly Leu His Arg Ala Glu Gln
                245                 250                 255
Ser Leu His Asp Leu Gln Glu Arg Leu His Lys Ala Gln Glu Glu His
            260                 265                 270
Arg Thr Val Glu Val Glu Lys Val His Leu Glu Lys Lys Leu Arg Asp
        275                 280                 285
Glu Ile Asn Leu Ala Lys Gln Glu Ala Gln Arg Leu Lys Glu Leu Arg
290                 295                 300
Glu Gly Thr Glu Asn Glu Arg Ser Arg Gln Lys Tyr Ala Glu Glu Glu
305                 310                 315                 320
Leu Glu Gln Val Arg Glu Ala Leu Arg Lys Ala Glu Lys Glu Leu Glu
                325                 330                 335
Ser His Ser Ser Trp Tyr Ala Pro Glu Ala Leu Gln Lys Trp Leu Gln
            340                 345                 350
Leu Thr His Glu Val Glu Val Gln Tyr Tyr Asn Ile Lys Lys Gln Asn
        355                 360                 365
Ala Glu Lys Gln Leu Leu Val Ala Lys Glu Gly Ala Glu Lys Ile Lys
370                 375                 380
Lys Lys Arg Asn Thr Leu Phe Gly Thr Phe His Val Ala His Ser Ser
385                 390                 395                 400
Ser Leu Asp Asp Val Asp His Lys Ile Leu Thr Ala Lys Gln Ala Leu
                405                 410                 415
Ser Glu Val Thr Ala Ala Leu Arg Glu Arg Leu His Arg Trp Gln Gln
            420                 425                 430
Ile Glu Ile Leu Cys Gly Phe Gln Ile Val Asn Asn Pro Gly Ile His
        435                 440                 445
Ser Leu Val Ala Ala Leu Asn Ile Asp Pro Ser Trp Met Gly Ser Thr
450                 455                 460
Arg Pro Asn Pro Ala His Phe Ile Met Thr Asp Asp Val Asp Asp Met
465                 470                 475                 480
Asp Glu Glu Ile Val Ser Pro Leu Ser Met Gln Ser Pro Ser Leu Gln
                485                 490                 495
Ser Ser Val Arg Gln Arg Leu Thr Glu Pro Gln His Gly Leu Gly Ser
            500                 505                 510
Gln Arg Asp Leu Thr His Ser Asp Ser Glu Ser Ser Leu His Met Ser
        515                 520                 525
Asp Arg Gln Arg Val Ala Pro Lys Pro Pro Gln Met Ser Arg Ala Ala
530                 535                 540
Asp Glu Ala Leu Asn Ala Met Thr Ser Asn Gly Ser His Arg Leu Ile
545                 550                 555                 560
Glu Gly Val His Pro Gly Ser Leu Val Glu Lys Leu Pro Asp Ser Pro
                565                 570                 575
Ala Leu Ala Lys Lys Ala Leu Leu Ala Leu Asn His Gly Leu Asp Lys
            580                 585                 590
Ala His Ser Leu Met Glu Leu Ser Pro Ser Ala Pro Pro Gly Gly Ser
        595                 600                 605
Pro His Leu Asp Ser Ser Arg Ser His Ser Pro Ser Pro Asp Pro
610                 615                 620
```

Asp Thr Pro Ser Pro Val Gly Asp Ser Arg Ala Leu Gln Ala Ser Arg
625                 630                 635                 640

Asn Thr Arg Ile Pro His Leu Ala Gly Lys Lys Ala Val Ala Glu Glu
            645                 650                 655

Asp Asn Gly Ser Ile Gly Glu Glu Thr Asp Ser Ser Pro Gly Arg Lys
            660                 665                 670

Lys Phe Pro Leu Lys Ile Phe Lys Pro Leu Lys Lys
        675                 680                 685

<210> SEQ ID NO 13
<211> LENGTH: 540
<212> TYPE: PRT
<213> ORGANISM: Homo sapiens

<400> SEQUENCE: 13

Met Asp Val Cys Val Arg Leu Ala Leu Trp Leu Leu Trp Gly Leu Leu
1               5                   10                  15

Leu His Gln Gly Gln Ser Leu Ser His Ser His Ser Glu Lys Ala Thr
            20                  25                  30

Gly Thr Ser Ser Gly Ala Asn Ser Glu Glu Ser Thr Ala Ala Glu Phe
        35                  40                  45

Cys Arg Ile Asp Lys Pro Leu Cys His Ser Glu Asp Glu Lys Leu Ser
    50                  55                  60

Phe Glu Ala Val Arg Asn Ile His Lys Leu Met Asp Asp Ala Asn
65                  70                  75                  80

Gly Asp Val Asp Val Glu Glu Ser Asp Glu Phe Leu Arg Glu Asp Leu
                85                  90                  95

Asn Tyr His Asp Pro Thr Val Lys His Ser Thr Phe His Gly Glu Asp
            100                 105                 110

Lys Leu Ile Ser Val Glu Asp Leu Trp Lys Ala Trp Lys Ser Ser Glu
        115                 120                 125

Val Tyr Asn Trp Thr Val Asp Glu Val Val Gln Trp Leu Ile Thr Tyr
    130                 135                 140

Val Glu Leu Pro Gln Tyr Glu Glu Thr Phe Arg Lys Leu Gln Leu Ser
145                 150                 155                 160

Gly His Ala Met Pro Arg Leu Ala Val Thr Asn Thr Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Leu Thr Arg His
        195                 200                 205

Asn His Leu Lys Asp Phe Met Leu Val Val Ser Ile Val Ile Gly Val
    210                 215                 220

Gly Gly Cys Trp Phe Ala Tyr Ile Gln Asn Arg Tyr Ser Lys Glu His
225                 230                 235                 240

Met Lys Lys Met Met Lys Asp Leu Glu Gly Leu His Arg Ala Glu Gln
                245                 250                 255

Ser Leu His Asp Leu Gln Glu Arg Leu His Lys Ala Gln Glu Glu His
            260                 265                 270

Arg Thr Val Glu Val Glu Lys Val His Leu Glu Lys Lys Leu Arg Asp
        275                 280                 285

Glu Ile Asn Leu Ala Lys Gln Glu Ala Gln Arg Leu Lys Glu Leu Arg
    290                 295                 300

Glu Gly Thr Glu Asn Glu Arg Ser Arg Gln Lys Tyr Ala Glu Glu Glu

```
                    305                 310                 315                 320
Leu Glu Gln Val Arg Glu Ala Leu Arg Lys Ala Glu Lys Leu Glu
                325                 330                 335

Ser His Ser Ser Trp Tyr Ala Pro Glu Ala Leu Gln Lys Trp Leu Gln
            340                 345                 350

Leu Thr His Glu Val Glu Val Gln Tyr Tyr Asn Ile Lys Lys Gln Asn
        355                 360                 365

Ala Glu Lys Gln Leu Leu Val Ala Lys Glu Gly Ala Glu Lys Ile Lys
    370                 375                 380

Lys Lys Arg Asn Thr Leu Phe Gly Thr Phe His Val Ala His Ser Ser
385                 390                 395                 400

Ser Leu Asp Asp Val Asp His Lys Ile Leu Thr Ala Lys Gln Ala Leu
                405                 410                 415

Ser Glu Val Thr Ala Ala Leu Arg Glu Arg Leu His Arg Trp Gln Gln
            420                 425                 430

Ile Glu Ile Leu Cys Gly Phe Gln Ile Val Asn Asn Pro Gly Ile His
        435                 440                 445

Ser Leu Val Ala Ala Leu Asn Ile Asp Pro Ser Trp Met Gly Ser Thr
    450                 455                 460

Arg Pro Asn Pro Ala His Phe Ile Met Thr Asp Asp Val Asp Asp Met
465                 470                 475                 480

Asp Glu Glu Ile Val Ser Pro Leu Ser Met Gln Ser Pro Ser Leu Gln
                485                 490                 495

Ser Ser Val Arg Gln Arg Leu Thr Glu Pro Gln His Gly Leu Gly Ser
            500                 505                 510

Gln Arg Gly Ser Ser Leu Lys Ala Asn Arg Leu Ser Ser Lys Gly Phe
        515                 520                 525

Asp Pro Phe Arg Phe Gly Val Leu Pro Pro His Glu
    530                 535                 540

<210> SEQ ID NO 14
<211> LENGTH: 2376
<212> TYPE: DNA
<213> ORGANISM: Homo sapiens

<400> SEQUENCE: 14
atggatgtat gcgtccgtct tgccctgtgg ctcctctggg gactcctcct gcaccagggc    60
cagagcctca gccatagtca cagtgagaag gcgacaggaa ccagctcggg ggccaactct   120
gaggagtcca ctgcagcaga gttttgccga attgacaagc ccctgtgtca cagtgaggat   180
gagaaactca gcttcgaggc agtccgtaac atccacaaac tgatggacga tgatgccaat   240
ggtgatgtgg atgtggaaga agtgatgag ttcctgaggg aagacctcaa ttaccatgac    300
ccaacagtga aacacagcac cttccatggt gaggataagc tcatcagcgt ggaggacctg   360
tggaaggcat ggaagtcatc agaagtatac aattggaccg tggatgaggt ggtacagtgg   420
ctgatcacat atgtggagct gcctcagtat gaggagacct tccggaagct gcagctcagt   480
ggccatgcca tgccaaggct ggctgtcacc aacaccacca tgacagggac tgtgctgaag   540
atgacagacc ggagtcatcg gcagaagctg cagctgaagg ctctggatac agtgctcttt   600
gggcctcctc tcttgactcg ccataatcac ctcaaggact tcatgctggt ggtgtctatc   660
gttattggtg tgggcggctg ctggtttgcc tatatccaga accgttactc aaggagcac    720 atgaagaaga tgatgaagga cttggagggg ttacaccgag ctgagcagag tctgcatgac   780
cttcaggaaa ggctgcacaa ggcccaggag gagcaccgca cagtggaggt ggagaaggtc   840
```

-continued

```
catctggaaa agaagctgcg cgatgagatc aaccttgcta agcaggaagc ccagcggctg      900
aaggagctgc gggagggtac tgagaatgag cggagccgcc aaaaatatgc tgaggaggag      960
ttggagcagg ttcgggaggc cttgaggaaa gcagagaagg agctagaatc tcacagctca     1020
tggtatgctc cagaggccct tcagaagtgg ctgcagctga cacatgaggt ggaggtgcaa     1080
tattacaaca tcaagaagca aaatgctgag aagcagctgc tggtggccaa ggagggggct     1140
gagaagataa aaagaagag aaacacactc tttggcacct ccacgtggc ccacagctct      1200
tccctggatg atgtagatca taaaattcta acagctaagc aagcactgag cgaggtgaca     1260
gcagcattgc gggagcgcct gcaccgctgg caacagatcg agatcctctg tggcttccag     1320
attgtcaaca accctggcat ccactcactg gtggctgccc tcaacataga ccccagctgg     1380
atgggcagta cacgccccaa ccctgctcac ttcatcatga ctgacgacgt ggatgacatg     1440
gatgaggaga ttgtgtctcc cttgtccatg cagtccccta gcctgcagag cagtgttcgg     1500
cagcgcctga cggagccaca gcatggcctg ggatctcaga ggttggtaga gggcgaggct     1560
ggccacttct tgacaagccg ggtatctctg cggcgaatgc gcagcctttc atctggacag     1620
tctttcagtt ctgaaggcta cgggaccagc tctccatctg cctctgctgc tgcttcttgc     1680
tcctcttcca tcaccaccat caccactacc accaccacca ccaccacctt caccaccgtc     1740
catgtccacc ctgtttatta ccaccacagc acttcctatt tcctccagat ggagccctac     1800
cctgacacac ccccttctga cagcaccgct gtgatgcctg ggcattcaga gagcttgggg     1860
gatttgaccc attccgattc ggagtcctcc ctccacatga gtgaccgcca gcgtgtggcc     1920
cccaaacctc ctcagatgag ccgtgctgca gacgaggctc tcaatgccat gacttccaat     1980
ggcagccacc ggctgatcga gggggtccac ccagggtctc tggtggagaa actgcctgac     2040
agccctgccc tggccaagaa ggcattactg gcgctgaacc atgggctgga caaggcccac     2100
agcctgatgg agctgagccc ctcagcccca cctggtggct ctccacattt ggattcttcc     2160
cgttctcaca gccccagctc cccagaccca gacacaccat ctccagttgg ggacagccga     2220
gccctgcaag ccagccgaaa cacacgcatt ccccacctgg ctggcaagaa ggctgtggct     2280
gaggaggata atggctctat tggcgaggaa acagactcca gcccaggccg gaagaagttt     2340
cccctcaaaa tctttaagaa gcctcttaag aagtag                              2376
```

<210> SEQ ID NO 15
<211> LENGTH: 2058
<212> TYPE: DNA
<213> ORGANISM: Homo sapiens

<400> SEQUENCE: 15

```
atggatgtat gcgtccgtct tgccctgtgg ctcctctggg gactcctcct gcaccagggc       60
cagagcctca gccatagtca cagtgagaag gcgacaggaa ccagctcggg ggccaactct      120
gaggagtcca ctgcagcaga gttttgccga attgacaagc ccctgtgtca cagtgaggat      180
gagaaactca gcttcgaggc agtccgtaac atccacaaac tgatggacga tgatgccaat      240
ggtgatgtgg atgtggaaga agtgatgag ttcctgaggg aagacctcaa ttaccatgac      300
ccaacagtga aacacagcac cttccatggt gaggataagc tcatcagcgt ggaggacctg      360
tggaaggcat ggaagtcatc agaagtatac aattggaccg tggatgaggt ggtacagtgg      420
ctgatcacat atgtggagct gcctcagtat gaggagacct tccggaagct gcagctcagt      480
ggccatgcca tgccaaggct ggctgtcacc aacaccacca tgacagggac tgtgctgaag      540
```

```
atgacagacc ggagtcatcg gcagaagctg cagctgaagg ctctggatac agtgctcttt    600
gggcctcctc tcttgactcg ccataatcac ctcaaggact tcatgctggt ggtgtctatc    660
gttattggtg tgggcggctg ctggtttgcc tatatccaga accgttactc caaggagcac    720
atgaagaaga tgatgaagga cttggagggg ttacaccgag ctgagcagag tctgcatgac    780
cttcaggaaa ggctgcacaa ggcccaggag gagcaccgca cagtggaggt ggagaaggtc    840
catctggaaa agaagctgcg cgatgagatc aaccttgcta agcaggaagc ccagcggctg    900
aaggagctgc gggagggtac tgagaatgag cggagccgcc aaaaatatgc tgaggaggag    960
ttggagcagg ttcgggaggc cttgaggaaa gcagagaagg agctagaatc tcacagctca   1020
tggtatgctc cagaggccct tcagaagtgg ctgcagctga cacatgaggt ggaggtgcaa   1080
tattacaaca tcaagaagca aaatgctgag aagcagctgc tggtggccaa ggagggggct   1140
gagaagataa aaagaagag aaacacactc tttggcacct ccacgtggc ccacagctct    1200
tccctggatg atgtagatca taaaattcta acagctaagc aagcactgag cgaggtgaca   1260
gcagcattgc gggagcgcct gcaccgctgg caacagatca gatcctctg tggcttccag    1320
attgtcaaca accctggcat ccactcactg gtggctgccc tcaacataga ccccagctgg   1380
atgggcagta cacgccccaa ccctgctcac ttcatcatga ctgacgacgt ggatgacatg   1440
gatgaggaga ttgtgtctcc cttgtccatg cagtccccta gcctgcagag cagtgttcgg   1500
cagcgcctga cggagccaca gcatggcctg ggatctcaga gggatttgac ccattccgat   1560
tcggagtcct ccctccacat gagtgaccgc cagcgtgtgg cccccaaacc tcctcagatg   1620
agccgtgctg cagacgaggc tctcaatgcc atgacttcca atggcagcca ccggctgatc   1680
gaggggtcc acccagggtc tctggtggag aaactgcctg acagccctgc cctggccaag   1740
aaggcattac tggcgctgaa ccatgggctg acaaggcccc acagcctgat ggagctgagc   1800
ccctcagccc cacctggtgg ctctccacat ttggattctt cccgttctca cagccccagc   1860
tccccagacc cagacacacc atctccagtt ggggacagcc gagccctgca agccagccga   1920
aacacacgca ttccccacct ggctggcaag aaggctgtgg ctgaggagga taatggctct   1980
attggcgagg aaacagactc cagcccaggc cggaagaagt tccccctcaa aatctttaag   2040
aagcctctta agaagtag                                                 2058

<210> SEQ ID NO 16
<211> LENGTH: 1623
<212> TYPE: DNA
<213> ORGANISM: Homo sapiens

<400> SEQUENCE: 16
atggatgtat gcgtccgtct tgccctgtgg ctcctctggg gactcctcct gcaccagggc     60
cagagcctca gccatagtca cagtgagaag gcgacaggaa ccagctcggg ggccaactct    120
gaggagtcca ctgcagcaga gttttgccga attgacaagc ccctgtgtca cagtgaggat    180
gagaaactca gcttcgaggc agtccgtaac atccacaaac tgatggacga tgatgccaat    240
ggtgatgtgg atgtggaaga aagtgatgag ttcctgaggg aagacctcaa ttaccatgac    300
ccaacagtga acacagcac cttccatggt gaggataagc tcatcagcgt ggaggacctg    360
tggaaggcat ggaagtcatc agaagtatac aattggaccg tggatgaggt ggtacagtgg    420
ctgatcacat atgtggagct gcctcagtat gaggagacct ccggaagct gcagctcagt    480
ggccatgcca tgccaaggct ggctgtcacc aacaccacca tgacagggac tgtgctgaag    540
atgacagacc ggagtcatcg gcagaagctg cagctgaagg ctctggatac agtgctcttt    600
```

```
gggcctcctc tcttgactcg ccataatcac ctcaaggact tcatgctggt ggtgtctatc    660
gttattggtg tgggcggctg ctggtttgcc tatatccaga accgttactc caaggagcac    720
atgaagaaga tgatgaagga cttggagggg ttacaccgag ctgagcagag tctgcatgac    780
cttcaggaaa ggctgcacaa ggcccaggag gagcaccgca cagtggaggt ggagaaggtc    840
catctggaaa agaagctgcg cgatgagatc aaccttgcta agcaggaagc ccagcggctg    900
aaggagctgc gggagggtac tgagaatgag cggagccgcc aaaaatatgc tgaggaggag    960
ttggagcagg ttcgggaggc cttgaggaaa gcagagaagg agctagaatc tcacagctca   1020
tggtatgctc cagaggccct tcagaagtgg ctgcagctga cacatgaggt ggaggtgcaa   1080
tattacaaca tcaagaagca aaatgctgag aagcagctgc tggtggccaa ggagggggct   1140
gagaagataa aaagaagag aaacacactc tttggcacct tccacgtggc ccacagctct   1200
tccctggatg atgtagatca taaaattcta acagctaagc aagcactgag cgaggtgaca   1260
gcagcattgc gggagcgcct gcaccgctgg caacagatcg agatcctctg tggcttccag   1320
attgtcaaca accctggcat ccactcactg gtggctgccc tcaacataga ccccagctgg   1380
atgggcagta cacgccccaa ccctgctcac ttcatcatga ctgacgacgt ggatgacatg   1440
gatgaggaga ttgtgtctcc cttgtccatg cagtccccta gcctgcagag cagtgttcgg   1500
cagcgcctga cggagccaca gcatggcctg ggatctcaga gaggatcatc tctaaaggca   1560
aacaggctct ctagtaaggg atttgaccca ttccgattcg gagtcctccc tccacatgag   1620
tga                                                                 1623
```

<210> SEQ ID NO 17
<211> LENGTH: 159
<212> TYPE: PRT
<213> ORGANISM: Homo sapiens

<400> SEQUENCE: 17

```
Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
    130                 135                 140

Gln Gly Leu Trp Arg Arg Phe Asn Arg Pro Leu Leu Lys Gln Gln
145                 150                 155
```

<210> SEQ ID NO 18
<211> LENGTH: 63
<212> TYPE: PRT

<213> ORGANISM: Homo sapiens

<400> SEQUENCE: 18

Met Phe Ala Met Lys Thr Lys Ala Ala Leu Ala Ile Trp Cys Pro Gly
1               5                   10                  15

Tyr Ser Glu Thr Gln Ile Asn Ala Thr Gln Ala Met Lys Lys Arg Arg
                20                  25                  30

Lys Arg Lys Val Thr Thr Asn Lys Cys Leu Glu Gln Val Ser Gln Leu
            35                  40                  45

Gln Gly Leu Trp Arg Arg Phe Asn Arg Pro Leu Leu Lys Gln Gln
        50                  55                  60

<210> SEQ ID NO 19
<211> LENGTH: 480
<212> TYPE: DNA
<213> ORGANISM: Homo sapiens

<400> SEQUENCE: 19
atgttccctt tgccttact atatgttctg tcagtttctt tcaggaaaat cttcatctta      60
caacttgtag ggctggtgtt aacttacgac ttcactaact gtgactttga agagattaaa   120
gcagcctatc tcagtactat ttctaaagac ctgattacat atatgagtgg gaccaaaagt   180
accgagttca caacaccgt ctcttgtagc aatcggccac attgccttac tgaaatccag    240
agcctaacct tcaatcccac cgccggctgc gcgtcgctcg ccaaagaaat gttcgccatg    300
aaaactaagg ctgccttagc tatctggtgc ccaggctatt cggaaactca gataaatgct   360
actcaggcaa tgaagaagag gagaaaaagg aaagtcacaa ccaataaatg tctggaacaa   420
gtgtcacaat tacaaggatt gtggcgtcgc ttcaatcgac ctttactgaa acaacagtaa    480

<210> SEQ ID NO 20
<211> LENGTH: 192
<212> TYPE: DNA
<213> ORGANISM: Homo sapiens

<400> SEQUENCE: 20
atgttcgcca tgaaaactaa ggctgcctta gctatctggt gcccaggcta ttcggaaact      60
cagataaatg ctactcaggc aatgaagaag aggagaaaaa ggaaagtcac aaccaataaa   120
tgtctggaac aagtgtcaca attacaagga ttgtggcgtc gcttcaatcg acctttactg   180
aaacaacagt aa                                                        192

<210> SEQ ID NO 21
<211> LENGTH: 397
<212> TYPE: PRT
<213> ORGANISM: Homo sapiens

<400> SEQUENCE: 21

Met Arg Ser Pro Ser Ala Ala Trp Leu Leu Gly Ala Ala Ile Leu Leu
1               5                   10                  15

Ala Ala Ser Leu Ser Cys Ser Gly Thr Ile Gln Gly Thr Asn Arg Ser
                20                  25                  30

Ser Lys Gly Arg Ser Leu Ile Gly Lys Val Asp Gly Thr Ser His Val
            35                  40                  45

Thr Gly Lys Gly Val Thr Val Glu Thr Val Phe Ser Val Asp Glu Phe
        50                  55                  60

Ser Ala Ser Val Leu Thr Gly Lys Leu Thr Thr Val Phe Leu Pro Ile
65                  70                  75                  80

Val Tyr Thr Ile Val Phe Val Val Gly Leu Pro Ser Asn Gly Met Ala
                85                  90                  95

Leu Trp Val Phe Leu Phe Arg Thr Lys Lys His Pro Ala Val Ile
    100                 105                 110

Tyr Met Ala Asn Leu Ala Leu Ala Asp Leu Leu Ser Val Ile Trp Phe
        115                 120                 125

Pro Leu Lys Ile Ala Tyr His Ile His Gly Asn Asn Trp Ile Tyr Gly
    130                 135                 140

Glu Ala Leu Cys Asn Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
                165                 170                 175

Ile Val Asn Pro Met Gly His Ser Arg Lys Lys Ala Asn Ile Ala Ile
            180                 185                 190

Gly Ile Ser Leu Ala Ile Trp Leu Leu Ile Leu Leu Val Thr Ile Pro
        195                 200                 205

Leu Tyr Val Val Lys Gln Thr Ile Phe Ile Pro Ala Leu Asn Ile Thr
    210                 215                 220

Thr Cys His Asp Val Leu Pro Glu Gln Leu Leu Val Gly Asp Met Phe
225                 230                 235                 240

Asn Tyr Phe Leu Ser Leu Ala Ile Gly Val Phe Leu Phe Pro Ala Phe
                245                 250                 255

Leu Thr Ala Ser Ala Tyr Val Leu Met Ile Arg Met Leu Arg Ser Ser
            260                 265                 270

Ala Met Asp Glu Asn Ser Glu Lys Lys Arg Lys Arg Ala Ile Lys Leu
        275                 280                 285

Ile Val Thr Val Leu Ala Met Tyr Leu Ile Cys Phe Thr Pro Ser Asn
    290                 295                 300

Leu Leu Leu Val Val His Tyr Phe Leu Ile Lys Ser Gln Gly Gln Ser
305                 310                 315                 320

His Val Tyr Ala Leu Tyr Ile Val Ala Leu Cys Leu Ser Thr Leu Asn
                325                 330                 335

Ser Cys Ile Asp Pro Phe Val Tyr Tyr Phe Val Ser His Asp Phe Arg
            340                 345                 350

Asp His Ala Lys Asn Ala Leu Leu Cys Arg Ser Val Arg Thr Val Lys
        355                 360                 365

Gln Met Gln Val Ser Leu Thr Ser Lys Lys His Ser Arg Lys Ser Ser
    370                 375                 380

Ser Tyr Ser Ser Ser Ser Thr Thr Val Lys Thr Ser Tyr
385                 390                 395

<210> SEQ ID NO 22
<211> LENGTH: 1194
<212> TYPE: DNA
<213> ORGANISM: Homo sapiens

<400> SEQUENCE: 22
atgcggagcc ccagcgcggc gtggctgctg ggggccgcca tcctgctagc agcctctctc       60
tcctgcagtg gcaccatcca aggaaccaat agatcctcta aaggaagaag cctattggt      120 aaggttgatg gcacatccca cgtcactgga aaaggagtta cagttgaaac agtcttttct      180
gtggatgagt tttctgcatc tgtcctcact ggaaaactga ccactgtctt ccttccaatt      240
gtctacacaa ttgtgtttgt ggtgggtttg ccaagtaacg gcatggccct gtgggtcttt      300
cttttccgaa ctaagaagaa gcaccctgct gtgatttaca tggccaatct ggccttggct      360

```
gacctcctct ctgtcatctg gttccccttg aagattgcct atcacataca tggcaacaac    420
tggatttatg gggaagctct ttgtaatgtg cttattggct ttttctatgg caacatgtac    480
tgttccattc tcttcatgac ctgcctcagt gtgcagaggt attgggtcat cgtgaacccc    540
atggggcact ccaggaagaa ggcaaacatt gccattggca tctccctggc aatatggctg    600
ctgattctgc tggtcaccat ccctttgtat gtcgtgaagc agaccatctt cattcctgcc    660
ctgaacatca cgacctgtca tgatgttttg cctgagcagc tcttggtggg agacatgttc    720
aattacttcc tctctctggc cattggggtc tttctgttcc cagccttcct cacagcctct    780
gcctatgtgc tgatgatcag aatgctgcga tcttctgcca tggatgaaaa ctcagagaag    840
aaaaggaaga gggccatcaa actcattgtc actgtcctgg ccatgtacct gatctgcttc    900
actcctagta accttctgct tgtggtgcat tattttctga ttaagagcca gggccagagc    960
catgtctatg ccctgtacat tgtagccctc tgcctctcta cccttaacag ctgcatcgac   1020 cccttgtct attactttgt ttcacatgat ttcagggatc atgcaaagaa cgctctcctt   1080
tgccgaagtg tccgcactgt aaagcagatg caagtatccc tcacctcaaa gaaacactcc   1140
aggaaatcca gctcttactc ttcaagttca accactgtta agacctccta ttga         1194
```

<210> SEQ ID NO 23
<211> LENGTH: 15
<212> TYPE: PRT
<213> ORGANISM: Homo sapiens

<400> SEQUENCE: 23

Val Gly Arg Pro Glu Trp Trp Met Asp Tyr Gln Lys Arg Tyr Gly
1               5                   10                  15

<210> SEQ ID NO 24
<211> LENGTH: 6
<212> TYPE: PRT
<213> ORGANISM: Mus musculus

<400> SEQUENCE: 24

Ser Leu Ile Gly Arg Leu
1               5

<210> SEQ ID NO 25
<211> LENGTH: 37
<212> TYPE: PRT
<213> ORGANISM: Homo sapiens

<400> SEQUENCE: 25

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
                20                  25                  30

Gly Ser Lys Ala Phe
            35